(12) United States Patent
Roessler et al.

(10) Patent No.: US 7,851,191 B2
(45) Date of Patent: *Dec. 14, 2010

(54) PRODUCT AND PROCESS FOR TRANSFORMATION OF THRAUSTOCHYTRIALES MICROORGANISMS

(75) Inventors: Paul S. Roessler, San Diego, CA (US); T. Dave Matthews, San Diego, CA (US); Tom M. Ramseier, Poway, CA (US); James G. Metz, Longmont, CO (US)

(73) Assignee: Martek Biosciences Corporation, Columbia, MD (US)

( * ) Notice: Subject to any disclaimer, the term of this patent is extended or adjusted under 35 U.S.C. 154(b) by 285 days.

This patent is subject to a terminal disclaimer.

(21) Appl. No.: 11/925,885

(22) Filed: Oct. 27, 2007

(65) Prior Publication Data

US 2009/0192304 A1 Jul. 30, 2009

Related U.S. Application Data

(63) Continuation of application No. 11/021,712, filed on Dec. 22, 2004, which is a continuation of application No. 10/124,807, filed on Apr. 16, 2002, now Pat. No. 7,001,772.

(60) Provisional application No. 60/284,116, filed on Apr. 16, 2001.

(51) Int. Cl.
*C12N 9/10* (2006.01)
*C12N 1/20* (2006.01)
*C12N 15/74* (2006.01)
*C12P 21/06* (2006.01)
*C07H 21/04* (2006.01)

(52) U.S. Cl. .................. 435/193; 435/252.3; 435/69.1; 435/320.1; 536/23.2

(58) Field of Classification Search ........................ None
See application file for complete search history.

(56) References Cited

U.S. PATENT DOCUMENTS

| | | | |
|---|---|---|---|
| 4,626,505 A | 12/1986 | Falco | |
| 5,130,242 A | 7/1992 | Barclay | |
| 5,605,011 A | 2/1997 | Bedbrook et al. | |
| 5,661,017 A | 8/1997 | Dunahay et al. | |
| 5,804,408 A | 9/1998 | Hagiwara et al. | |
| 5,853,973 A | 12/1998 | Kakefuda et al. | |
| 6,027,900 A | 2/2000 | Allnut et al. | |
| 7,001,772 B2 * | 2/2006 | Roessler et al. | 435/471 |

FOREIGN PATENT DOCUMENTS

EP 0257993 A2 2/1998
WO WO 00/58485 10/2000
WO WO 00/73455 12/2000

OTHER PUBLICATIONS

Hill et al. Mutagenesis of *Escherichia coli* acetohydroxyacid synthase isoenzyme II and characterization of three herbicide-insensitive forms. Biochem J. Nov. 1, 1998;335 ( Pt 3):653-61.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Sanford et al., Optimizing the Biolistic Process for Different Biological Applications, Methods in Enzymology, vol. 217, 483-509, 1983.
Bingham et al., FEMS Microbiol. Lett., vol. 65, 77-82, 1989.
Mazur et al., Annu Rev. Plan Physiol. Plant mo. Biol., vol. 40, 441-470, 1989.
Perez et al., Plant Molecular Biology, vol. 13, 365-373, 1989.
Drocourt et al., Nucl. Acids Res., vol. 18 (13), 4009, 1990.
Gatignol et al., Gene, vol. 91, 35-41, 1990.
Accession X06104, NCBI Entrez, 1991.
Guerrero et al. Appl. Microbiol. Biotechnol., vol. 36., 759-762, 1992.
Sutton et al., Transgenic Res., vol. 1, 228-236, 1992.
Accession M13616, NCBI Entrez, 1994.
Dunahay et al., J Phycol., vol. 31, 1004-1012, 1995.
Messina et al., Gene, vol. 165, 213-217, 1995.
Apt et al., Mol. Gen. Genet., vol. 252, 572-579, 1996.
Cermakian et al., Nucl., Acids Res., vol. 24(4), 648-654, 1996.
Rohe et al., Curr. Gene, vol. 29, 587-590, 1996.
Sizova et al., Gene, vol. 181, 13-18, 1996.
Accession 2148078, NCBI Entrez, 1997.
Spychalla et al., Proc. Natl. Acad. Sci USA, vol. 94, 1142-1147, 1997.
Stevens et al., J. Phycol., vol. 33, 713-722, 1997.
Chipman et al., Biochim. Biophysica Acta, vol. 1385, 401-419, 1998.
Lumbreras et al., The Plant Journal, vol. 14, 4, 441-447, 1998.
Funke et al., Mol. Gen. Genet., vol. 262, 12-21, 1999.
Falco et al.: Nucleic Acids Research vol. 13, No. 11, 1985, pp. 4011-4027.
Kaestner et al.: Gene vol. 148, 1994, 67-70.

(Continued)

*Primary Examiner*—Robert B Mondesi
*Assistant Examiner*—Iqbal H Chowdhury
(74) *Attorney, Agent, or Firm*—Sterne, Kessler, Goldstein & Fox P.L.L.C.

(57) ABSTRACT

Disclosed are nucleic acid and amino acid sequences for acetolactate synthase, acetolactate synthase regulatory regions, α-tubulin promoter, a promoter from a Thraustochytriales polyketide synthase (PKS) system, and fatty acid desaturase promoter, each from a Thraustochytriales microorganism. Also disclosed are recombinant vectors useful for transformation of Thraustochytriales microorganisms, as well as a method of transformation of Thraustochytriales microorganisms. The recombinant nucleic acid molecules of the present invention can be used for the expression of foreign nucleic acids in a Thraustochytriales microorganism as well as for the deletion, mutation, or inactivation of genes in Thraustochytriales microorganisms.

24 Claims, 4 Drawing Sheets

OTHER PUBLICATIONS

Bekkaoui et al.: Curr. Genet. vol. 24, 1993, pp. 544-547.

Chang, A.K., and Duggleby, R.G., "Herbicide-resistant forms of *Arabidopsis thaliana* acetohydroxyacid synthase: characterization of the catalytic properties and sensitivity to inhibitors of four defined mutants," *Biochem J.* 333:765-777, Biochemical Society (1998).

Chong, C.-K., and Choi, J.-D., "Amino Acid Residues Conferring Herbicide Tolerance in Tobacco Acetolactate Synthase," *Biochem. Biophys. Res. Commun.* 279:462-467, Academic Press (Dec. 2000).

Ibdah, M., et al., "Homology Modeling of the Structure of Bacterial Acetohydroxy Acid Synthase and Examination of the Active Site by Site-Directed Mutagenesis," *Biochemistry* 35:16282-16291, American Chemical Society (1996).

Supplementary European Search Report for Application No. EP 02 71 9515, Munich, Germany, completed on Nov. 12, 2004.

International Serch Report for International application No. PCT/US02/12040, United States Patent and Trademark Office, Alexandrisa, Virginia, mailed on Nov. 25, 2003.

* cited by examiner

PRODUCT AND PROCESS FOR TRANSFORMATION OF THRAUSTOCHYTRIALES MICROORGANISMS

CROSS-REFERENCE TO RELATED APPLICATIONS

This application is a continuation of U.S. application Ser. No. 11/021,712, filed Dec. 22, 2004, which is a continuation of U.S. application Ser. No. 10/124,807, filed Apr. 16, 2002, which claims the benefit of priority under 35 U.S.C. §119(e) to U.S. Provisional Application Ser. No. 60/284,116, filed Apr. 16, 2001, entitled "Product and Process for Transformation of Thraustochytriales Microorganisms". The entire disclosure of each of U.S. Provisional Application Ser. No. 60/284,116, and U.S. application Ser. Nos. 10/124,807 and 11/021,712 is incorporated herein by reference.

FIELD OF THE INVENTION

This invention generally relates to an isolated nucleic acid molecule encoding a Thraustochytriales acetolactate synthase, including acetolactate synthases that confer reduced sensitivity to sulfonylurea compounds, imidazolinone-class inhibitors and/or pyrimidinyl oxybenzoates, onto microorganisms of the order Thraustochytriales; to recombinant nucleic acid molecules comprising selectable markers useful for the transformation of microorganisms of the order Thraustochytriales, and to methods of transforming such microorganisms using recombinant nucleic acid molecules of the present invention. The present invention also relates to gene promoters useful in Thraustochytriales expression systems. The recombinant nucleic acid molecules of the present invention can be used for the expression of foreign nucleic acids in a Thraustochytriales microorganism as well as for the deletion, mutation, or inactivation of genes in Thraustochytriales microorganisms.

BACKGROUND OF THE INVENTION

Developments have resulted in revision of the taxonomy of the Thraustochytrids. Taxonomic theorists place Thraustochytrids with the algae or algae-like protists. However, because of taxonomic uncertainty, it would be best for the purposes of the present invention to consider the strains described in the present invention as Thraustochytrids (Order: Thraustochytriales; Family: Thraustochytriaceae; Genus: *Thraustochytrium, Schizochytrium, Labyrinthuloides*, or *Japonochytrium*). Taxonomic changes are summarized below.

Strains of certain unicellular microorganisms disclosed and claimed herein are members of the order Thraustochytriales. Thraustochytrids are marine eukaryotes with a problematic taxonomic history. Problems with the taxonomic placement of the Thraustochytrids have been reviewed by Moss (1986), Bahnweb and Jackle (1986) and Chamberlain and Moss (1988).

For convenience purposes, the Thraustochytrids were first placed by taxonomists with other colorless zoosporic eukaryotes in the *Phycomycetes* (algae-like fungi). The name *Phycomycetes*, however, was eventually dropped from taxonomic status, and the Thraustochytrids were retained in the Oomycetes (the biflagellate zoosporic fungi). It was initially assumed that the Oomycetes were related to the heterokont algae, and eventually a wide range of ultrastructural and biochemical studies, summarized by Barr (1983) supported this assumption. The Oomycetes were in fact accepted by Leedale (1974) and other phycologists as part of the heterokont algae. However, as a matter of convenience resulting from their heterotrophic nature, the Oomycetes and Thraustochytrids have been largely studied by mycologists (scientists who study fungi) rather than phycologists (scientists who study algae).

From another taxonomic perspective, evolutionary biologists have developed two general schools of thought as to how eukaryotes evolved. One theory proposes an exogenous origin of membrane-bound organelles through a series of endosymbioses (Margulis 1970); e.g., mitochondria were derived from bacterial endosymbionts, chloroplasts from cyanophytes, and flagella from spirochaetes. The other theory suggests a gradual evolution of the membrane-bound organelles from the non-membrane-bounded systems of the prokaryote ancestor via an autogenous process (Cavalier-Smith 1975). Both groups of evolutionary biologists however, have removed the Oomycetes and Thraustochytrids from the fungi and place them either with the chromophyte algae in the kingdom Chromophyta (Cavalier-Smith 1981) (this kingdom has been more recently expanded to include other protists and members of this kingdom are now called Stramenopiles) or with all algae in the kingdom Protoctista (Margulis and Sagan (1985).

With the development of electron microscopy, studies on the ultrastructure of the zoospores of two genera of Thraustochytrids, *Thraustochytrium* and *Schizochytrium*, (Perkins 1976; Kazama 1980; Barr 1981) have provided good evidence that the Thraustochytriaceae are only distantly related to the Oomycetes. Additionally, genetic data representing a correspondence analysis (a form of multivariate statistics) of 5 S ribosomal RNA sequences indicate that Thraustochytriales are clearly a unique group of eukaryotes, completely separate from the fungi, and most closely related to the red and brown algae, and to members of the Oomycetes (Mannella et al. 1987). Most taxonomists have agreed to remove the Thraustochytrids from the Oomycetes (Bartnicki-Garcia 1988).

In summary, employing the taxonomic system of Cavalier-Smith (1981, 1983), the Thraustochytrids are classified with the chromophyte algae in the kingdom Chromophyta, (Stramenopiles). This places them in a completely different kingdom from the fungi, which are all placed in the kingdom Eufungi. The taxonomic placement of the Thraustochytrids is therefore summarized below:

Kingdom: Chromophyta (Stramenopiles)
Phylum: Heterokonta
Order: Thraustochytriales
Family: Thraustochytriaceae
Genus: *Thraustochytrium, Schizochytrium, Labyrinthuloides, or Japonochytrium*

Some early taxonomists separated a few original members of the genus *Thraustochytrium* (those with an amoeboid life stage) into a separate genus called *Ulkenia*. However it is now known that most, if not all, Thraustochytrids (including *Thraustochytrium* and *Schizochytrium*), exhibit amoeboid stages and as such, *Ulkenia* is not considered by some to be a valid genus. As used herein, the genus *Thraustochytrium* will include *Ulkenia*.

Despite the uncertainty of taxonomic placement within higher classifications of Phylum and Kingdom, the Thraustochytrids remain a distinctive and characteristic grouping whose members remain classifiable within the order Thraustochytriales.

*Schizochytrium* and other Thraustochytriales microorganisms have substantial existing and potential commercial value because of their ability to produce large quantities of lipoidal compounds, including highly unsaturated fatty acids (HUFAs) and various carotenoids (e.g., astaxanthin). Omega-3 highly unsaturated fatty acids are of significant commercial interest in that they have been recently recognized as important dietary compounds for preventing arteriosclerosis and coronary heart disease, for alleviating inflammatory conditions and for retarding the growth of tumor cells. These beneficial effects are a result both of omega-3 HUFAs causing competitive inhibition of compounds produced from omega-6 fatty acids, and from beneficial compounds produced directly from the omega-3 HUFAs themselves (Simopoulos et al., 1986). Omega-6 fatty acids are the predominant HUFAs found in plants and animals. Therefore, further development of Thraustochytriales microorganisms as commercial production organisms will benefit significantly from the ability to make specific genetic changes to the organisms via recombinant DNA technology, including enhancing the production of the highly valuable HUFAs and carotenoids by such organisms. In addition, the ability to gain a better understanding of the biochemistry and molecular biology of this poorly characterized group of organisms will provide valuable information that can be used to guide future strain development efforts. Prior to the present invention, however, methods and recombinant constructs suitable for transforming Thraustochytrids, including members of the genera, *Schizochytrium* and *Thraustochytrium* were not available. Importantly, the development of selectable markers that are particularly useful for transforming Thraustochytriales microorganisms and the identification of Thraustochytriales-specific promoter sequences were not available prior to the present invention.

Prior investigators have described transformation methods and reagents for use in various microorganisms, including in microalgae that are not members of the Thraustochytriales order. U.S. Pat. No. 6,027,900 to Allnutt et al. discloses genetic fusions for use in genetic engineering of eukaryotic algae, and particularly, *Phaeodactylum tricornutum*, using a promoter for a photosynthetic algal light harvesting gene and the Sh ble gene from *Streptoalloteichus hindustanus* as a selectable marker. The cells are grown in high concentrations of salt (e.g., 10-35 g/L) and Zeocin™ for selection of transformants. The microalgal cells suitable for transformation using such a method are photosynthetic microalgae that can be grown under the high salt conditions. U.S. Pat. No. 5,661,017 to Dunahay et al. discloses a method to transform cholorophyll C-containing algae (e.g., Diatoms) using a recombinant construct comprising a selectable marker operatively linked to a regulatory control sequence suitable for expression of the marker in the cholorophyll C-containing algae. The selectable marker is disclosed as being any suitable marker, including markers isolated from bacterial and fungal sources, and is preferably neomycin phosphotransferase. The regulatory control sequence can include any regulatory sequence derived from a cholorophyll C-containing algae, and preferably, from *Cyclotella cryptica* (e.g., a *C. cryptica* acetyl-CoA carboxylase regulatory sequence).

However, such methods are not readily transferable to the transformation of Thraustochytriales microorganisms, because, prior to the present invention, the transformation of microorganisms such as Thraustochytriales (e.g., microalgae) was far from routine. Markers and transformation systems that have become well developed for bacteria and yeast are not necessarily readily adaptable to other microorganisms. Indeed, U.S. Pat. No. 5,661,017 notes that "there has been little success in developing transformation systems for eucaryotic microalgae" (col. 1, lines 49-51), which is partly due to the difficulty of introducing foreign DNA into such microorganisms, and partly due to a lack of suitable markers and vectors for use in such transformation. The system described in U.S. Pat. No. 5,661,017 was developed specifically for the chlorophyll C-containing algae because those inventors believed them to be amenable to genetic transformation, particularly as compared to other algae. Similarly, U.S. Pat. No. 6,027,900, which teaches a transformation method that is specific to photosynthetic microalgae, speaks to the belief that most algae are refractory to any type of genetic manipulation (col. 1, lines 39-47). The systems adapted for bacteria, yeast, insect and animal cells have not been readily adapted to microalgae. Therefore, prior to the present invention, there was still a need in the art for effective transformation systems and methods that are specific for microalgae.

Additionally, although the order Thraustochytriales is now grouped with the chromophyte algae in the Stramenopiles, there is still an opinion by some in the art that these microorganisms are quite different from most microalgae, and some of those of skilled in the art have the opinion that Thraustochytriales members may not be properly classified as microalgae at all. Microorganisms considered to be microalgae have evolved at least four separate times during evolution, leading the "microalgal" type microorganisms to be placed in different kingdoms (e.g. the red algae, green algae and golden algae (Chromophyta) are all in separate kingdoms). As a result, transformation systems that have been demonstrated to be useful in other microalgae are not expected to be useful for Thraustochytriales. Therefore, despite the commercial value of Thraustochytriales microorganisms, the ability to make use of the full potential of such microorganisms by genetic engineering has not heretofore been realized. Prior to the present invention, the present inventors were not aware of any promoters, selectable markers, or vectors useful for transformation of Thraustochytriales microorganisms, nor was there any knowledge regarding what selection systems could be used in or adapted to Thraustochytriales.

In summary, there is a need in the art to develop methods for transforming Thraustochytriales microorganisms, thereby providing a means to create strains with enhanced commercial value. In addition, there is a need in the art to develop methods for mutation or inactivation of specific genes by homologous or nonhomologous recombination in Thraustochytriales microorganisms, providing a new way to alter cellular metabolism and to identify the functions of specific genes in Thraustochytriales.

SUMMARY OF THE INVENTION

One embodiment of the present invention relates to an isolated nucleic acid molecule comprising a nucleic acid sequence selected from the group consisting of: (a) a nucleic acid sequence encoding a protein having an amino acid sequence selected from the group consisting of SEQ ID NO:15, SEQ ID NO:19, SEQ ID NO:22 and SEQ ID NO:24, wherein the protein is an acetolactate synthase; (b) a nucleic acid sequence encoding a protein having an amino acid sequence that is at least about 75% identical to an amino acid sequence of (a), wherein the protein is an acetolactate synthase; and, (c) a nucleic acid sequence that is fully complementary to the nucleic acid sequence of (a) or (b). In one aspect, such a nucleic acid sequence encodes a protein having an amino acid sequence that is at least about 85% identical to an amino acid sequence of (a), and wherein the protein is an acetolactate synthase. In another aspect, such a nucleic acid sequence encodes a protein having an amino acid sequence that is at least about 95% identical to an amino acid sequence of (a), and wherein the protein is an acetolactate synthase. In yet another aspect, such a nucleic acid sequence encodes a protein having an amino acid sequence that differs from SEQ ID NO:15 by an amino acid deletion, insertion, or substitution at an amino acid position selected from the group consisting of: 116G, 117A, 192P, 200A, 251K, 358M, 383D, 592V, 595W, and 599F. In one aspect, the nucleic acid sequence encodes a protein having an amino acid sequence selected from the group consisting of SEQ ID NO:15, SEQ ID NO:19, SEQ ID NO:22 and SEQ ID NO:24, and wherein the protein is an acetolactate synthase. In yet another aspect, the nucleic acid sequence is selected from the group consisting of nucleotides 1260-3314 of SEQ ID NO:14, nucleotides 1260-3314 of SEQ ID NO:18, nucleotides 1260-3314 of SEQ ID NO:21, and nucleotides 1260-3314 of SEQ ID NO:23.

Preferably, expression of the protein encoded by the nucleic acid sequences identified above confers reduced sensitivity to compounds selected from the group consisting of: sulfonylurea compounds, imidazolinone-class inhibitors, and pyrimidinyl oxybenzoates, onto a microorganism of the Order Thraustochytriales that is transformed with such a nucleic acid molecule. In one aspect of this embodiment, the nucleic acid sequence encodes a protein having an amino acid sequence selected from the group consisting of SEQ ID NO:19, SEQ ID NO:22 and SEQ ID NO:24. In another aspect of this embodiment, the nucleic acid sequence is selected from the group consisting of: nucleotides 1260-3314 of SEQ ID NO:14, nucleotides 1260-3314 of SEQ ID NO:18, nucleotides 1260-3314 of SEQ ID NO:21, and nucleotides 1260-3314 of SEQ ID NO:23.

In one embodiment of the present invention, the nucleic acid sequence described above encodes a *Schizochytrium* acetolactate synthase. In one aspect, expression of the *Schizochytrium* acetolactate synthase confers reduced sensitivity to compounds selected from the group consisting of: sulfonylurea compounds, imidazolinone-class inhibitors, and pyrimidinyl oxybenzoates, onto a microorganism of the Order Thraustochytriales that is transformed with the nucleic acid molecule.

Another embodiment of the present invention relates to a recombinant nucleic acid molecule comprising any of the isolated nucleic acid molecules described above, operatively linked to a transcription control sequence. Another embodiment of the present invention relates to a recombinant microorganism of the order Thraustochytriales that is transformed with such a recombinant nucleic acid molecule.

Yet another embodiment of the present invention relates to a recombinant vector for transformation of microorganisms of the Order Thraustochytriales. The vector includes a nucleic acid sequence encoding an acetolactate synthase that confers reduced sensitivity to compounds selected from the group consisting of: sulfonylurea compounds, imidazolinone-class inhibitors, and pyrimidinyl oxybenzoates, onto a microorganism of the order Thraustochytriales. The acetolactate synthase has an amino acid sequence selected from the group consisting of: (a) an amino acid sequence selected from the group consisting of SEQ ID NO:19, SEQ ID NO:22 and SEQ ID NO:24; and, (b) an amino acid sequence that is at least about 75% identical to an amino acid sequence of (a). The nucleic acid sequence encoding an acetolactate synthase is operatively linked to a transcription control sequence. In one aspect, the recombinant vector is an expression vector. In another aspect, the recombinant vector is a targeting vector. In other aspects, the nucleic acid sequence in the vector encodes an acetolactate synthase having an amino acid sequence that is at least about 85% identical, and in another aspect, at least about 95% identical, to an amino acid sequence of (a). In one aspect, the nucleic acid sequence encodes a protein having an amino acid sequence that differs from SEQ ID NO:15 by an amino acid deletion, insertion, or substitution at an amino acid position selected from the group consisting of: 116G, 117A, 192P, 200A, 251K, 358M, 383D, 592V, 595W, and 599F. In a preferred aspect, the acetolactate synthase has an amino acid sequence selected from the group consisting of SEQ ID NO:19, SEQ ID NO:22 and SEQ ID NO:24. In another aspect, the nucleic acid sequence is selected from the group consisting of: nucleotides 1260-3314 of SEQ ID NO:18, nucleotides 1260-3314 of SEQ ID NO:21, and nucleotides 1260-3314 of SEQ ID NO:23. The transcription control sequence in the recombinant vector can include, but is not limited to, a Thraustochytriales α-tublin promoter, a Thraustochytriales acetolactate synthase promoter, a promoter from a Thraustochytriales polyketide synthase (PKS) system, or a Thraustochytriales fatty acid desaturase promoter. In one aspect, the vector comprises a nucleic acid sequence selected from the group consisting of SEQ ID NO:18, SEQ ID NO:21, and SEQ ID NO:23.

Yet another embodiment of the present invention relates to a method for transformation of cells of a microorganism of the Order Thraustochytriales. The method includes a first step of (a) introducing into cells of a microorganism of the Order Thraustochytriales a recombinant nucleic acid molecule comprising a nucleic acid sequence encoding an acetolactate synthase that confers onto the cells reduced sensitivity to compounds selected from the group consisting of: sulfonylurea compounds, imidazolinone-class inhibitors, and pyrimidinyl oxybenzoates, wherein the acetolactate synthase has an amino acid sequence selected from the group consisting of: (i) an amino acid sequence selected from the group consisting of SEQ ID NO:19, SEQ ID NO:22 and SEQ ID NO:24; and, (ii) an amino acid sequence that is at least about 75% identical to an amino acid sequence of (i). The method includes a second step of (b) selecting cells that have been successfully transformed with the recombinant nucleic acid molecule by culturing the cells of (a) in a medium containing at least one compound that is inhibitory to untransformed cells, the compound being selected from the group consisting of: a sulfonylurea compound, an imidazolinone-class inhibitor, and pyrimidinyl oxybenzoates. In one aspect, the nucleic acid sequence encodes an acetolactate synthase having an amino acid sequence that is at least about 85% identical, and more preferably at least about 95% identical, to an amino acid sequence of (i). In one aspect, the nucleic acid sequence encodes a protein having an amino acid sequence that differs from SEQ ID NO:15 by an amino acid deletion, insertion, or substitution at an amino acid position selected from the group consisting of: 116G, 117A, 192P, 200A, 251K, 358M, 383D, 592V, 595W, and 599F. In another aspect, the acetolactate synthase has an amino acid sequence selected from the group consisting of SEQ ID NO:19, SEQ ID NO:22 and SEQ ID NO:24. Preferably, the nucleic acid sequence is selected from the group consisting of: nucleotides 1260-3314 of SEQ ID NO:18, nucleotides 1260-3314 of SEQ ID NO:21, and nucleotides 1260-3314 of SEQ ID NO:23. In yet another aspect, the nucleic acid sequence is operatively linked to a transcription control sequence selected from the group consisting of a Thraustochytriales α-tublin promoter, a Thraustochytriales acetolactate synthase promoter, a promoter from a Thraustochytriales polyketide synthase (PKS) system, and a Thraustochytriales fatty acid desaturase promoter.

In one aspect, the recombinant nucleic acid molecule further comprises a nucleic acid sequence encoding a protein to be produced by the cell, wherein the nucleic acid sequence encoding the protein is operatively linked to a transcription control sequence. In one aspect of this embodiment, the protein is associated with the synthesis of a fatty acid selected from the group consisting of docosahexaenoic acid (DHA), docosapentaenoic acid (DPA), eicosapentaenoic acid (EPA) and arachadonic acid (ARA). In another aspect of this embodiment, the protein is selected from the group consisting of: a fatty acid synthase, a fatty acid desaturase, a fatty acid elongase, a protein associated with a polyketide synthase complex and a protein associated with incorporation of fatty acids into phospholipids or into triacylglycerol molecules. In one aspect, the protein is an ω-3 fatty acid desaturase is encoded by a nucleic acid sequence SEQ ID NO:29. In another aspect, the protein is a polyenoic fatty acid isomerase. In yet another aspect, the protein is selected from the group consisting of HMG-CoA synthase, HMG-CoA reductase, squalene synthase, phytoene synthase, phytoene desaturase, a carotenoid cyclase, a carotenoid hyroxylase, a carotenoid ketolase, vitamin E and lipoic acid.

In another aspect of the present method, the recombinant nucleic acid molecule in step (a) further comprises a nucleic acid sequence that hybridizes with a target nucleic acid sequence in the microorganism such that a gene comprising the target nucleic acid sequence is mutated or inactivated by homologous recombination with the second nucleic acid sequence. In this aspect, the target nucleic acid sequence can encode a protein selected from the group consisting of lipases, fatty acid oxidation enzymes, proteins involved in carbohydrate synthesis, proteins involved in synthesis of products of isoprenoid pathways, proteins involved in synthesis of cell wall components, proteins involved in the saturated fatty acid synthesis pathways, proteins involved in the polyunsaturated fatty acid synthesis pathways, proteins associated with a polyketide synthase complex, and proteins associated with incorporation of fatty acids into phospholipids or triacylglycerol molecules.

The present method can further include the step of introducing into the cell at least one additional recombinant nucleic acid molecule comprising a nucleic acid sequence encoding a protein to be expressed, the nucleic acid sequence being operatively linked to a transcription control sequence. In another aspect, the method can further include a step of introducing into the cell at least one additional recombinant nucleic acid molecule comprising a second nucleic acid sequence that hybridizes with a target nucleic acid sequence in the microorganism such that a gene comprising the target nucleic acid sequence is mutated or inactivated by homologous recombination with the second nucleic acid sequence. In another aspect, the method can further include the step of introducing into the cell a recombinant nucleic acid molecule comprising a nucleic acid sequence encoding a bleomycin-binding protein. In this aspect, the recombinant nucleic acid molecule comprising a nucleic acid sequence encoding a bleomycin-binding protein further comprises a nucleic acid sequence encoding a second protein to be expressed by the cell, wherein the nucleic acid sequence encoding the second protein is operatively linked to a transcription control sequence. Such a transcription control sequence can include, but is not limited to, a Thraustochytriales α-tublin promoter, a Thraustochytriales acetolactate synthase promoter, a promoter from a Thraustochytriales polyketide synthase (PKS) system, and a Thraustochytriales fatty acid desaturase promoter. In a further aspect of this embodiment, the recombinant nucleic acid molecule comprising a nucleic acid sequence encoding a bleomycin-binding protein further comprises a second nucleic acid sequence that hybridizes with a target nucleic acid sequence in the microorganism such that a gene comprising the target nucleic acid sequence is mutated or inactivated by homologous recombination with the second nucleic acid sequence. In one embodiment, the recombinant nucleic acid molecule comprises a nucleic acid sequence SEQ ID NO:9.

In the method of the present invention the microorganism can be from a genus that includes, but is not limited to, *Thraustochytrium, Labyrinthuloides, Japonochytrium*, and *Schizochytrium*. In one aspect, the microorganism is from a species including, but not limited to, *Schizochytrium sp., Schizochytrium aggregatun, Schizochytrium limacinum, Thraustochytrium sp., Thraustochytrium striatum, Thraustochytrium aureum, Thraustochytrium roseum,* and *Japonochytrium sp.*

In one embodiment of the present method, the step of introducing is performed by a method selected from the group consisting of particle bombardment, electroporation, microinjection, lipofection, adsorption, infection and protoplast fusion.

Another embodiment of the present invention relates to a recombinant microorganism of the order Thraustochytriales, transformed with a recombinant nucleic acid molecule comprising a nucleic acid sequence encoding an acetolactate synthase that confers onto the microorganism reduced sensitivity to compounds selected from the group consisting of: sulfonylurea compounds, imidazolinone-class inhibitors, and pyrimidinyl oxybenzoates. The acetolactate synthase has an amino acid sequence selected from the group consisting of: (a) an amino acid sequence selected from the group consisting of SEQ ID NO:19, SEQ ID NO:22 and SEQ ID NO:24; and, (b) an amino acid sequence that is at least about 75% identical to an amino acid sequence of (a). In one aspect, the nucleic acid sequence encodes an acetolactate synthase having an amino acid sequence that is at least about 85% identical to an amino acid sequence of (a). In another aspect, the nucleic acid sequence encodes an acetolactate synthase having an amino acid sequence that is at least about 95% identical to an amino acid sequence of (a). In another aspect, the acetolactate synthase has an amino acid sequence selected from the group consisting of SEQ ID NO:19, SEQ ID NO:22 and SEQ ID NO:24. In yet another aspect, the nucleic acid sequence is selected from the group consisting of: nucleotides 1260-3314 of SEQ ID NO:18, nucleotides 1260-3314 of SEQ ID NO:21, and nucleotides 1260-3314 of SEQ ID NO:23. In yet another aspect, the recombinant nucleic acid molecule comprises a nucleic acid sequence selected from the group consisting of SEQ ID NO:18, SEQ ID NO:21 and SEQ ID NO:23. Preferably, the nucleic acid sequence encoding an acetolactate synthase is operatively linked to a promoter that functions in a Thraustochytriales microorganism. In one aspect, the nucleic acid sequence encoding an acetolactate synthase is operatively linked to a transcription control sequence selected from the group consisting of a Thraustochytriales α-tublin promoter, a Thraustochytriales acetolactate synthase promoter, a promoter from a Thraustochytriales polyketide synthase (PKS) system, and a Thraustochytriales fatty acid desaturase promoter. In one embodiment, the recombinant nucleic acid molecule further comprises a nucleic acid sequence encoding a first protein for production by the microorganism, wherein the nucleic acid sequence encoding the first protein is operatively linked to a transcription control sequence. In another embodiment, the recombinant cell is further transformed with a recombinant nucleic acid molecule comprising a nucleic acid sequence encoding a bleomycin-binding protein. Preferably, the recombinant nucleic acid molecule comprises a nucleic acid sequence SEQ ID NO:9. In one embodiment, the recombinant nucleic acid molecule comprising a nucleic acid sequence encoding a bleomycin-binding protein further comprises a nucleic acid sequence encoding a second protein for production by the cell, wherein the nucleic acid sequence encoding the second protein is operatively linked to a transcription control sequence. In one embodiment, the microorganism also includes at least one additional recombinant nucleic acid molecule comprising a nucleic acid sequence encoding a protein for production by the cell.

Yet another embodiment of the present invention relates to an isolated nucleic acid molecule comprising a nucleic acid sequence selected from the group consisting of: (a) nucleotides 441-894 of SEQ ID NO:9; (b) a nucleic acid sequence that is at least about 95% identical to nucleotides 441-894 of SEQ ID NO:9 over the full length of nucleotides 441-894 of SEQ ID NO:9, wherein the nucleic acid sequence has at least basal α-tubulin promoter transcriptional activity; and (c) an isolated polynucleotide comprising a nucleic acid sequence that is fully complementary to the polynucleotide of (a) or (b). Preferably, the isolated nucleic acid molecule comprises a nucleic acid sequence selected from the group consisting of SEQ ID NO:4 and nucleotides 441-894 of SEQ ID NO:9.

Yet another embodiment of the present invention relates to a recombinant vector for transformation of microorganisms of the Order Thraustochytriales, comprising a nucleic acid sequence encoding a bleomycin binding protein operatively linked to a promoter selected from the group consisting of a Thraustochytriales α-tublin promoter, a Thraustochytriales acetolactate synthase promoter, a promoter from a Thraustochytriales polyketide synthase (PKS) system, and a Thraustochytriales fatty acid desaturase promoter. In one aspect, the Thraustochytriales acetolactate synthase promoter comprises nucleotides 1-1259 of SEQ ID NO:14. In one aspect, the α-tublin promoter comprises a nucleic acid sequence selected from the group consisting of nucleotides 441-894 of SEQ ID NO:9, and a nucleic acid sequence that is at least about 95% identical to nucleotides 441-894 of SEQ ID NO:9 over the full length of nucleotides 441-894 of SEQ ID NO:9, wherein the nucleic acid sequence has at least basal α-tublin promoter transcriptional activity. In another aspect, a promoter from a Thraustochytriales PKS system comprises SEQ ID NO:34 or a nucleic acid sequence contained within SEQ ID NO:34, wherein said promoter has at least basal PKS promoter transcriptional activity. In another aspect, the recombinant vector comprises a nucleic acid sequence selected from the group consisting of SEQ ID NO:8 and SEQ ID NO:9.

DETAILED DESCRIPTION OF THE INVENTION

This invention comprises methods and related materials to genetically transform microorganisms of the order Thraustochytriales. All of the strains of unicellular microorganisms disclosed herein for use as a transformant of the recombinant constructs of the present invention, which can generally also be referred to as Thraustochytrids, are members of the order Thraustochytriales. According to the present invention, the phrases "Thraustochytrid", "Thraustochytriales microorganism" and "microorganism of the order Thraustochytriales" can be used interchangeably. The present inventors are not aware of any prior reports that describe a transformation system for *Schizochytrium* or any other Thraustochytriales microorganism. The transformation systems described herein can be used to introduce foreign genes into microorganisms of the order Thraustochytriales, thereby providing a means to create strains with enhanced commercial value. In addition, this invention enables the mutation or inactivation of specific genes by homologous or nonhomologous recombination, providing a new way to alter cellular metabolism and to identify the functions of specific genes in Thraustochytriales microorganisms.

More specifically, the present inventors have demonstrated genetic transformation of a Thraustochytriales microorganism of the genus, *Schizochytrium* (Order: Thraustochytriales; Family: Thraustochytriaceae; Genus: *Schizochytrium*), by the use of two types of transformation vectors. These vectors can be introduced into cells by standard methods, followed by identification and isolation of recombinant cells based on their ability to grow in the presence of selective compounds. The present inventors have demonstrated the effectiveness of these vectors by introducing them via particle bombardment, but other means to introduce the vectors can also be used (e.g., electroporation) and are known in the art and are intended to be encompassed by the present invention.

Figure 2:
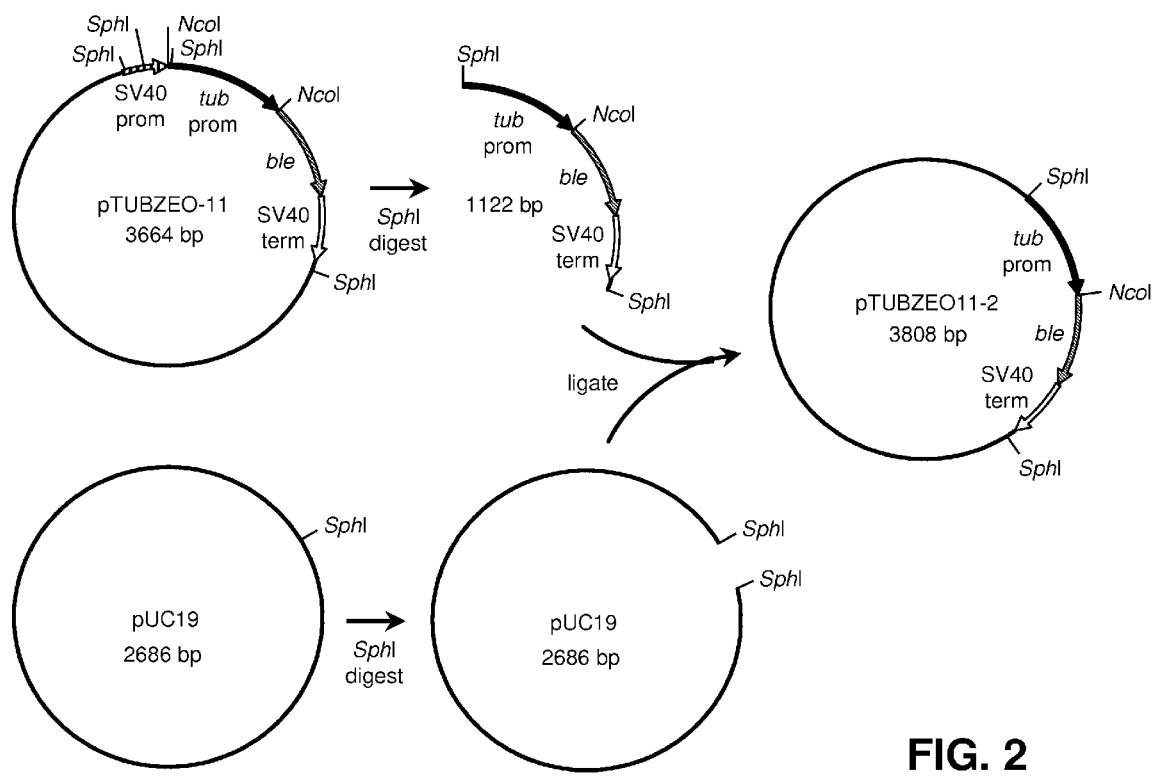
FIG. 2 illustrates the construction of recombinant plasmid pTUBZEO11-2.
Figure 3A:
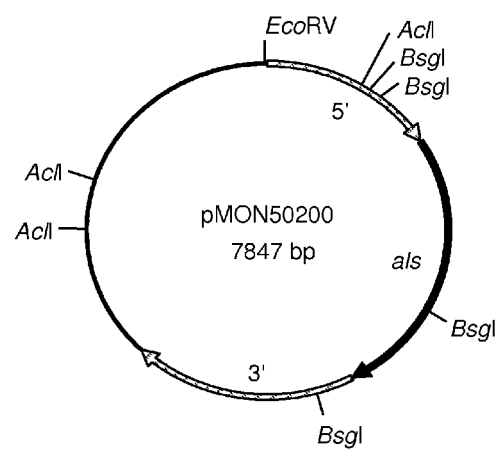
FIG. 3A illustrates recombinant plasmid pMON50200.
Figure 3B:
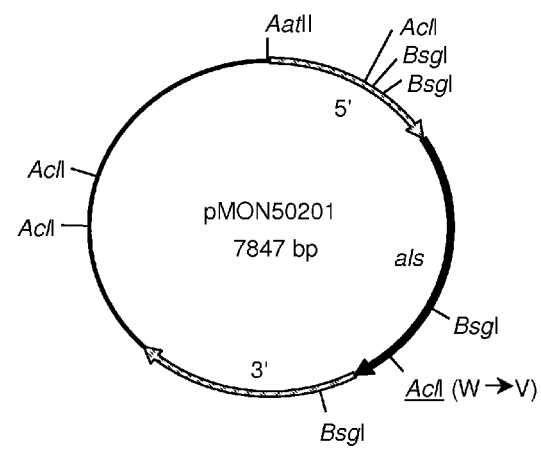
FIG. 3B illustrates recombinant plasmid pMON50201.
Figure 3C:
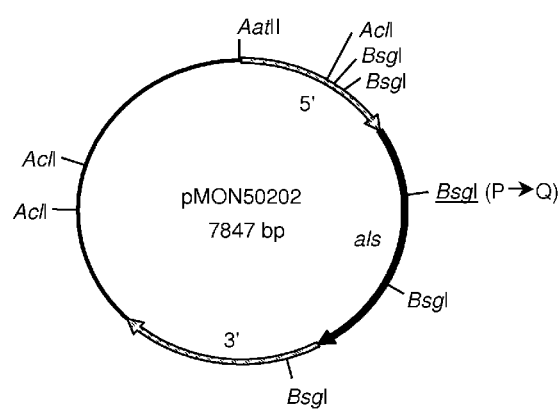
FIG. 3C illustrates recombinant plasmid pMON50202.
Figure 3D:
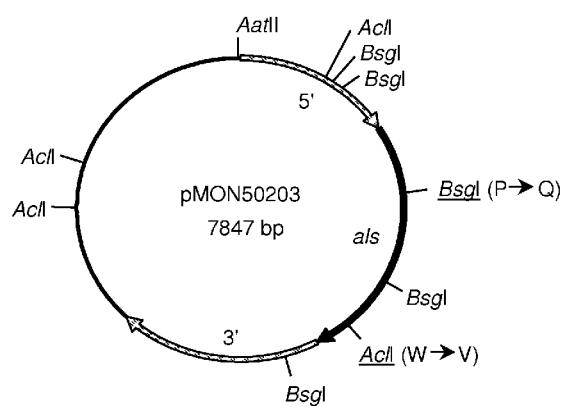
FIG. 3D illustrates recombinant plasmid pMON50203.

For one transformation vector, exemplified herein by the recombinant vector denoted pTUBZEO11-2, a chimeric gene was created in which the ble gene (which encodes a "bleomycin-binding protein") from *Streptoalloteichus hindustanus* was placed downstream from a Schizochytrium tubulin gene promoter. An SV40 terminator was placed downstream from the ble gene in this construct. This vector enables expression of the ble gene in *Schizochytrium*, thereby conferring resistance to Zeocin™ and related compounds, which are toxic to wild-type cells when included in the growth medium at appropriate levels. The source of the ble gene and SV40 terminator in this construct was a commercially available vector, named pSV40/Zeo, which was acquired from Invitrogen Corporation (Carlsbad, Calif.) (Technical Manual 180202, Version B, "ZeoCas sette Vectors"; Invitrogen Corporation, 1600 Faraday Ave., Carlsbad, Calif. 92008). The tubulin gene promoter was isolated via the polymerase chain reaction; one of the primers used for the reaction was based on sequence data obtained through a random *Schizochytrium* cDNA sequencing project. The map of pTUBZEO11-2 is shown in FIG. 2, and the nucleotide sequence of pTUBZEO11-2 is represented by SEQ ID NO:9. Transformation of *Schizochytrium* with this vector was confirmed by the use of the polymerase chain reaction and Southern blot analysis to detect the presence of vector sequences integrated into the *Schizochytrium* genome.

The ble gene has been used by prior investigators as a selectable marker for genetic transformation of a variety of organisms, including bacteria, non-Thraustochytrid microalgae, fungi, protozoa, plants, and animal cells (See, for example, U.S. Pat. No. 6,027,900; Lumbreras et al., 1998, *Plant J.* 14:441-447; Rohe et al., 1996, *Curr. Genet.* 29:587-590; Messina et al., 1995, *Gene* 165:213-217; Guerrero et al., 1992, *Appl. Microbiol. Biotechnol.* 36:759-762; Perez et al., 1989, *Plant Mol. Biol.* 13:365-373; Gatigno et al., 1990 *Gene* 91:35-41). The ble gene encodes a "bleomycin-binding protein" that confers resistance to several antibiotics, including bleomycin, phleomycin, and Zeocin™ (Drocourt et al., 1990, *Nucleic Acids Res.* 18:4009). This gene is available commercially from Invitrogen Corporation, which was the source of the gene that the present inventors used for creating the Schizochytrium transformation vector pTUBZEO11-2. However, the present inventors are believed to be the first to produce a transformation vector in which the ble gene is attached to a Thraustochytrid promoter in a manner that allows expression of the gene in Thraustochytrids.

A second set of transformation vectors was created by in vitro site-directed mutagenesis of an acetolactate synthase gene (als) that the present inventors isolated from a *Schizochytrium* genomic library. These mutations change the amino acid sequence of the encoded enzyme (ALS) in such a way that it is much less sensitive to sulfometuron methyl and other sulfonylurea compounds, as well as imidazolinone-class inhibitors and pyrimidinyl oxybenzoates, to which microorganisms of the order Thraustochytriales are sensitive. Sulfonylurea compounds such as sulfometuron methyl (SMM) are often toxic to cells because they are able to bind to and inactivate the enzyme acetolactate synthase (ALS) from a variety of organisms. ALS catalyzes the first step in the biosynthesis of the amino acids valine, leucine, and isoleucine. Inidazolinones, triazolopyrimidines, and other compounds have also been shown to bind to and inactivate ALS from certain organisms. Mutant forms of genes that encode acetolactate synthase (also known as acetohydroxy acid synthase) from other organisms have been used previously as selectable markers for transformation of yeast and plants (*Annu. Rev. Plant Physiol. Plant Mol. Biol.* 40:441-470, 1989). However, there are no reports prior to the present invention that describe the sequence or properties of the als gene from *Schizochytrium* or any other Thraustochytriales member, or the use of mutant Thraustochytriales als genes to confer resistance to sulfonylurea, imidazolinone or pyrimidinyl oxybenzoate compounds. In fact, to the present inventors' knowledge, there have not even been any published reports regarding the sensitivity of Thraustochytriales microorganisms to these selective agents, including sulfometuron methyl, and therefore, it was not known prior to the present invention whether such a selectable marker would even be feasible for use in a Thraustochytrid transformation system. It is noteworthy that genes with substantial homology to known als genes occur in various organisms, but do not encode enzymes that are able to catalyze the synthesis of acetolactate (*Biochimica et Biophysica Acta* 1385:401-419, 1998). Therefore, it would not have been obvious that a cloned als homologue in fact encodes ALS. In order to definitively determine whether the cloned Schizochytrium gene was a true als gene, the present inventors demonstrated, through transformation experiments, a positive correlation of sulfometuron methyl-resistance with expression of the mutated putative *Schizochytrium als* gene.

The present inventors have produced three different transformation vectors containing mutant als genes: one mutant als gene encodes an enzyme with a valine at position 595 instead of a tryptophan (plasmid pMON50201, or ALSmut1-7), another encodes a glutamine at position 192 instead of a proline (plasmid pMON50202, or ALSmut2-2), and a third form contains both of these mutations (plasmid pMON50203, or ALSmut3-5). In these vectors, the expression of the recombinant mutant als genes is under the control of the native als gene promoter and terminator. The maps of these vectors, along with a vector containing the wild-type *Schizochytrium als* gene (plasmid pMON50200, or AE-5), are shown in FIGS. 3A-3D. Transformation of *Schizochytrium* with these mutant ALS-encoding vectors was confirmed by the use of the polymerase chain reaction and Southern blot analysis to detect the presence of vector sequences integrated into the *Schizochytrium* genome. As described in detail below, now that the present inventors have identified the complete sequence for the als gene, other mutations, specified below, can also be made. Therefore, the described mutant als genes are intended to be exemplary, and not inclusive of all possible mutations.

The transformation systems of the present invention have been used to introduce foreign genes into Thraustochytriales cells via cotransformation. In these cases, the foreign genes were placed between various *Schizochytrium* promoters and an appropriate terminator (e.g., SV40 or a *Schizochytrium* gene terminator region). For example, the present inventors have produced and introduced a synthetic gene that encodes an ω-3 fatty acid desaturase from the nematode *Caenorhabditis elegans*, represented herein by SEQ ID NO:29, to increase the levels of docosahexaenoic acid in *Schizochytrium*. SEQ ID NO:30 represents the amino acid sequence of the desaturase encoded by SEQ ID NO:29. Expression cassettes containing foreign genes can also be introduced into Thraustochytriales cells by direct inclusion within the selectable marker-containing transformation vector.

Moreover, the present inventors have also demonstrated with the mutant ALS-encoding vectors that homologous recombination occurs in *Schizochytrium*, indicating the feasibility of using recombinant means to inactivate or mutate specific native *Schizochytrium* genes.

With regard to the Thraustochytriales promoter sequences described herein, a sequence database search (GenBank) for all nucleotide and protein sequences reported for members of the order Thraustochytriales, indicates that as of the time of the present invention, no promoter sequences from *Schizochytrium* or any other member of Thraustochytriales have been reported. The only gene that has been reported from any *Schizochytrium* species is for the 5S ribosomal RNA of *S. aggregatum* (GenBank accession numbers X06104 and M13616). 5S and 18S ribosomal RNA sequences have been reported for the Thraustochytriales members, species *Ulkenia*, and genera *Labyrinthuloides* and *Thraustochytrium*, but this has no bearing on the present invention. A partial coding region of a "putative T3/T7-like RNA polymerase" gene from *Thraustochytrium aureum* has been described (*Nucleic Acids Research* 15:648-654, 1996), but a promoter sequence for this gene was not reported.

This invention can be used to introduce any genes or other nucleotide sequences that are of interest into a microorganism of the order Thraustochytriales. Such nucleotide sequences include, but are not limited to, nucleic acids encoding proteins (e.g., enzymes) associated with the synthesis of fatty acids (e.g, the fatty acids: docosahexaenoic acid (DHA), docosapentaenoic acid (DPA), eicosapentaenoic acid (EPA) and arachadonic acid (ARA). Such proteins include, but are not limited to: fatty acid synthases, fatty acid desaturases, and fatty acid elongases, as well as proteins associated with a polyketide synthase complex and/or proteins associated with incorporation of such fatty acids into phospholipids or into triacylglycerol molecules. For example, the invention has been used to introduce genes encoding various ω-3 fatty acid desaturases into Schizochytrium in an attempt to increase the level of docosahexaenoic acid (DHA) in the cells via ω-3 desaturation of docosapentaenoic acid (DPA). As another example, expression of a putative polyenoic fatty acid isomerase from the red alga, *Ptilota*, in *Schizochytrium* has also been demonstrated. The genes encoding a Schizochytrium polyketide synthase complex (i.e., a polyketide synthase system) have been deposited as GenBank Accession Nos. AF378329 (ORFA), AF378328 (ORFB) and AF378329 (ORFC).

The present invention is also useful for introducing into Thraustochytriales microorganisms genes and other nucleotide sequences encoding proteins associated with the isoprenoid biosynthetic pathway. Such proteins include, but are not limited to, HMG-CoA synthase and HMG-CoA reductase. Other suitable proteins include proteins associated with the synthesis of molecules derived from isoprenoid subunits including, but not limited to, various steroid compounds and various carotenoid compounds. Proteins associated with the synthesis of various carotenoid compounds include, but are not limited to, squalene synthase, phytoene synthase, phytoene desaturase, and various carotenoid cyclases, hydroxylases and ketolases.

The present invention is also useful for introducing into Thraustochytriales one or more nucleic acid sequences encoding proteins associated with the synthesis of anti-oxidant compounds including, but not limited to, vitamin E and lipoic acid.

In addition, the present invention can be used to introduce any genes or other nucleotide sequences vectors into Thraustochytriales microorganisms in order to inactivate or delete genes (i.e., "knock-out" or "targeted gene disruption"). The inactivation or deletion of genes is typically used for the purpose of enhancing the commercial value of the microorganism. For example, it may be desirable to remove genes that encode enzymes (or nucleic acids which regulate the expression of such genes) of the saturated and polyunsaturated fatty acid synthesis pathways. In another aspect, it may be desirable to inhibit or knock-out genes encoding proteins that are involved in the degradation of other valuable compounds produced by the Thraustochytriales microorganism or which otherwise lessen the value of the desired compound. For example, genes encoding lipases, fatty acid oxidation enzymes, and proteins that have objectionable flavors or odors may be desirable knock-out targets by the present invention. In yet another aspect, it may be desirable to knock-out genes encoding proteins that are associated with the synthesis of compounds whose synthesis is in competition with other molecules of interest. For example, such genes include, but are not limited to, genes encoding proteins involved in carbohydrate biosynthesis, genes encoding proteins involved in the synthesis of various products of isoprenoid pathways (e.g., sterols or specific carotenoid compounds), and genes encoding proteins involved in the synthesis of cell wall components. By way of example, genes have been introduced into *Schizochytrium* cells by the use of this invention in an attempt to inactivate genes that are homologous to the polyketide synthase genes from *Shewanella* in order to assess their role in the production of highly unsaturated fatty acids (HUFA). As exemplified by Example 6, the present invention can also be used to inactivate, delete, or mutate native genes that are involved in the production of fatty acids, carotenoids, sterols, vitamins, or other compounds in order to improve the economics or acceptability of products that are related to these compounds. It is noted that in some embodiments, as discussed above, it may be desirable to enhance production of a given protein, whereas in other embodiments, it may be desirable to inhibit production of the same protein. Such determinations are based on the given use and production goals for a specific microorganism. The present invention is also useful for determining the process of genetic recombination in *Schizochytrium*.

Other genes and nucleic acid molecules useful for introduction into Thraustochytriales will be apparent to those of skill in the art, and all such genes and molecules are intended to be encompassed by the present invention.

Various embodiments of the present invention are described below initially with regard to a Thraustochytriales als gene and/or ALS protein of the present invention. It is to be understood, however, that the general definitions of terms and methods are intended to apply to the discussion of other genes, nucleic acids and proteins described below.

The present invention is based in part on the identification, isolation and production of nucleic acid sequences encoding selectable markers that are suitable for use in recombinant constructs for the transformation of Thraustochytrid microorganisms. Such selectable markers allow the selection of microorganisms that have been successfully transformed with the recombinant constructs of the present invention. One selectable marker useful for the transformation of Thraustochytriales according to the present invention is a Thraustochytriales acetolactate synthase (i.e., ALS). Preferably, the acetolactate synthase has been modified, mutated, or otherwise selected, to be resistant to inhibition by sulfonylurea compounds, imidazolinone-class inhibitors and/or pyrimidinyl oxybenzoates (i.e., such an ALS is a homologue of a naturally occurring acetolactate synthase).

According to the present invention, an acetolactate synthase is a protein that has acetolactate synthase biological activity, including full-length proteins, fusion proteins, or any homologue of a naturally occurring acetolactate synthase. A homologue of an acetolactate synthase includes proteins which differ from a naturally occurring acetolactate synthase in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). Preferred homologues of a naturally occurring acetolactate synthase are described in detail below.

An isolated protein, such as an isolated acetolactate synthase, according to the present invention, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated acetolactate synthase of the present invention is produced recombinantly. A "Thraustochytriales acetolactate synthase" refers to an acetolactate synthase (including a homologue of a naturally occurring acetolactate synthase) from a Thraustochytriales microorganism or that has been otherwise produced from the knowledge of the structure (e.g., sequence) of a naturally occurring acetolactate synthase from a Thraustochytriales microorganism. In other words, a Thraustochytriales acetolactate synthase includes any acetolactate synthase that has the structure and function of a naturally occurring acetolactate synthase from a Thraustochytriales microorganism or that is a biologically active (i.e., has biological activity) homologue of a naturally occurring acetolactate synthase from a Thraustochytriales microorganism as described in detail herein. As such, a Thraustochytriales acetolactate synthase can include purified, partially purified, recombinant, mutated/modified and synthetic proteins.

In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). For example, a biological activity of an acetolactate synthase includes acetolactate synthase enzymatic activity. Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

With regard to the acetolactate synthase of the present invention, it is preferred that modifications present in acetolactate synthase homologues, as compared to a naturally occurring acetolactate synthase, do not substantially change, or at least do not substantially decrease, the basic biological activity of the synthase as compared to the naturally occurring protein. However, such homologues may have differences in characteristics other than the functional, or enzymatic, activity of the protein as compared to the naturally occurring form, such as a decreased sensitivity to inhibition by certain compounds as compared to the naturally occurring protein. Preferably, a homologue of a naturally occurring acetolactate synthase has reduced (i.e., decreased, lessened) sensitivity to compounds that bind to and inactivate naturally occurring acetolactate synthases as compared to the naturally occurring acetolactate synthase from which the homologue was derived. For example, sulfonylurea compounds, such as sulfometuron methyl (SMM), are often toxic to cells because they are able to bind to and inactivate acetolactate synthase (ALS). Imidazolinones, triazolopyrimidines, and other similar compounds (referred to generally herein as imidazolinone-class inhibitors) have also been shown to bind to and inactivate ALS. Therefore, a homologue of a naturally occurring acetolactate synthase preferably has reduced sensitivity to sulfonylurea compounds, as well as to imidazolinone-class inhibitors (e.g., by having disrupted binding sites for such inhibitors or binding sites with reduced affinity for the inhibitor) and to pyrimidinyl oxybenzoates, while maintaining acetolactate synthase enzymatic activity.

As used herein, a protein that has "acetolactate synthase biological activity" or that is referred to as an "acetolactate synthase" refers to a protein that catalyzes the first step in the biosynthesis of the amino acids valine, leucine, and isoleucine. More specifically, an isolated acetolactate synthase of the present invention, including full-length proteins, truncated proteins, fusion proteins and homologues, can be identified in a straight-forward manner by the proteins' ability to catalyze the synthesis of acetolactate from pyruvate. Acetolactate synthase biological activity can be evaluated by one of skill in the art by any suitable in vitro or in vivo assay for enzyme activity.

In one embodiment, an acetolactate synthase of the present invention has an amino acid sequence that is at least about 65% identical to an amino acid sequence of selected from the group of SEQ ID NO:15, SEQ ID NO:19, SEQ ID NO:22, SEQ ID NO:24, over at least about 600 amino acids of any of such sequences, wherein the protein is an acetolactate synthase (i.e., has acetolactate synthase biological activity). More preferably, an acetolactate synthase of the present invention has an amino acid sequence that is at least about 70% identical, and more preferably, at least about 75% identical, and even more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:15, SEQ ID NO:19, SEQ ID NO:22 or SEQ ID NO:24, over at least about 600 amino acids of any of SEQ ID NO:15, SEQ ID NO:19, SEQ ID NO:22 or SEQ ID NO:24, wherein the protein has acetolactate synthase biological activity.

In another embodiment, an acetolactate synthase of the present invention has an amino acid sequence that is at least about 75% identical to an amino acid sequence of selected from the group of SEQ ID NO:15, SEQ ID NO:19, SEQ ID NO:22, SEQ ID NO:24, over at least 95 amino acids of any of such sequences, wherein the protein is an acetolactate synthase (i.e., has acetolactate synthase biological activity). More preferably, an acetolactate synthase of the present invention has an amino acid sequence that is at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:15, SEQ ID NO:19, SEQ ID NO:22 or SEQ ID NO:24, over at least 95 amino acids of any of SEQ ID NO:15, SEQ ID NO:19, SEQ ID NO:22 or SEQ ID NO:24, wherein the protein has acetolactate synthase biological activity. Even more preferably, an acetolactate synthase of the present invention has an amino acid sequence that has any of the above-referenced percent identities to any of SEQ ID NO:15, SEQ ID NO:19, SEQ ID NO:22 or SEQ ID NO:24 over at least 100 amino acids, and more preferably 125, and more preferably 150, and more preferably 175, and more preferably 200, and more preferably 225, and more preferably 250, and more preferably 275, and more preferably 300, and more preferably 325, and more preferably 350, and more preferably 375, and more preferably 400, and more preferably 425, and more preferably 450, and more preferably 475, and more preferably 500, and more preferably 525, and more preferably 550, and more preferably 575 amino acids of any of SEQ ID NO:15, SEQ ID NO:19, SEQ ID NO:22 or SEQ ID NO:24, wherein the protein has acetolactate synthase biological activity.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
 Reward for match=1
 Penalty for mismatch=−2
 Open gap (5) and extension gap (2) penalties
 gap x_dropoff (50) expect (10) word size (11) filter (on)

For blastp, using 0 BLOSUM62 matrix:
 Open gap (11) and extension gap (1) penalties
 gap x_dropoff (50) expect (10) word size (3) filter (on).

An acetolactate synthase of the present invention can also include proteins having an amino acid sequence comprising at least 30 contiguous amino acid residues of any of SEQ ID NO:15, SEQ ID NO:19, SEQ ID NO:22 or SEQ ID NO:24, (i.e., 30 contiguous amino acid residues having 100% identity with 30 contiguous amino acids of any of SEQ ID NO:15, SEQ ID NO:19, SEQ ID NO:22 or SEQ ID NO:24). In a preferred embodiment, an acetolactate synthase of the present invention includes proteins having amino acid sequences comprising at least 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350, and more preferably, at least 400, and more preferably, at least 450, and more preferably, at least 500, and more preferably, at least 550, and more preferably, at least 600, and more preferably, at least 650, contiguous amino acid residues of any of SEQ ID NO:15, SEQ ID NO:19, SEQ ID NO:22 or SEQ ID NO:24. Such a protein has acetolactate synthase biological activity.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, an acetolactate synthase of the present invention, including an acetolactate synthase homologue, includes a protein having an amino acid sequence that is sufficiently similar to a naturally occurring acetolactate synthase amino acid sequence that a nucleic acid sequence encoding the homologue is capable of hybridizing under moderate, high, or very high stringency conditions (described below) to (i.e., with) a nucleic acid molecule encoding the naturally occurring acetolactate synthase (i.e., to the complement of the nucleic acid strand encoding the naturally occurring acetolactate synthase amino acid sequence). Preferably, an acetolactate synthase is encoded by a nucleic acid sequence that hybridizes under moderate, high or very high stringency conditions to the complement of a nucleic acid sequence that encodes a protein comprising an amino acid sequence represented by SEQ ID NO:15, SEQ ID NO:19, SEQ ID NO:22 or SEQ ID NO:24. Even more preferably, an acetolactate synthase of the present invention is encoded by a nucleic acid sequence that hybridizes under moderate, high or very high stringency conditions to the complement of nucleotides 1260-3314 of SEQ ID NO:15, nucleotides 1260-3314 of SEQ ID NO:18, nucleotides 1260-3314 of SEQ ID NO:21, or nucleotides 1260-3314 of SEQ ID NO:23. Such hybridization conditions are described in detail below. A nucleic acid sequence complement of nucleic acid sequence encoding an acetolactate synthase of the present invention refers to the nucleic acid sequence of the nucleic acid strand that is complementary to the strand which encodes the acetolactate synthase. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent' hybridization conditions with a nucleic acid sequence that encodes the amino acid sequence SEQ ID NO:15, SEQ ID NO:19, SEQ ID NO:22 or SEQ ID NO:24, and/or with the complement of the nucleic acid sequence that encodes any of such amino acid sequences. Methods to deduce a complementary sequence are known to those skilled in the art. It should be noted that since amino acid sequencing and nucleic acid sequencing technologies are not entirely error-free, the sequences presented herein, at best, represent apparent sequences of an acetolactate synthase of the present invention.

Acetolactate synthase homologues can be the result of natural allelic variation or natural mutation. Acetolactate synthase homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding an acetolactate synthase is a gene that occurs at essentially the same locus (or loci) in the genome as the gene which encodes an amino acid sequence SEQ ID NO:15, but which, due to natural variations caused by, for example, mutation orrecombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Acetolactate synthase proteins of the present invention also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of a membrane protein, or genes having signal sequences removed which are poorly tolerated in a particular recombinant host).

The minimum size of a protein and/or homologue of the present invention is a size sufficient to have acetolactate synthase biological activity. Preferably, a protein of the present invention is at least 30 amino acids long, and more preferably, at least about 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350, and more preferably, at least 400, and more preferably, at least 450, and more preferably, at least 500, and more preferably, at least 550, and more preferably, at least 600, and more preferably, at least 650, and more preferably, at least 684 amino acids long. There is no limit, other than a practical limit, on the maximum size of such a protein in that the protein can include a portion of an acetolactate synthase protein or a full-length acetolactate synthase, plus additional sequence (e.g., a fusion protein sequence), if desired.

The present invention also includes a fusion protein that includes an acetolactate synthase-containing domain (i.e., an amino acid sequence for an acetolactate synthase according to the present invention) attached to one or more fusion segments. Suitable fusion segments for use with the present invention include, but are not limited to, segments that can: enhance a protein's stability; provide other desirable biological activity; and/or assist with the purification of an acetolactate synthase (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the acetolactate synthase-containing domain of the protein and can be susceptible to cleavage in order to enable straight-forward recovery of an acetolactate synthase. Fusion proteins are preferably produced by culturing a recombinant cell transfected with a fusion nucleic acid molecule that encodes a protein including the fusion segment attached to either the carboxyl and/or amino terminal end of an acetolactate synthase-containing domain.

The present invention also includes a mimetic of an acetolactate synthase. As used herein, the term "mimetic" is used to refer to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Mimetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example.

Such mimetics can be designed, selected and/or otherwise identified using a variety of methods known in the art. Various methods of drug design, useful to design mimetics or other therapeutic compounds useful in the present invention are disclosed in Maulik et al., 1997, *Molecular Biotechnology:* *Therapeutic Applications and Strategies*, Wiley-Liss, Inc., which is incorporated herein by reference in its entirety. An acetolactate synthase mimetic can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

According to the present invention, acetolactate synthases can be derived from any Thraustochytriales microorganism, and particularly, from any *Schizochytrium* microorganism. In one embodiment, a preferred acetolactate synthase of the present invention has an amino acid sequence selected from the group of SEQ ID NO:15, SEQ ID NO:19, SEQ ID NO:22, SEQ ID NO:24. The protein having an amino acid sequence represented by SEQ ID NO:15 is a naturally occurring (i.e., wild type) acetolactate synthase from a Thraustochytriales microorganism, and specifically, is a *Schizochytrium* acetolactate synthase. The amino acid sequences represented by SEQ ID NO:19, SEQ ID NO:22, SEQ ID NO:24 are sequences that have been modified, such that the resulting enzymes have reduced sensitivity to sulfonylurea compounds, as well as to imidazolinone-class inhibitors and pyrimidinyl oxybenzoates, as compared to the naturally occurring protein represented by amino acid sequence SEQ ID NO:15. It is noted that the proteins represented by SEQ ID NO:19, SEQ ID NO:22 and SEQ ID NO:24 have acetolactate synthase biological activity. Acetolactate synthases with reduced sensitivity to sulfonylurea compounds, as well as to imidazolinone-class inhibitors and pyrimidinyl oxybenzoates are preferred acetolactate synthases of the present invention, because the nucleic acid sequences encoding such synthases can be used in recombinant vectors of the present invention as selectable markers.

Therefore, one embodiment of the present invention relates to a modified acetolactate synthase, including any homologue of any of SEQ ID NO:15, SEQ ID NO:19, SEQ ID NO:22 and SEQ ID NO:24, wherein the homologue has acetolactate synthase biological activity, and particularly, wherein the homologue has reduced sensitivity to sulfonylurea compounds, as well as to imidazolinone-class inhibitors and pyrimidinyl oxybenzoates, as compared to the naturally occurring protein represented by amino acid sequence SEQ ID NO:15. In one aspect, such acetolactate synthase homologues include proteins having an amino acid sequence that differs from SEQ ID NO:15 by an amino acid deletion, insertion, or substitution at one or more of the following positions: 116G, 117A, 192P, 200A, 251K, 358M, 383D, 592V, 595W, or 599F. These positions correspond to known ALS mutation sites in a yeast acetolactate synthase (i.e., 116G, 117A, 192P, 200A, 251K, 354M, 379D, 583V, 586W, and590F, respectively) (See Mazur and Falco, 1989, *Annu. Rev. Plant Physiol. Plant Mol. Biol.* 40:441-470, incorporated herein by reference in its entirety). Other possible mutation sites will be known to those in the art based on successful amino acid mutations in ALS from other organisms. The application of such sites to the corresponding sites in the Thraustochytriales ALS is encompassed by the present invention.

As discussed above, the present invention is based in part on the discovery and production of recombinant constructs for the transformation of Thraustochytrid microorganisms. Therefore, one embodiment of the present invention relates to an isolated nucleic acid molecule comprising a nucleic acid sequence that encodes a Thraustochytriales acetolactate synthase, and nucleic acid sequence fully complementary thereto. A nucleic acid molecule encoding an acetolactate synthase of the present invention includes a nucleic acid molecule encoding any of the acetolactate synthase proteins, including homologues, discussed above. More particularly, one embodiment of the present invention relates to an isolated nucleic acid molecule comprising a nucleic acid sequence encoding a protein having an amino acid sequence that is at least about 65% identical to an amino acid sequence of selected from the group of SEQ ID NO:15, SEQ ID NO:19, SEQ ID NO:22, SEQ ID NO:24, over at least about 600 amino acids of any of such sequences, wherein the protein is an acetolactate synthase (i.e., has acetolactate synthase biological activity). More preferably, an isolated nucleic acid molecule of the present invention has a nucleic acid sequence encoding an amino acid sequence that is at least about 70% identical, and more preferably, at least about 75% identical, and even more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:15, SEQ ID NO:19, SEQ ID NO:22 or SEQ ID NO:24, over at least about 600 amino acids of any of SEQ ID NO:15, SEQ ID NO:19, SEQ ID NO:22 or SEQ ID NO:24, wherein the protein has acetolactate synthase biological activity.

In another embodiment, an isolated nucleic acid molecule of the present invention has a nucleic acid sequence encoding an amino acid sequence that is at least about 75% identical to an amino acid sequence of selected from the group of SEQ ID NO:15, SEQ ID NO:19, SEQ ID NO:22, SEQ ID NO:24, over at least 95 amino acids of any of such sequences, wherein the protein is an acetolactate synthase (i.e., has acetolactate synthase biological activity). More preferably, an isolated nucleic acid molecule of the present invention has a nucleic acid sequence encoding an amino acid sequence that is at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:15, SEQ ID NO:19, SEQ ID NO:22 or SEQ ID NO:24, over at least 95 amino acids of any of SEQ ID NO:15, SEQ ID NO:19, SEQ ID NO:22 or SEQ ID NO:24, wherein the protein has acetolactate synthase biological activity.

In yet another embodiment, an isolated nucleic acid molecule of the present invention has a nucleic acid sequence encoding an amino acid sequence that has any of the above-referenced percent identities to any of SEQ ID NO:15, SEQ ID NO:19, SEQ ID NO:22 or SEQ ID NO:24 over at least 100 amino acids, and more preferably 125, and more preferably 150, and more preferably 175, and more preferably 200, and more preferably 225, and more preferably 250, and more preferably 275, and more preferably 300, and more preferably 325, and more preferably 350, and more preferably 375, and more preferably 400, and more preferably 425, and more preferably 450, and more preferably 475, and more preferably 500, and more preferably 525, and more preferably 550, and more preferably 575 amino acids of any of SEQ ID NO:15, SEQ ID NO:19, SEQ ID NO:22 or SEQ ID NO:24, wherein the protein has acetolactate synthase biological activity. Percent identity is determined using BLAST 2.0 Basic BLAST default parameters, as described above.

In one embodiment, nucleic acid molecules encoding an acetolactate synthase of the present invention include isolated nucleic acid molecules that hybridize under moderate stringency conditions, and even more preferably under high stringency conditions, and even more preferably under very high stringency conditions with the complement of a nucleic acid sequence encoding a naturally occurring acetolactate synthase. Preferably, an isolated nucleic acid molecule encoding an acetolactate synthase of the present invention comprises a nucleic acid sequence that hybridizes under moderate or high stringency conditions to the complement of a nucleic acid sequence that encodes a protein comprising an amino acid sequence represented by SEQ ID NO:15, SEQ ID NO:19, SEQ ID NO:22 or SEQ ID NO:24. In one embodiment, an isolated nucleic acid molecule comprises a nucleic acid sequence that hybridizes under moderate, high or very high stringency conditions to the complement of a nucleic acid sequence represented by nucleotides 1260-3314 of SEQ ID NO:14, nucleotides 1260-3314 of SEQ ID NO:18, nucleotides 1260-3314 of SEQ ID NO:21, or nucleotides 1260-3314 of SEQ ID NO:23.

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

In another embodiment, nucleic acid molecules encoding an acetolactate synthase of the present invention include isolated nucleic acid molecules comprising a nucleic acid sequence encoding a protein having an amino acid sequence comprising at least 30 contiguous amino acid residues of any of SEQ ID NO:15, SEQ ID NO:19, SEQ ID NO:22 or SEQ ID NO:24, (i.e., 30 contiguous amino acid residues having 100% identity with 30 contiguous amino acids of any of SEQ ID NO:15, SEQ ID NO:19, SEQ ID NO:22 or SEQ ID NO:24). In a preferred embodiment, an isolated nucleic acid molecule comprises a nucleic acid sequence encoding a protein having an amino acid sequence comprising at least 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350, and more preferably, at least 400, and more preferably, at least 450, and more preferably, at least 500, and more preferably, at least 550, and more preferably, at least 600, and more preferably, at least 650, contiguous amino acid residues of any of SEQ ID NO:15, SEQ ID NO:19, SEQ ID NO:22 or SEQ ID NO:24. Such a protein has acetolactate synthase biological activity. In one embodiment, an isolated nucleic acid molecule encoding an acetolactate synthase comprises a nucleic acid sequence having at least 60 contiguous nucleotides, and more preferably at least 150, and more preferably at least 225, and more preferably at least 300, and more preferably at least 345, and more preferably at least 390, and more preferably at least 450, and more preferably at least 525, and more preferably at least 600, and more preferably at least 750, and more preferably at least 900, and more preferably at least 1050, and more preferably at least 1200, and more preferably at least 1350, and more preferably at least 1500, and more preferably at least 1650, and more preferably at least 1800, and even more preferably at least 1950, contiguous nucleotides of nucleotides 1260-3314 of SEQ ID NO:15, nucleotides 1260-3314 of SEQ ID NO:18, nucleotides 1260-3314 of SEQ ID NO:21, or nucleotides 1260-3314 of SEQ ID NO:23.

Particularly preferred nucleic acid molecules of the present invention include nucleotides 1260-3314 of SEQ ID NO:14 (encodes SEQ ID NO:15), nucleotides 1260-3314 of SEQ ID NO:18 (encodes SEQ ID NO:19), nucleotides 1260-3314 of SEQ ID NO:21 (encodes SEQ ID NO:22), or nucleotides 1260-3314 of SEQ ID NO:23 (encodes SEQ ID NO:24), SEQ ID NO:14, SEQ ID NO:18, SEQ ID NO:21 or SEQ ID NO:23.

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene, such as an acetolactate synthase gene described herein. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., are heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on protein biological activity. Allelic variants and protein homologues (e.g., proteins encoded by nucleic acid homologues) have been discussed in detail above.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

Similarly, the minimum size of a nucleic acid molecule of the present invention is a size sufficient to encode a protein having the desired biological activity, or sufficient to form a probe or oligonucleotide primer that is capable of forming a stable hybrid with the complementary sequence of a nucleic acid molecule encoding the natural protein (e.g., under moderate, high or very high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence (e.g., an acetolactate synthase-encoding sequence) or a nucleic acid sequence encoding a full-length protein.

One embodiment of the present invention includes a recombinant vector to be used for transformation of a Thraustochytriales microorganism. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be delivered, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of the recombinant microorganism. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention contains at least one selectable marker for Thraustochytriales microorganisms according to the present invention, such as a nucleic acid sequence encoding a Thraustochytriales acetolactate synthase (natural protein or homologue) or a nucleic acid sequence encoding the ble gene (described below). As used herein, the phrase "recombinant nucleic acid molecule" is used primarily to refer to a recombinant vector into which has been ligated the nucleic acid sequence to be cloned, manipulated, transformed into the host cell (i.e., the insert).

Typically, a recombinant vector, and therefore a recombinant nucleic acid molecule, includes at least one nucleic acid molecule of the present invention operatively linked to one or more transcription control sequences. As used herein, the phrase "recombinant molecule" or "recombinant nucleic acid molecule" primarily refers to a nucleic acid molecule or nucleic acid sequence operatively linked to a transcription control sequence, but can be used interchangeably with the phrase "nucleic acid molecule", when such nucleic acid molecule is a recombinant molecule as discussed herein. According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in a microorganism of the order Thraustochytriales. The present inventors are believed to be the first to isolate and identify at least three of such promoters, described in detail elsewhere herein.

Preferred promoters include, but are not limited to, a Thraustochytriales acetolactate synthase promoter (represented herein by nucleotides 1-1259 of SEQ ID NO:14), a Thraustochytriales α-tublin promoter (represented herein by nucleotides 441-894 of SEQ ID NO:9, a promoter from a Thraustochytriales polyketide synthase (PKS) system (contained withing SEQ ID NO:34), and a Thraustochytriales fatty acid desaturase promoter (contained within SEQ ID NO:31; it is noted that the fatty acid desaturase promoter is referred to as a desaturase promoter in U.S. Provisional Application Ser. No. 60/284,116, supra.). The cloning and sequencing of the α-tublin promoter, the acetolactate synthase promoter, and the fatty acid desaturase promoter are described in the Examples section. In a preferred embodiment, the α-tublin promoter comprises the naturally occurring Thraustochytriales α-tublin promoter sequence (nucleotides 441-894 of SEQ ID NO:9), or a nucleic acid sequence that is at least 95% identical to nucleotides 441-894 of SEQ ID NO:9, wherein the promoter has at least basal α-tublin promoter transcriptional activity. Similarly, a preferred acetolactate synthase promoter comprises a nucleic acid sequence of the naturally occurring Thraustochytriales acetolactate synthase promoter (represented within nucleotides 1-1259 of SEQ ID NO:14), or a nucleic acid sequence that is at least 75%, and more preferably 80%, and more preferably 85%, and more preferably 90%, and more preferably 95% identical to nucleotides 1-1259 of SEQ ID NO:14, wherein the promoter as at least basal acetolactate synthase promoter transcriptional activity. A preferred PKS promoter comprises a nucleic acid sequence of a naturally occurring Thraustochytriales PKS promoter (represented within SEQ ID NO:34), or a nucleic acid sequence that is at least 75%, and more preferably 80%, and more preferably 85%, and more preferably 90%, and more preferably 95% identical to SEQ ID NO:34, wherein the promoter as at least basal PKS promoter transcriptional activity. Finally, a preferred fatty acid desaturase promoter comprises a nucleic acid sequence of the naturally occurring Thraustochytriales fatty acid desaturase promoter (represented within SEQ ID NO:31), or is contained within a nucleic acid sequence that is at least 75%, and more preferably 80%, and more preferably 85%, and more preferably 90%, and more preferably 95% identical to SEQ ID NO:31, wherein the promoter as at least basal fatty acid desaturase promoter transcriptional activity. Methods for determining percent identity have been previously described herein for the acetolactate synthase sequences, and are encompassed herein.

In one embodiment, a recombinant vector of the present invention is an expression vector. As used herein, the phrase "expression vector" is used to refer to a vector that is suitable for production of an encoded product (e.g., a protein of interest). In this embodiment, a nucleic acid sequence encoding the product to be produced is inserted into the recombinant vector to produce a recombinant nucleic acid molecule. The nucleic acid sequence encoding the protein to be produced is inserted into the vector in a manner that operatively links the nucleic acid sequence to regulatory sequences in the vector (e.g., a Thraustochytriales promoter of the present invention) which enable the transcription and translation of the nucleic acid sequence within the recombinant microorganism. The selectable markers of the present invention enable the selection of a recombinant microorganism into which a recombinant nucleic acid molecule of the present invention has successfully been introduced.

In another embodiment, a recombinant vector of the present invention is a targeting vector. As used herein, the phrase "targeting vector" is used to refer to a vector that is used to deliver a particular nucleic acid molecule into a recombinant cell, wherein the nucleic acid molecule is used to delete or inactivate an endogenous gene within the host cell (i.e., used for targeted gene disruption or knock-out technology). Such a vector may also be known in the art as a "knockout" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to bind to the target gene such that the target gene and the insert undergo homologous recombination, whereby the endogenous target gene is deleted, inactivated or attenuated (i.e., by at least a portion of the endogenous target gene being mutated or deleted).

In one embodiment, a preferred recombinant vector of the present invention is a recombinant vector that is suitable for use in a Thraustochytriales microorganism, and which includes a nucleic acid sequence encoding an acetolactate synthase molecule of the present invention. Preferably, the acetolactate synthase is modified as compared to the naturally occurring form (SEQ ID NO:15), such that the synthase confers onto a Thraustochytriales microorganism that has been transfected with the recombinant vector, a reduced sensitivity to sulfonurea compounds, imidazolinone-class inhibitors, and/or pyrimidinyl oxybenzoates.

Preferably, such a recombinant vector comprises a nucleic acid sequence encoding an acetolactate synthase protein comprising an amino acid sequence that differs from SEQ ID NO:15 by an amino acid deletion, insertion, or substitution at one or more of the following positions: 116G, 117A, 192P, 200A, 251K, 358M, 383D, 592V, 595W, or 599F. In one embodiment, such acetolactate synthase proteins have an amino acid sequence including, but not limited to: SEQ ID NO:19, SEQ ID NO:22 and SEQ ID NO:24. Preferably, such a recombinant vector comprises a nucleic acid sequence selected from: nucleotides 1260-3314 of SEQ ID NO:18, nucleotides 1260-3314 of SEQ ID NO:21, and nucleotides 1260-3314 of SEQ ID NO:23. In a particularly preferred embodiment, recombinant vectors containing ALS-encoding nucleic acid sequences that confer the desired resistance include SEQ ID NO:18, SEQ ID NO:21 and SEQ ID NO:23.

In one embodiment, a recombinant vector that is suitable for conferring onto a Thraustochytriales microorganism that has been transfected with the recombinant vector a reduced sensitivity to sulfonurea compounds, imidazolinone-class inhibitors, and/or pyrimidinyl oxybenzoates, comprises SEQ ID NO:15, which is the naturally occurring *Schizochytrium* acetolactate synthase sequence. In this embodiment, the recombinant vector is designed to overexpress the naturally occurring synthase, whereby such overexpression has the effect of conferring resistance to the specified compounds onto the microorganism. In this embodiment, it will be appreciated by one skilled in the art that use of recombinant DNA technologies can improve control of expression of transformed nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules to correspond to the codon usage of the host cell, and deletion of sequences that destabilize transcripts.

In one embodiment of the present invention, a recombinant vector suitable for use in the transformation of Thraustochytriales microorganisms contains the Sh ble gene from *Streptoalloteichus hindustanus* as a selectable marker (which encodes a "bleomycin-binding protein), in combination with a Thraustochytriales promoter as previously described herein. A preferred recombinant vector comprising the ble gene and a Thraustochytriales promoter includes, for example, the vector sequence represented by SEQ ID NO:8 or 9. The amino acid sequence of the *Streptoalloteichus hindustanus* bleomycin binding protein is represented herein as SEQ ID NO:10.

Recombinant nucleic acid molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed protein to be secreted from the cell that produces the protein. Suitable signal segments include a signal segment that is naturally associated with the protein to be expressed or any heterologous signal segment capable of directing the secretion of the protein according to the present invention. In another embodiment, a recombinant molecule of the present invention comprises a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

Having described various tools which are useful for transforming microorganisms of the order Thraustochytriales, one embodiment of the present invention relates to a method for transformation of cells of a microorganism of the Order Thraustochytriales. The method includes a first step of: (a) introducing into cells of a microorganism of the Order Thraustochytriales a recombinant nucleic acid molecule as described previously herein. The recombinant nucleic acid molecule comprises a nucleic acid sequence encoding an acetolactate synthase that confers onto said cells reduced sensitivity to compounds selected from the group consisting of: sulfonylurea compounds, imidazolinone-class inhibitors, and pyrimidinyl oxybenzoates. Such acetolactate synthases have been described in detail above and include acetolactate synthases having an amino acid sequence represented by SEQ ID NO:19, SEQ ID NO:22 and SEQ ID NO:24, as well as homologues of any of such sequences or SEQ ID NO:15 as discussed above. The method includes a second step of: (b) selecting cells that have been successfully transformed with the recombinant nucleic acid molecule by culturing the cells of (a) in a medium containing at least one compound that is inhibitory to untransformed cells, the compound being selected from the group consisting of: a sulfonylurea compound, an imidazolinone-class inhibitor, and pyrimidinyl oxybenzoates. Cells which grow in the presence of such compounds have been successfully transformed.

The recombinant nucleic acid molecule used in the present method comprises any of the recombinant vectors of the present invention previously described herein, and typically includes at least one nucleic acid sequence encoding a protein to be produced by the recombinant cell (i.e., comprising a recombinant expression vector), or a nucleic acid sequence useful for targeted deletion or inactivation of an endogenous gene in the recombinant cell (i.e., comprising a recombinant targeting vector).

In one embodiment, the recombinant nucleic acid molecule further comprises a nucleic acid sequence encoding a protein to be produced by the cell, wherein the nucleic acid sequence encoding the protein is operatively linked to a transcription control sequence. Proteins that may be desirable for production in a Thraustochytriales will be known to those of skill in the art, and all are intended to be encompassed by the present invention. Particularly preferred proteins include, but are not limited to, proteins associated with the synthesis of a fatty acid selected from the group consisting of docosahexaenoic acid (DHA), docosapentaenoic acid (DPA), eicosapentaenoic acid (EPA) and arachadonic acid (ARA). Such proteins include, for example, a fatty acid synthase, a fatty acid desaturase, a fatty acid elongase, a protein associated with a polyketide synthase complex and a protein associated with incorporation of fatty acids into phospholipids or into triacylglycerol molecules. In one aspect, the protein is an ω-3 fatty acid desaturase is encoded by a nucleic acid sequence SEQ ID NO:29. SEQ ID NO:30 represents the amino acid sequence of the desaturase. In another aspect, the protein is a polyenoic fatty acid isomerase. In one embodiment, proteins which can be produced in Thraustochytriales microorganisms using the present method include proteins associated with the isoprenoid biosynthetic pathways. Such proteins include, but are not limited to, HMG-CoA synthase, HMG-CoA reductase, squalene synthase, phytoene synthase, phytoene desaturase, a carotenoid cyclase, a carotenoid hyroxylase, a carotenoid ketolase. In yet another embodiment, proteins which can be produced in Thraustochytriales microorganisms using the present method include, but are not limited to, vitamin E and lipoic acid.

In one embodiment, the recombinant nucleic acid molecule useful in the method of the present invention includes a nucleic acid sequence that hybridizes with a target nucleic acid sequence in the microorganism such that a gene comprising the target nucleic acid sequence is mutated or inactivated by homologous recombination with the second nucleic acid sequence. Such a nucleic acid sequence can be homologous to genes that encode enzymes (or nucleic acids which regulate the expression of such genes) of the saturated and polyunsaturated fatty acid synthesis pathways, genes encoding proteins that are involved in the degradation of other valuable compounds produced by the Thraustochytriales microorganism or which otherwise lessen the value of the desired compound, or genes encoding proteins that are associated with the synthesis of compounds whose synthesis is in competition with other molecules of interest. For example, target nucleic acid sequences include, but are not limited to, sequences encoding lipases, fatty acid oxidation enzymes, proteins involved in carbohydrate synthesis, proteins involved in synthesis of products of isoprenoid pathways, proteins involved in synthesis of cell wall components, proteins involved in the saturated fatty acid synthesis pathways, proteins involved in the polyunsaturated fatty acid synthesis pathways, proteins associated with a polyketide synthase complex, and proteins associated with incorporation of fatty acids into phospholipids or triacylglycerol molecules.

In one embodiment of the present invention, the method for transformation of Thraustochytriales microorganisms includes a step of introducing into the cell at least one additional recombinant nucleic acid molecule comprising a nucleic acid sequence encoding a protein to be expressed, the nucleic acid sequence being operatively linked to a transcription control sequence. Alternatively, the additional recombinant nucleic acid molecule can include a second nucleic acid sequence that hybridizes with a target nucleic acid sequence in the microorganism such that a gene comprising the target nucleic acid sequence is mutated or inactivated by homologous recombination with the second nucleic acid sequence. In this manner, multiple proteins can be introduced into the cell, multiple genes can be inactivated, or combinations of the two are possible. The additional recombinant nucleic acid molecule can be introduced into the Thraustochytriales microorganism simultaneously with the first recombinant nucleic acid molecule (i.e., cotransformation), or as a subsequent transformation (e.g., for the purposes of "stacking" traits).

In one embodiment, the method further includes the step of introducing into the cell at least one additional recombinant nucleic acid molecule comprising a nucleic acid sequence encoding a bleomycin-binding protein. In this embodiment, the additional recombinant nucleic acid molecule is preferably introduced in a subsequent step, rather than as a cotransformation. Preferably, the recombinant nucleic acid molecule comprising a nucleic acid sequence encoding a bleomycin-binding protein further comprises a nucleic acid sequence encoding a second protein to be expressed by the cell, wherein the nucleic acid sequence encoding the second protein is operatively linked to a transcription control sequence. Alternatively, or in addition, the recombinant nucleic acid molecule comprising a nucleic acid sequence encoding a bleomycin-binding protein further comprises a second nucleic acid sequence that hybridizes with a target nucleic acid sequence in the microorganism such that a gene comprising the target nucleic acid sequence is mutated or inactivated by homologous recombination with the second nucleic acid sequence. In one embodiment, such a recombinant nucleic acid molecule comprises a nucleic acid sequence SEQ ID NO:9.

Suitable host cells to transform using the method of the present invention include, but are not limited to, any microorganism of the order Thraustochytriales. Host cells can be either untransformed cells or cells that are already transfected with at least one nucleic acid molecule. Preferred host cells for use in the present invention include microorganisms from a genus including, but not limited to: *Thraustochytrium, Labyrinthuloides, Japonochytrium*, and *Schizochytrium*. Preferred species within these genera include, but are not limited to: any *Schizochytrium* species, including *Schizochytrium aggregatum, Schizochytrium limacinum, Schizochytrium minutum*; any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Particularly preferred strains of Thraustochytriales include, but are not limited to: *Schizochytrium* sp. (S31)(ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207).

According to the present invention, the term "transformation" is used to refer to any method by which an exogenous nucleic acid molecule (i.e., a recombinant nucleic acid molecule) can be inserted into microbial cells, such Thraustochytriales microbial cells. In microbial systems, the term "transformation" is used to describe an inherited change due to the acquisition of exogenous nucleic acids by the microorganism and is essentially synonymous with the term "transfection". Suitable transformation techniques include, but are not limited to, particle bombardment, electroporation, microinjection, lipofection, adsorption, infection and protoplast fusion.

In one embodiment, a protein to be produced using a method of the present invention is produced by culturing a cell that expresses the protein (i.e., a recombinant Thraustochytriales microorganism) under conditions effective to produce the protein. In some instances, the protein may be recovered, and in others, the microorganism may be harvested in whole or as a lysate and used as a "biomass". In another embodiment, a target gene is deleted or inactivated by culturing a cell that has been transformed with a recombinant molecule comprising a targeting vector of the present invention under conditions effective to allow recombination within the cell, resulting in deletion or inactivation of a target gene.

A preferred cell to culture is a recombinant cell of the present invention. Effective culture conditions include, but are not limited to, effective media, bioreactor, temperature, pH and oxygen conditions that permit protein production and/or recombination. An effective medium refers to any medium in which a Thraustochytriales cell is typically cultured. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Culture conditions suitable for Thraustochytriales microorganisms are also described in U.S. Pat. No. 5,340,742, issued Aug. 23, 1994, to Barclay; incorporated herein by reference in its entirety. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the fermentation medium; be secreted into a space between two cellular membranes; or be retained on the outer surface of a cell membrane. The phrase "recovering the protein" refers to collecting the whole fermentation medium containing the protein and need not imply additional steps of separation or purification. Proteins produced by the method of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins produced by the method of the present invention are preferably retrieved in "substantially pure" form. As used herein, "substantially pure" refers to a purity that allows for the effective use of the protein as a commercial product.

Yet another embodiment of the present invention relates to a recombinant microorganism of the order Thraustochytriales, which has been transformed with a recombinant nucleic acid molecule comprising a nucleic acid sequence encoding an acetolactate synthase of the present invention. Preferably, the acetolactate synthase confers onto the microorganism reduced sensitivity to compounds selected from the group consisting of: sulfonylurea compounds, imidazolinone-class inhibitors, and pyrimidinyl oxybenzoates. Suitable recombinant nucleic acid molecules and sequences for use in transforming such a microorganism have been described in detail above. Such a microorganism can be further transformed with other recombinant nucleic acid molecules, including recombinant nucleic acid molecules comprising a ble gene selectable marker and Thraustochytriales transcription control sequences, as previously described herein. Recombinant Thraustochytriales microorganisms according to the present invention are described in the Examples section. According to the present invention, a recombinant Thraustochytriales microorganism of the present invention is genetically engineered to express a protein of interest (examples of such proteins are discussed above) using the recombinant vectors described herein, and/or is genetically engineered for a targeted deletion or inactivation of a target gene using the recombinant vectors described herein.

As used herein, a recombinant microorganism has a genome which is modified (i.e., mutated or changed) from its normal (i.e., wild-type or naturally occurring) form using recombinant technology. A recombinant microorganism according to the present invention can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism. As used herein, genetic modifications which result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications which result in an increase in gene expression or function can be referred to as amplification, overproduction, overexpression, activation, enhancement, addition, or up-regulation of a gene.

According to the present invention, a recombinant Thraustochytriales microorganism can be produced using any microorganism of the order Thraustochytriales. Preferred genera of Thraustochytriales include, but are not limited to: *Thraustochytrium*, *Labyrinthuloides*, *Japonochytrium*, and *Schizochytrium*. Preferred species within these genera include, but are not limited to: any *Schizochytrium* species, including *Schizochytrium aggregatum*, *Schizochytrium limacinum*; any *Thraustochytrium* species (including any former *Ulkenia* species such as *U. visurgensis*, *U. amoeboida*, *U. sarkariana*, *U. profunda*, *U. radiata*, *U. minuta* and *Ulkenia* sp. BP-5601), *Thraustochytrium striatum*, *Thraustochytrium aureum*, *Thraustochytrium roseum*; and any *Japonochytrium* species. Particularly preferred strains of Thraustochytriales include, but are not limited to: *Schizochytrium* sp. (S31)(ATCC 20888); *Schizochytrium* sp. (S8)(ATCC 20889); *Schizochytrium* sp. (LC-RM)(ATCC 18915); *Schizochytrium* sp. (SR21); *Schizochytrium aggregatum* (Goldstein et Belsky)(ATCC 28209); *Schizochytrium limacinum* (Honda et Yokochi)(IFO 32693); *Thraustochytrium* sp. (23B)(ATCC 20891); *Thraustochytrium striatum* (Schneider)(ATCC 24473); *Thraustochytrium aureum* (Goldstein)(ATCC 34304); *Thraustochytrium roseum* (Goldstein)(ATCC 28210); and *Japonochytrium* sp. (L1)(ATCC 28207).

The following examples are provided for the purpose of illustration and are not intended to limit the scope of the present invention.

EXAMPLES

Example 1

This example describes the production of recombinant plasmid pTUBZEO11-2.

Figure 1:
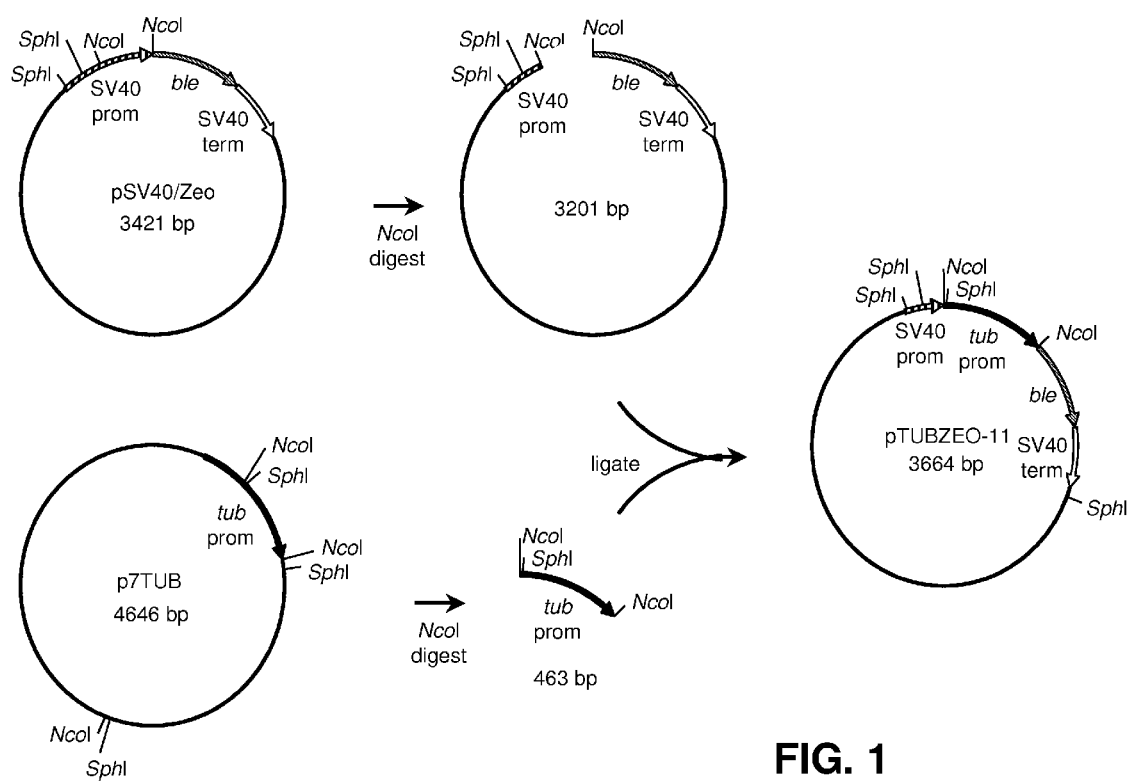
FIG. 1 illustrates the construction of recombinant plasmid pTUBZEO-11.

Construction of recombinant plasmid pTUBZEO11-2 is illustrated in FIGS. 1 and 2. This plasmid contains the ble gene from *Streptoalloteichus hindustanus* functionally coupled to an α-tublin gene promoter isolated from *Schizochytrium* sp. This plasmid was produced as follows. A cDNA clone (CGNE0002-001-B6) was isolated from a *Schizochytrium* sp. cDNA library and partially sequenced (SEQ ID NO:1) as part of a large-scale *Schizochytrium* cDNA sequencing project. The nucleotide sequence was determined to encode α-tublin by BLASTX homology searching (Gish, W. and D. States. 1993. *Nat. Genet.* 3:266-272). The amino acid sequence deduced from bases 116 through 550 is 93% identical to the first 145 amino acids of α-tublin from *Pelvetica fastigiata* (GenBank Accession No. U58642).

In order to isolate the promoter associated with this gene, genomic DNA was isolated from *Schizochytrium* sp. cells and processed by the use of a "GenomeWalker™" kit (Clontech Laboratories, Inc., Palo Alto, Calif.), which involves enzymatic digestion of genomic DNA with restriction endonucleases to generate blunt ends, followed by ligation of the digested DNA to specific double-stranded DNA adapter molecules provided in the kit. The DNA upstream of the α-tublin coding sequence was then amplified by the polymerase chain reaction (PCR), using the outer adapter primer (AP1) provided in the kit and the α-tublin-specific primer PGR20 (SEQ ID NO:2). Further amplification of the gene was carried out using the nested adapter primer (AP2) provided in the kit and a nested α-tublin-specific primer PGR19 (SEQ ID NO:3). The resulting PCR products were subcloned into plasmid pCR2.1-TOPO (Invitrogen Corp., Carlsbad, Calif.). One of the subcloned fragments was sequenced; the sequence of the 725 bp immediately preceding the α-tubulin gene start codon is given as SEQ ID NO:4.

Using oligonucleotide primers based on the DNA sequence obtained in this manner, PCR using Taq DNA polymerase (Perkin-Elmer Corp., Norwalk, Conn.) was used to generate a modified α-tublin promoter region in which an NcoI restriction site was incorporated into the 3' end of the DNA fragment; this NcoI site contained a start codon that was at the same position as in the α-tublin coding region. The primers used in this reaction were PGR33 (SEQ ID NO:5) and PGR34 (SEQ ID NO:6), and the template was genomic DNA isolated from *Schizochytrium* sp. cells. The following reaction conditions were utilized: 94° C. for 4 min; (94° C. for 1 min, 54° C. for 45 sec, 72° C. for 2 min)×30; 72° C. for 7 min. This fragment was cloned into plasmid pCR2.1-TOPO to form plasmid p7TUB (SEQ ID NO:7). Plasmid p7TUB was digested with NcoI, and a resulting 463-bp fragment containing the *Schizochytrium* α-tublin promoter region was isolated by agarose gel purification. Plasmid pSV40/Zeo (Invitrogen Corp., Carlsbad, Calif.), which contains the ble gene from *Streptoalloteichus hindustanus* flanked by an SV40 promoter and terminator, was also digested with NcoI to yield a 3201-bp and a 314-bp fragment. The 3201-bp fragment was agarose gel-purified and ligated to the 463-bp NcoI fragment from p7TUB to yield pTUBZEO-11 (SEQ ID NO:8), depicted in FIG. 1.

Next, plasmid pTUBZEO-11 was digested with SphI, and a resulting 1122-bp fragment that contained the ble gene flanked by the *Schizochytrium* α-tublin promoter and the SV40 terminator was agarose gel purified and ligated to plasmid pUC19 (Messing, J. 1983. *Meth. Enzymol.* 101:20) that had been linearized by digestion with SphI. The resulting plasmid was named pTUBZEO11-2 (SEQ ID NO:9) and is depicted in FIGS. 2 and 4. Plasmid pTUBZEO11-2 is also referred to as pMON50000. In SEQ ID NO:9, the *Schizochytrium* α-tublin promoter is contained withing nucleotides 441-894; the ble gene coding region is contained within nucleotides 895-1269; and the SV40 terminator is contained within nucleotides 1270-1524.

Example 2

This example describes the production of recombinant plasmids pMON50200, pMON50201, pMON50202, and pMON50203.

The native acetolactate synthase-encoding gene (als) from *Schizochytrium* sp. was isolated in the following manner. A cDNA clone (LIB81-028-Q1-E1-D9) was isolated from a *Schizochytrium* cDNA library and partially sequenced (SEQ ID NO:11) as part of a large-scale *Schizochytrium* sp. cDNA sequencing project. The nucleotide sequence was determined by BLASTX homology to encode acetolactate synthase; e.g., the amino acid sequence deduced from bases 154 through 378 was 68% identical with amino acids 313 through 387 of ALS from *Schizosaccharomyces pombe* (GenBank Accession No. P36620). The full-length sequence of this cloned cDNA was then obtained, which indicated that the cDNA clone did not contain the entire als coding region. In order to obtain the full-length als gene, a *Schizochytrium* genomic lambda library was probed using standard protocols (see e.g. Sambrook et. al., *Molecular Cloning: A Laboratory Manual*. Cold Spring Harbor Laboratory Press, 1989) with a 372-bp digoxygenin (DIG)-labeled DNA probe (referred to as the ALS2 probe). The ALS2 probe was generated via PCR using a nucleotide mix that included DIG-11-UTP (Boehringer Mannheim Biochemicals GmbH, Germany), using forward primer PGR38 (SEQ ID NO:12) andreverseprimerPGR39 (SEQ ID NO:13), which were based upon the sequence of cDNA clone LIB81-028-Q1-E1-D9. One of the genomic clones identified with the ALS2 probe, designated ALS-4A, was isolated and further characterized by Southern hybridization blots using the DIG-labeled ALS2 probe. A 4.9-kbp fragment from AhdI-digested ALS-4A lambda DNA was found to hybridize to the ALS2 probe. This fragment was isolated by agarose gel purification, treated with T4 DNA polymerase in order to generate blunt ends, and then ligated into SmaI-digested pBluescriptII KS+ (Stratagene Corp., La Jolla, Calif.) to form plasmid pMON50200 (depicted in FIG. 3-A). The sequence of pMON50200 is given as SEQ ID NO:14. The sequence of the acetolactate synthase enzyme encoded by the *Schizochytrium* als gene is given as SEQ ID NO:15.

Plasmids pMON50201, pMON50202, and pMON50203 (depicted in FIGS. 3-B, 3-C, and 3-D, respectively) were produced from plasmid pMON50200 by site-directed mutagenesis such that the encoded acetolactate synthase enzymes are no longer inhibited by certain compounds, including sulfometuron methyl (SMM). These plasmids were constructed as follows. The "Transformerä" site-directed mutagenesis kit (Clontech Laboratories, Inc., Palo Alto, Calif.) was used to introduce the following mutations into plasmid pMON502000 according to the manufacturer's instructions. An oligonucleotide selection primer, DM19 (SEQ ID NO:16), was used in all three constructions; this primer leads to the conversion of a unique EcoRV site in the multiple cloning site of pMON50200 to an AatII site. Primer DM14 (SEQ ID NO:17) was used to change amino acid residue number 595 in the encoded ALS enzyme from tryptophan to valine, while at the same time introducing an AclI site in the gene sequence; the resulting plasmid is referred to as pMON50201 (SEQ ID NO:18). Likewise, primer DM15 (SEQ ID NO:20) was used to change amino acid residue number 192 in the encoded ALS enzyme from a proline to a glutamine and to introduce a BsgI site in the als gene, resulting in plasmid pMON50202 (SEQ ID NO:21). To construct plasmid pMON50203 (SEQ ID NO:23), both DM14 and DM15 primers were used, resulting in an encoded ALS enzyme containing both of the amino acid residue replacements described above. The sequences of the mutant acetolactate synthase enzymes encoded by plasmids pMON50201, pMON50202, and pMON50203 are given as SEQ ID NO:19, SEQ ID NO:22, and SEQ ID NO:24, respectively.

Example 3

This example describes the genetic transformation of *Schizochytrium* sp. with the recombinant molecules described in Examples 1 and 2.

The strain used in this example in *Schizochytrium* sp. N230D, a derivative of American Type Culture Collection strain 20888 (ATCC, Manassas, Va.). For liquid cultures, cells were grown axenically in M50-3 medium at 30° C. with shaking at 200-300 rpm. M50-3 medium contains the following components: NaCl, 12.5 g; $MgSO_4.7H_2O$, 2.5 g; KCl, 0.5 g; $CaCl_2$, 0.05 g; glucose, 30 g; Na-glutamate, 3 g; $KH_2PO_4$, 0.4 g; yeast extract, 1 g; $NaHCO_3$, 0.4 g; $Na_2EDTA$, 30 mg; $FeCl_3*6H_2O$, 1.2 mg; $H_3BO_3$, 34.2 mg; $ZnSO_4.7H_2O$, 0.67 mg; $CoCl_2.6H_2O$, 0.13 mg; $NaMoO_4.2H_2O$, 25 µg; $CuSO_4*5H_2O$, 10 µg; $NiSO_4.6H_2O$, 0.26 mg; thiamine.HCl, 100 µg; biotin, 0.5 µg; cyanocobalamin, 0.5 µg, and deionized water (to one liter); final pH adjusted to 7.0. For growth on solid media, cells were grown at 30° C. on M50-3 medium or M1E-3 medium solidified by the addition of 1.5% (w/v) agar. M1E-3 medium contains the following components: glucose, 4 g; $(NH_4)_2SO_4$, 0.75 g; $Na_2SO_4$, 5 g; $MgSO_4.7H_2O$, 2 g; $KH_2PO_4$, 0.5 g; KCl, 0.5 g; $CaCl_2.2H_2O$, 0.1 g; MOPS buffer, 20.9 g; $FeSO_4.4H_2O$, 0.3 mg; $MnCl_2*4H_2O$, 0.1 mg; $ZnSO_4.7H_2O$; 80 µg; $CoCl_2.6H_2O$, 2 µg; $NaMoO_4.2H_2O$, 1 µg; $CuSO_4.5H_2O$, 60 µg; $NiSO_4.6H_2O$, 80 µg; thiamine.HCl, 320 µg; CA-pantothenate, 320 µg; cyanocobalamin, 8 µg, and deionized water (to one liter); final pH adjusted to 7.0.

The sensitivity of *Schizochytrium* sp. to Zeocin™ and SMM was determined by including these inhibitors in solidified M1E-3 medium at various concentrations and spreading cells on the plates at densities similar to those that are present during procedures used for selection of recombinant cells.

Genetic transformation of *Schizochytrium* cells was performed by particle bombardment (Sanford, J. C., F. D. Smith, and J. A. Russell. 1993. *Meth. Enzymol.* 217:483-509) using a Bio-Rad Biolistic PDS-1000/He Particle Delivery System (Bio-Rad Laboratories, Hercules, Calif.). *Schizochytrium* sp. N230D cells were grown in liquid M50-3 medium to an optical density at 680 nm ($OD_{680}$) of 0.4-0.8 (optical path length of 10 mm). An aliquot of cells corresponding to 1.0 $OD_{680}$ was briefly centrifuged, the supernatant solution was removed, and the pelleted cells were resuspended in 100 µl of sterile water. The resuspended cells were then spread in a 4 to 6 cm circle onto a Petri plate containing agar-solidified medium (e.g., M50-3 or M1E-3 medium) and allowed to sit for 30 to 60 min so that the excess water could be absorbed into the solid medium; this is referred to as the target plate.

A 1.5 mg aliquot of gold microcarriers (0.6µ nominal diameter, available from Bio-Rad Laboratories, Inc., Hercules, Calif.) was coated with 2.5 µg of transformation plasmid DNA (i.e., plasmid pTUBZEO 11-2, pMON50201, pMON50202, orpMON50203) as per the manufacturer's instructions (Biolistic® PDS-1000/He Particle Delivery System Instruction Manual; Bio-Rad Laboratories, Hercules, Calif.). The cells were bombarded with the DNA-coated gold microcarriers using the following conditions: 1100 psi burst disk, chamber vacuum of 25" Hg, microcarrier launch assembly placed on the top shelf and the target plates placed on the middle shelf, giving a burst disk-to-stopping screen distance of 1.5-2 cm and a stopping screen-to-target distance of approximately 7 cm. After bombardment, the cells were allowed to recover on the target plates for 4-6 hours at 30° C. The cells were then rinsed off the target plates with 1.5 ml sterile water, collected in a microfuge tube, centrifuged briefly, and resuspended in 400 µl sterile water. One hundred microliters of the suspension were spread onto each of four M1E-3 plates containing either 150-200 µg/ml Zeocin™ (Invitrogen Corp., Carlbad, Calif.) or 25 µg/mL SMM. Zeocin™-containing plates were used to select for cells that had been transformed with plasmid pTUBZEO11-2, whereas SMM-containing plates were used to select for cells that had been transformed with plasmids pMON50201, pMON50202, or pMON50203. The plates were then incubated for 7-10 days at 30° C. Colonies that appeared to be resistant to the selective agent were then patched onto fresh M1E-3 plates containing the same selective agent to confirm resistance. This protocol typically results in the generation of 100-1000 Zeocin™-resistant or SMM-resistant strains per bombardment.

Example 4

The following example demonstrates PCR analysis of transformed *Schizochytrium* cells.

PCR was used to confirm the presence of plasmid sequences in the putatively transformed strains that were resistant to the selective agents Zeocin™ or SMM. Template DNA from putative transformants and non-recombinant *Schizochytrium* N230D cells was obtained by using a single-use, plastic 1 µl inoculation loop to remove a small quantity of cells (1-2 mm$^3$) from resistant colonies that been patched onto agar plates (as described in Example 3). The cells were then resuspended in 15-20 µl of 1% Triton X-100 in a microfuge tube, placed in a boiling water bath for 10 minutes, and then centrifuged for 5 minutes at 14,000×g. Portions of these extracts (1-3 µL) were used to provide the template DNA for 25 µL PCR reactions using Taq DNA polymerase. To detect the presence of pTUBZEO 11-2 sequences in the *Schizochytrium* DNA, primers DM20 (SEQ ID NO:25) and DM21 (SEQ ID NO:26) were used; these primers anneal to the ble gene in plasmid pTUBZEO11-2 and amplify a 346-bp DNA fragment. The thermal profile used was as follows: 94° C. for 4 min; (94° C. for 45 sec, 52° C. for 45 sec, 72° C. for 2 min)×30; 72° C. for 7 min. To detect the presence of pMON50201, pMON50202, or pMON50203 sequences in the *Schizochytrium* DNA, primers BLA1 (SEQ ID NO:27) and BLA2 (SEQ ID NO:28) were used; these primers anneal to the bla (ampicillin-resistance) gene found in the vector backbone and amplify a 1229-bp DNA fragment. The thermal profile used was as follows: 94° C. for 4 min; (94° C. for 45 sec, 55° C. for 45 sec, 72° C. for 2 min)×30; 72° C. for 7 min. PCR products were analyzed by standard agarose gel electrophoresis, followed by staining with ethidium bromide.

The results of these analyses confirm that the vast majority of strains selected under these conditions are true transformants that contain plasmid DNA. No PCR products of the correct size were generated when using template DNA from control *Schizochytrium* sp. N230D cells that had not been bombarded with the transformation plasmids.

Example 5

The following example describes Southern blot analyses of transformed Schizochytrium cells.

Southern hybridization blots were conducted using DNA isolated from parental *Schizochytrium* N230D cells and several putative transformants in order to confirm the presence of transformation vector DNA sequences within the transformed cells. Southern blotting was conducted using techniques known to those skilled in the art (see e.g. Sambrook et. al., *Molecular Cloning: A Laboratory Manual*. Cold Spring Harbor Laboratory Press. 1989). DNA was isolated by the use of a "QIAamp" DNA purification kit (Qiagen Inc., Valencia, Calif.), digested with various restriction enzymes, separated by electrophoresis through agarose gels (0.8%-1.2% w/v), and then transferred to nylon membranes by alkaline capillary transfer.

Detection of vector DNA in cells transformed with pTUBZEO 11-2 was carried out by use of the "Genius" DIG-based system (Boehringer Mannheim Biochemicals GmbH, Germany), using as a hybridization probe a 346-bp DIG-labeled ble gene fragment generated via PCR with primers DM20 (SEQ ID NO:25) and DM21 (SEQ ID NO:26) and a nucleotide mix that included DIG-11-UTP. Pre-hybridization of the membrane was carried out at 68° C. for 1 h in the hybridization buffer supplied in the Genius kit. Hybridization was carried out at 68° C. for 18 h in hybridization buffer containing the ble gene probe that had been heat-denatured for 5 min at 94° C. The membranes were then washed twice for 5 min with 50 mL 2×SSC/0.1% SDS and twice for 15 min in 50 mL 0.1×SSC/0.1% SDS. Chemiluminescent detection of hybridizing DNA was performed as described in the Genius kit instructions.

DNA from non-transformed *Schizochytrium* N230D cells did not hybridize to the ble gene probe. Conversely, DNA from transformed cells did hybridize to the probe as follows:

SphI: SphI-digested DNA from transformed Schizochytrium cells contained a ~1100-bp DNA fragment that hybridized to the ble gene probe; this fragment, which is also observed in SphI-digested pTUBZEO11-2 DNA, represents the entire ble gene expression cassette (including the tubulin gene promoter and SV40 terminator).

XhoI: For each of the transformants tested, XhoI digestion of DNA resulted in hybridizing fragments larger than 15-20 kbp. XhoI does not cut within pTUBZEO11-2, and therefore these results indicate that pTUBZEO11-2 does not appear to exist as an extrachromosomal element in transformed cells, but rather becomes integrated into the *Schizochytrium* chromosome.

NcoI or HindIII: These enzymes both cut once within pTUBZEO11-2. Digestion of transformant DNA with either of these enzymes typically led to a prominent hybridizing fragment that comigrated with linearized pTUBZEO11-2 vector (i.e., ~3.8 kbp). This suggests that the vector can integrate in the chromosome in the form of tandem repeats.

Example 6

This example demonstrates homologous recombination in *Schizochytrium*.

The following experiments were conducted to demonstrate that homologous recombination can occur in *Schizochytrium* between endogenous native DNA sequences and homologous DNA sequences present in recombinant DNA molecules introduced into the cells. This type of homologous recombination can be very beneficial for producing recombinant strains with desirable properties. For example, homologous recombination can be used to inactivate endogenous genes by the targeted insertion of foreign genetic sequences. Additionally, homologous recombination can be used to replace an endogenous gene or portion thereof with an altered form of the gene such that the recombinant cells exhibit novel properties.

Homologous recombination was shown to occur in *Schizochytrium* cells transformed with plasmid pMON50202, which contains a mutation in the *Schizochytrium als* gene. This mutation introduces a BsgI site at bp position 571 of the als coding region. There is a naturally occurring BsgI site at bp position 1324 of the als coding region. Therefore, Southern blots of BsgI-digested Schizochytrium DNA can be used to discern the native als gene from the recombinant mutant als gene. For these experiments, an als-specific hybridization probe was produced via PCR using a nucleotide mix that included DIG-11-UTP (Boehringer Mannheim Biochemicals GmbH, Germany), forward primer PGR28 (SEQ ID NO:32), reverse primer PGR30 (SEQ ID NO:33), and a small amount of pMON50200 as the template. The resulting 323-bp DIG-labeled hybridization probe was referred to as ALS1.

DNA from non-recombinant *Schizochytrium* N230D cells was digested with BsgI and AhdI separately, subjected to agarose gel electrophoresis, transferred to a nylon membrane, and then probed with the ALS1 probe using procedures essentially the same as those described in Example 5. The ALS 1 probe labeled a 1.76-kbp fragment of BsgI-digested DNA and a 4.9-kbp fragment of AhdI-digested DNA.

Southern blots of BsgI- and AhdI-digested DNA from various recombinant strains that had been transformed with pMON50202 were also probed with the ALS1 probe. In some cases, the 1.76-kbp BsgI fragment was not present, and instead a 0.75-kbp fragment was labeled, corresponding to the 753-bp BsgI fragment present in pMON50202. A 4.9-kbp AhdI fragment was labeled in these recombinant strains, however, indicating that the recombinant, mutant als gene had recombined with the native als gene via double-crossover homologous recombination.

Single-crossover homologous recombination was also observed to occur in recombinant strains transformed with pMON50202. In these cases, both the 1.76-kbp and 0.75-kbp BsgI fragments were labeled in the Southern blots of DNA from the recombinant strains, but the 4.9-kbp AhdI fragment was replaced by larger labeled fragments, indicating that the entire pMON50202 vector had inserted into the native als gene, either as a single copy or as tandem repeats.

Additional evidence for homologous recombination in *Schizochytrium* was obtained by the introduction of recombinant DNA molecules containing a truncated, mutant als gene such that the incomplete ALS enzyme encoded by the truncated gene was nonfunctional. This truncated gene was produced by digesting pMON50202 with ClaI and HindHIII to yield a 2.8-kbp fragment, thereby removing the last 388 bp of the als coding sequence along with the als terminator region. This 2.8-kbp fragment was ligated into pBluescriptII KS+ (Stratagene Corp., La Jolla, Calif.) that had been digested with ClaI and HindIII, yielding plasmid pAR2. Plasmid pAR2 would only be expected to confer resistance to SMM in transformed *Schizochytrium* cells if a functional, mutant als gene was restored in transformed strains via homologous recombination between the native als gene and the truncated mutant als gene present in pAR2. This construct was introduced into *Schizochytrium* N230D cells by particle bombardment, and SMM-resistant strains were isolated as described in Example 3. Southern blot analysis of BsgI-digested DNA from the transformants, carried out as described earlier in this example, indicated that homologous recombination had clearly occurred in these strains; i.e., a 1.76-kbp BsgI fragment hybridized to the ALS1 probe in non-recombinant cells, but this was replaced by a 0.75-kbp hybridizing fragment in cells that had been transformed with pAR2.

Example 7

This example describes the use of transformation vector pTUBZEO11-2 or pMON50202 to produce via co-transformation strains that contain additional foreign DNA molecules that are not linked to a selectable marker gene.

Co-transformation was achieved by simultaneous introduction of pTUBZEO 11-2 and an additional plasmid containing any of several genes. The plasmids were co-precipitated on the gold particles as described in Example 3, using 2.5 µg of each plasmid. After the bombardment of target cells with the plasmid-coated gold particles, recombinant strains were selected on Zeocin™-containing agar plates as described in Example 1. The presence of the second, non-selected plasmid was then confirmed by PCR analysis or by Southern blot hybridization. Very high co-transformation frequencies (e.g., 50-90%) were typically achieved. For example, the plasmid pTR202, which contains the *Caenorhabditus elegans* fat-1 gene (Spychalla et al., 1997. *Proc. Natl. Acad. Sci. U.S.A.* 94, 1142-1147) linked to the *Schizochytrium* tubulin gene promoter and terminator, was introduced via the method provided in this example, and about 68% of the resulting Zeocin™-resistant strains were shown by PCR to contain the fat-1 gene (See Table 1). Similar results are observed when pMON50202 and an additional plasmid are co-introduced, followed by selection of transformed cells on SMM-containing solid medium. This co-transformation method can be used to introduce any foreign DNA desired.

TABLE 1

Efficiencies of co-transformation using the selectable marker plasmid pTubZeo11-2 and plasmids containing various fad genes. Zeocin$^R$-resistant transformants were screened for fad DNA sequences via PCR.

| Introduced fad Gene | #containing fad gene # Zeocin$^R$ strains tested | Co-transformation efficiency |
| --- | --- | --- |
| syn_fat1 | 17/25 | 68% |
| nat_fat1 | 24/25 | 96% |
| mut_fat1 | 21/25 | 84% |
| desB | 20/25 | 80% |

The transformation systems described in these examples represent a significant advance in the ability to genetically manipulate *Schizochytrium*, which is the most productive organism known for the fermentative production of lipid-based compounds. The availability of two independent transformation systems, along with the high co-transformation efficiencies that occur, should allow stacking of multiple traits in engineered strains. Furthermore, the apparent presence of homologous recombination in this microalga should allow the development of gene knockout procedures in order to identify the functions of unknown genes and to eliminate undesirable traits in production strains. The present inventors are currently using these systems to alter fatty acid metabolism in *Schizochytrium*, and are exploring possibilities for using this species and related microalgae (e.g., *Thraustochytrium*) for the production of carotenoids, sterols, and other lipoidal compounds.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule comprising a nucleic acid sequence selected from the group consisting of:
   (a) a nucleic acid sequence encoding a protein having an amino acid sequence that is at least 90% identical to an amino acid sequence selected from the group consisting of SEQ ID NO:15, SEQ ID NO:19, SEQ ID NO:22 and SEQ ID NO:24, wherein the protein is an acetolactate synthase; and
   (b) a nucleic acid sequence that is a full complement to the nucleic acid sequence of (a).

2. The isolated nucleic acid molecule of claim 1, wherein expression of the protein of (a) confers reduced sensitivity to compounds selected from the group consisting of: sulfonylurea compounds, imidazolinone-class inhibitors, and pyrimidinyl oxybenzoates, onto a microorganism of the Order Thraustochytriales that is transformed with the nucleic acid molecule.

3. The isolated nucleic acid molecule of claim 1, wherein the nucleic acid sequence encodes a *Schizochytrium* acetolactate synthase.

4. The isolated nucleic acid molecule of claim 1, wherein the nucleic acid encodes a *Schizochytrium* acetolactate synthase, and expression of the *Schizochytrium* acetolactate synthase confers reduced sensitivity to compounds selected from the group consisting of: sulfonylurea compounds, imidazolinone-class inhibitors, and pyrimidinyl oxybenzoates, onto a microorganism of the Order Thraustochytriales that is transformed with the nucleic acid molecule.

5. A recombinant nucleic acid molecule comprising the isolated nucleic acid molecule of claim 1, operatively linked to a transcription control sequence.

6. The recombinant nucleic acid molecule of claim 5, wherein the transcription control sequence is selected from the group consisting of a Thraustochytriales α-tubulin promoter, a Thraustochytriales acetolactate synthase promoter, a promoter from a Thraustochytriales polyketide synthase (PKS) system, and a Thraustochytriales fatty acid desaturase promoter.

7. The recombinant nucleic acid molecule of claim 6, wherein the Thraustochytriales acetolactate synthase promoter comprises nucleotides 1-1259 of SEQ ID NO:14.

8. The recombinant nucleic acid molecule of claim 6, wherein the Thraustochytriales α-tubulin promoter comprises nucleotides 441-894 of SEQ ID NO:9.

9. The recombinant nucleic acid molecule of claim 5, further comprising a signal sequence.

10. A recombinant microorganism of the order Thraustochytriales that is transformed with the recombinant nucleic acid molecule of claim 5.

11. A recombinant vector comprising the isolated nucleic acid molecule of claim 1.

12. The recombinant vector of claim 11, wherein the recombinant vector is an expression vector.

13. The recombinant vector of claim 11, wherein the recombinant vector is a targeting vector.

14. The recombinant vector of claim 11, further comprising a selectable marker.

15. The recombinant vector of claim 14, wherein the selectable marker is a nucleic acid sequence encoding a bleomycin-binding protein.

16. A recombinant vector for transformation of a microorganism of the Order Thraustochytriales, comprising a nucleic acid sequence encoding an acetolactate synthase that confers reduced sensitivity to compounds selected from the group consisting of: sulfonylurea compounds, imidazolinone-class inhibitors, and pyrimidinyl oxybenzoates, onto the microorganism of the order Thraustochytriales, wherein said acetolactate synthase has an amino acid sequence that is at least 90% identical to an amino acid sequence selected from the group consisting of SEQ ID NO:15, SEQ ID NO:19, SEQ ID NO:22 and SEQ ID NO:24; wherein the nucleic acid sequence encoding an acetolactate synthase is operatively linked to a transcription control sequence.

17. The recombinant vector of claim 16, wherein the transcription control sequence is selected from the group consisting of a Thraustochytriales α-tubulin promoter, a Thraustochytriales acetolactate synthase promoter, a promoter from a Thraustochytriales polyketide synthase (PKS) system, and a Thraustochytriales fatty acid desaturase promoter.

18. The recombinant vector of claim 17, wherein the Thraustochytriales acetolactate synthase promoter comprises nucleotides 1-1259 of SEQ ID NO:14.

19. The recombinant vector of claim 17, wherein the α-tubulin promoter comprises nucleotides 441-894 of SEQ ID NO:9.

20. The recombinant nucleic acid molecule of claim 16, further comprising a signal sequence.

21. The recombinant vector of claim 16, wherein the recombinant vector is an expression vector.

22. The recombinant vector of claim 16, wherein the recombinant vector is a targeting vector.

23. The recombinant vector of claim 16, further comprising a selectable marker.

24. The recombinant vector of claim 23, wherein the selectable marker is a nucleic acid sequence encoding a bleomycin-binding protein.

* * * * *

SEQUENCE LISTING

<160> NUMBER OF SEQ ID NOS: 35

<210> SEQ ID NO 1
<211> LENGTH: 551
<212> TYPE: DNA
<213> ORGANISM: Schizochytrium sp.
<220> FEATURE:
<221> NAME/KEY: misc_feature
<222> LOCATION: (520)..(520)
<223> OTHER INFORMATION: n = a, c, g, or t
<220> FEATURE:
<221> NAME/KEY: misc_feature
<222> LOCATION: (541)..(541)
<223> OTHER INFORMATION: n = a, c, g, or t

<400> SEQUENCE: 1

```
gtcgtgccta acaacacgcc gttctacccc gccttcttcg cgccccttcg cgtccaagca     60
tccttcaagt ttatctctct agttcaactt caagaagaac aacaccacca acaagatgcg    120
tgaggtcatc tccatccaca tcggccaggc cggtgttcag gtcggtaacg cctgctggga    180
gctctactgc ctcgagcatg gcatccagcc ggacggccag atgccctcgg acaagaccat    240
tggcggcggc gatgatgcct tcaacacctt cttctccgag actggcgccg gcaagcacgt    300
gccccgcgcc gtgctcgtcg atctcgagcc caccgtctgt gacgaggtcc gcaccggcac    360
ctaccgcgct ctttaccacc ccgagcagat catcaccggc aaggaggacg ctgccaacaa    420
ctacgctcgt ggccactaca ccatcggcaa ggagatcgtc gacctcgtcc tcgaccgcat    480
ccgcaagctc gccgacaact gcactggtct tcagggcttn ctctgcttca acgccgtcgg    540
nggtggtacc g                                                         551
```

<210> SEQ ID NO 2
<211> LENGTH: 27
<212> TYPE: DNA
<213> ORGANISM: Schizochytrium sp.

<400> SEQUENCE: 2

```
gcgccagtct cggagaagaa ggtgttg                                         27
```

<210> SEQ ID NO 3
<211> LENGTH: 27
<212> TYPE: DNA
<213> ORGANISM: Schizochytrium sp.

<400> SEQUENCE: 3

```
agctcccagc aggcgttacc gacctga                                         27
```

<210> SEQ ID NO 4
<211> LENGTH: 725
<212> TYPE: DNA
<213> ORGANISM: Schizochytrium sp.

<400> SEQUENCE: 4

```
gagacgtgct tcgcaagacc gctgtgctcg cgccgcacgc tctgtgtgtt acattaattt     60
ttttgtagat gaagtttctc tattctctcg aaattctgta gaatgttata gtctcttcac    120
tcccgtgatt ggagaggatt cttgcttgtt ccctcccgcc cgggtagcgc ttggagcaac    180
gcttgagcgc gcgctcgaaa gcggacggcg caacgagccg tttcacgccg cgctgtccaa    240
gtcccatttt tctccttacc ccatggccgt tgcatgccaa tttaggcccc ccactgacc    300
gaggtctgtc gataatccac ttttccattg atcttccagg tttcgttaac tcatgccact    360
```

| | |
|---|---|
| gagcaaaact tcggtctttc ctaacaaaag ctctcctcac aaagcatggc gcggcaacgg | 420 |
| acgtgtcctc atactccact gccacacaag gtcgataaac taagctcctc acaaatagag | 480 |
| gagaattcca ctgacaactg aaaacaatgt atgagacg atcaccactg gagcggcgcg | 540 |
| gcggttgggc gcggaggtcg gcagcaaaaa caagcgactc gccgagcaaa cccgaatcag | 600 |
| ccttcagacg tcgtgccta acaacacgcc gttctacccc gccttcttcg cgccccttcg | 660 |
| cgtccaagca tccttcaagt ttatctctct agttcaactt caagaagaac aacaccacca | 720 |
| acaag | 725 |

<210> SEQ ID NO 5
<211> LENGTH: 24
<212> TYPE: DNA
<213> ORGANISM: Schizochytrium sp.

<400> SEQUENCE: 5

| | |
|---|---|
| cacccatggt gttggtggtg ttgt | 24 |

<210> SEQ ID NO 6
<211> LENGTH: 24
<212> TYPE: DNA
<213> ORGANISM: Schizochytrium sp.

<400> SEQUENCE: 6

| | |
|---|---|
| aaactcgaga cgtgcttcgc aaga | 24 |

<210> SEQ ID NO 7
<211> LENGTH: 4646
<212> TYPE: DNA
<213> ORGANISM: Schizochytrium sp.

<400> SEQUENCE: 7

| | |
|---|---|
| aaactcgaga cgtgcttcgc aagaccgctg tgctcgcgcc gcacgctctg tgtgttacat | 60 |
| taattttttt gtagatgaag tttctctatt ctctcgaaat tctgtagaat gttatagtct | 120 |
| cttcactccc gtgattggag aggattcttg cttgttccct cccgcccggg tagcgcttgg | 180 |
| agcaacgctt gagcgcgcgc tcgaaagcgg acggcgcaac gagccgtttc acgccgcgct | 240 |
| gtccaagtcc catttttctc cttacccat ggccgttgca tgccaatttt aggcccccca | 300 |
| ctgaccgagg tctgtcgata atccactttt ccattgatct tccaggtttc gttaactcat | 360 |
| gccactgagc aaaacttcgg tctttcctaa caaaagctct cctcacaaag catgcgcgg | 420 |
| caacggacgt gtcctcatac tccactgcca cacaaggtcg ataaactaag ctcctcacaa | 480 |
| atagaggaga attccactga caactgaaaa caatgtatga gacgatca ccactggagc | 540 |
| ggcgcggcgg ttgggcgcgg aggtcggcag caaaaacaag cgactcgccg agcaaacccg | 600 |
| aatcagcctt cagacggtcg tgcctaacaa cacgccgttc taccccgcct tcttcgcgcc | 660 |
| ccttcgcgtc caagcatcct tcaagtttat ctctctagtt caacttcaag aagaacaaca | 720 |
| ccaccaacac catgggtgaa gggcgaattc tgcagatatc catcacactg gcggccgctc | 780 |
| gagcatgcat ctagagggcc caattcgccc tatagtgagt cgtattacaa ttcactggcc | 840 |
| gtcgttttac aacgtcgtga ctgggaaaac cctggcgtta cccaacttaa tcgccttgca | 900 |
| gcacatcccc ctttcgccag ctggcgtaat agcgaagagg cccgcaccga tcgcccttcc | 960 |
| caacagttgc gcagcctgaa tggcgaatgg gacgcgccct gtagcggcgc attaagcgcg | 1020 |
| gcgggtgtgg tggttacgcg cagcgtgacc gctacacttg ccagcgccct agcgcccgct | 1080 |

```
cctttcgctt tcttcccttc ctttctcgcc acgttcgccg gctttccccg tcaagctcta    1140
aatcggggc  tcccttttagg gttccgattt agagctttac ggcacctcga ccgcaaaaaa    1200
cttgatttgg gtgatggttc acgtagtggg ccatcgccct gatagacggt ttttcgccct    1260
ttgacgttgg agtccacgtt ctttaatagt ggactcttgt tccaaactgg aacaacactc    1320
aaccctatcg cggtctattc ttttgattta taagggattt tgccgatttc ggcctattgg    1380
ttaaaaaatg agctgattta acaaattcag ggcgcaaggg ctgctaaagg aaccggaaca    1440
cgtagaaagc cagtccgcag aaacggtgct gaccccggat gaatgtcagc tactgggcta    1500
tctggacaag ggaaaacgca agcgcaaaga gaaagcaggt agcttgcagt gggcttacat    1560
ggcgatagct agactgggcg gttttatgga cagcaagcga accggaattg ccagctgggg    1620
cgccctctgg taaggttggg aagccctgca agtaaactg  gatggctttc ttgccgccaa    1680
ggatctgatg gcgcagggga tcaagatctg atcaagagac aggatgagga tcgtttcgca    1740
tgattgaaca agatggattg cacgcaggtt ctccggccgc ttgggtggag aggctattcg    1800
gctatgactg ggcacaacag acaatcggct gctctgatgc cgccgtgttc cggctgtcag    1860
cgcaggggcg cccggttctt tttgtcaaga ccgacctgtc cggtgccctg aatgaactgc    1920
aggacgaggc agcgcggcta tcgtggctgg ccacgacggg cgttccttgc gcagctgtgc    1980
tcgacgttgt cactgaagcg ggaagggact ggctgctatt gggcgaagtg ccggggcagg    2040
atctcctgtc atctcgcctt gctcctgccg agaaagtatc catcatggct gatgcaatgc    2100
ggcggctgca tacgcttgat ccggctacct gcccattcga ccaccaagcg aaacatcgca    2160
tcgagcgagc acgtactcgg atggaagccg gtcttgtcga tcaggatgat ctggacgaag    2220
agcatcaggg gctcgcgcca gccgaactgt tcgccaggct caaggcgcgc atgcccgacg    2280
gcgaggatct cgtcgtgatc catggcgatg cctgcttgcc gaatatcatg gtggaaaatg    2340
gccgcttttc tggattcaac gactgtggcc ggctgggtgt ggcggaccgc tatcaggaca    2400
tagcgttgga tacccgtgat attgctgaag agcttggcgg cgaatgggct gaccgcttcc    2460
tcgtgcttta cggtatcgcc gctcccgatt cgcagcgcat cgccttctat cgccttcttg    2520
acgagttctt ctgaattgaa aaaggaagag tatgagtatt caacatttcc gtgtcgccct    2580
tattcccttt tttgcggcat tttgccttcc tgtttttgct cacccagaaa cgctggtgaa    2640
agtaaaagat gctgaagatc agttgggtgc acagtgggt  tacatcgaac tggatctcaa    2700
cagcggtaag atccttgaga gttttcgccc cgaagaacgt tttccaatga tgagcacttt    2760
taaagttctg ctatgtcata cactattatc ccgtattgac gccgggcaag agcaactcgg    2820
tcgccgggcg cggtattctc agaatgactt ggttgagtac tcaccagtca cagaaaagca    2880
tcttacggat ggcatgacag taagagaatt atgcagtgct gccataacca tgagtgataa    2940
cactgcggcc aacttacttc tgacaacgat cggaggaccg aaggagctaa ccgcttttt    3000
gcacaacatg ggggatcatg taactcgcct tgatcgttgg gaaccggagc tgaatgaagc    3060
cataccaaac gacgagagtg acaccacgat gcctgtagca atgccaacaa cgttgcgcaa    3120
actattaact ggcgaactac ttactctagc ttcccggcaa caattaatag actggatgga    3180
ggcggataaa gttgcaggac cacttctgcg ctcggccctt ccggctggct ggtttattgc    3240
tgataaatct ggagccggtg agcgtgggtc tcgcggtatc attgcagcac tggggccaga    3300
tggtaagccc tcccgtatcg tagttatcta cacgacgggg agtcaggcaa ctatggatga    3360
acgaaataga cagatcgctg agataggtgc ctcactgatt aagcattggt aactgtcaga    3420
ccaagtttac tcatatatac tttagattga tttaaaactt catttttaat ttaaaaggat    3480
```

-continued

```
ctaggtgaag atccttttg ataatctcat gaccaaaatc ccttaacgtg agttttcgtt    3540
ccactgagcg tcagaccccg tagaaaagat caaaggatct tcttgagatc ctttttttct    3600
gcgcgtaatc tgctgcttgc aaacaaaaaa accaccgcta ccagcggtgg tttgtttgcc    3660
ggatcaagag ctaccaactc ttttccgaa ggtaactggc ttcagcagag cgcagatacc    3720
aaatactgtc cttctagtgt agccgtagtt aggccaccac ttcaagaact ctgtagcacc    3780
gcctacatac ctcgctctgc taatcctgtt accagtggct gctgccagtg gcgataagtc    3840
gtgtcttacc gggttggact caagacgata gttaccggat aaggcgcagc ggtcgggctg    3900 aacgggggt tcgtgcacac agcccagctt ggagcgaacg acctacaccg aactgagata    3960
cctacagcgt gagcattgag aaagcgccac gcttcccgaa gggagaaagg cggacaggta    4020
tccggtaagc ggcagggtcg aacaggaga gcgcacgagg gagcttccag ggggaaacgc    4080
ctggtatctt tatagtcctg tcgggtttcg ccacctctga cttgagcgtc gatttttgtg    4140
atgctcgtca ggggggcgga gcctatggaa aaacgccagc aacgcggcct ttttacggtt    4200
cctggccttt tgctggcctt tgctcacat gttctttcct gcgttatccc ctgattctgt    4260
ggataaccgt attaccgcct tgagtgagc tgataccgct cgccgcagcc gaacgaccga    4320
gcgcagcgag tcagtgagcg aggaagcgga agagcgccca atacgcaaac cgcctctccc    4380
cgcgcgttgg ccgattcatt aatgcagctg gcacgacagg tttcccgact ggaaagcggg    4440
cagtgagcgc aacgcaatta atgtgagtta gctcactcat taggcacccc aggctttaca    4500
ctttatgctt ccggctcgta tgttgtgtgg aattgtgagc ggataacaat ttcacacagg    4560
aaacagctat gaccatgatt acgccaagct tggtaccgag ctcggatcca ctagtaacgg    4620
ccgccagtgt gctggaattc gccctt                                        4646

<210> SEQ ID NO 8
<211> LENGTH: 3664
<212> TYPE: DNA
<213> ORGANISM: Schizochytrium sp.

<400> SEQUENCE: 8
ccatggccgt tgcatgccaa ttttaggccc cccactgacc gaggtctgtc gataatccac      60
ttttccattg atcttccagg tttcgttaac tcatgccact gagcaaaact tcggtctttc    120
ctaacaaaag ctctcctcac aaagcatggc gcggcaacgg acgtgtcctc atactccact    180
gccacacaag gtcgataaac taagctcctc acaaatagag gagaattcca ctgacaactg    240
aaaacaatgt atgagagacg atcaccactg gagcggcgcg gcggttgggc gcggaggtcg    300
gcagcaaaaa caagcgactc gccgagcaaa cccgaatcag ccttcagacg gtcgtgccta    360
acaacacgcc gttctacccc gccttcttcg cgccccttcg cgtccaagca tccttcaagt    420
ttatctctct agttcaactt caagaagaac aacaccacca acaccatggc caagttgacc    480
agtgccgttc cggtgctcac cgcgcgcgac gtcgccggag cggtcgagtt ctggaccgac    540
cggctcgggt tctcccggga cttcgtggag gacgacttcg ccggtgtggt ccgggacgac    600
gtgaccctgt tcatcagcgc ggtccaggac caggtggtgc cggacaacac cctggcctgg    660
gtgtgggtgc gcggcctgga cgagctgtac gccgagtggt cggaggtcgt gtccacgaac    720
ttccgggacg cctccgggcc ggccatgacc gagatcggcg agcagccgtg ggggcgggag    780
ttcgccctgc gcgacccggc cggcaactgc gtgcacttcg tggccgagga gcaggactga    840
cacgtgctac gagatttcga ttccaccgcc gccttctatg aaaggttggg cttcggaatc    900
```

```
gttttccggg acgccggctg gatgatcctc cagcgcgggg atctcatgct ggagttcttc      960
gcccacccca acttgtttat tgcagcttat aatggttaca aataaagcaa tagcatcaca     1020
aatttcacaa ataaagcatt tttttcactg cattctagtt gtggtttgtc caaactcatc     1080
aatgtatctt atcatgtctg aattcccggg gatcctctag agtcgacctg caggcatgca     1140
agcttggcac tggccgtcgt tttacaacgt cgtgactggg aaaaccctgg cgttacccaa     1200
cttaatcgcc ttgcagcaca tccccctttc gccagctggc gtaatagcga agaggcccgc     1260
accgatcgcc cttcccaaca gttgcgcagc ctgaatggcg aatggcgcct gatgcggtat     1320
tttctcctta cgcatctgtg cggtatttca caccgcatat atggtgcact ctcagtacaa     1380
tctgctctga tgccgcatag ttaagccagc cccgacaccc gccaacaccc gctgacgcgc     1440
cctgacgggc ttgtctgctc ccggcatccg cttacagaca agctgtgacc gtctccggga     1500
gctgcatgtg tcagaggttt tcaccgtcat caccgaaacg cgcgagacga agggcctcg      1560 tgatacgcct atttttatag gttaatgtca tgataataat ggtttcttag acgtcaggtg     1620
gcacttttcg gggaaatgtg cgcggaaccc ctatttgttt attttttctaa atacattcaa    1680 atatgtatcc gctcatgaga caataaccct gataaatgct tcaataatat tgaaaaagga    1740
agagtatgag tattcaacat ttccgtgtcg cccttattcc cttttttgcg cattttgcc     1800 ttcctgtttt tgctcaccca gaaacgctgg tgaaagtaaa agatgctgaa gatcagttgg     1860
gtgcacgagt gggttacatc gaactggatc tcaacagcgg taagatcctt gagagttttc    1920
gccccgaaga acgttttcca atgatgagca cttttaaagt tctgctatgt ggcgcggtat     1980
tatcccgtat tgacgccggg caagagcaac tcggtcgccg catacactat tctcagaatg    2040
acttggttga gtactcacca gtcacagaaa agcatcttac ggatggcatg acagtaagag    2100
aattatgcag tgctgccata accatgagtg ataacactgc ggccaactta cttctgacaa    2160
cgatcggagg accgaaggag ctaaccgctt ttttgcacaa catgggggat catgtaactc     2220
gccttgatcg ttgggaaccg gagctgaatg aagccatacc aaacgacgag cgtgacacca    2280
cgatgcctgt agcaatggca acaacgttgc gcaaactatt aactggcgaa ctacttactc    2340
tagcttcccg gcaacaatta atagactgga tggaggcgga taaagttgca ggaccacttc    2400
tgcgctcggc ccttccggct ggctggttta ttgctgataa atctggagcc ggtgagcgtg    2460
ggtctcgcgg tatcattgca gcactggggc cagatggtaa gccctcccgt atcgtagtta    2520
tctacacgac ggggagtcag gcaactatgg atgaacgaaa tagacagatc gctgagatag    2580
gtgcctcact gattaagcat tggtaactgt cagaccaagt ttactcatat atactttaga    2640
ttgatttaaa acttcatttt taatttaaaa ggatctaggt gaagatcctt tttgataatc    2700
tcatgaccaa aatcccttaa cgtgagtttt cgttccactg agcgtcagac cccgtagaaa    2760
agatcaaagg atcttcttga gatccttttt ttctgcgcgt aatctgctgc ttgcaaacaa    2820
aaaaaccacc gctaccagcg gtggtttgtt tgccggatca agagctacca actctttttc    2880
cgaaggtaac tggcttcagc agagcgcaga taccaaatac tgtccttcta gtgtagccgt    2940
agttaggcca ccacttcaag aactctgtag caccgcctac atacctcgct ctgctaatcc    3000
tgttaccagt ggctgctgcc agtggcgata agtcgtgtct taccgggttg gactcaagac    3060
gatagttacc ggataaggcg cagcggtcgg gctgaacggg gggttcgtgc acacagccca    3120
gcttggagcg aacgacctac accgaactga gatacctaca gcgtgagcat tgagaaagcg    3180
ccacgcttcc cgaagggaga aaggcggaca ggtatccggt aagcggcagg gtcggaacag    3240
gagagcgcac gagggagctt ccagggggaa acgcctggta tctttatagt cctgtcgggt    3300
```

-continued

```
ttcgccacct ctgacttgag cgtcgatttt tgtgatgctc gtcagggggg cggagcctat      3360
ggaaaaacgc cagcaacgcg gccttttac ggttcctggc cttttgctgg cctttgtgctc      3420 acatgtgtgc tgggcccagc cggccagatc tgagctcgcg gccgcgatat cgctagctcg      3480
aggcaggcag aagtatgcaa agcatgcatc tcaattagtc agcaaccagg tgtggaaagt      3540
ccccaggctc cccagcaggc agaagtatgc aaagcatgca tctcaattag tcagcaacca      3600
tagtcccgcc cctaactccg cccatcccgc cctaactcc gcccagttcc gcccattctc       3660
cgcc                                                                    3664
```

<210> SEQ ID NO 9
<211> LENGTH: 3808
<212> TYPE: DNA
<213> ORGANISM: Artificial Sequence
<220> FEATURE:
<223> OTHER INFORMATION: Schizochytrium sp. and Streptoalloteichus
      hindustanus
<220> FEATURE:
<221> NAME/KEY: promoter
<222> LOCATION: (441)..(894)
<223> OTHER INFORMATION:
<220> FEATURE:
<221> NAME/KEY: CDS
<222> LOCATION: (895)..(1269)
<223> OTHER INFORMATION:
<220> FEATURE:
<221> NAME/KEY: terminator
<222> LOCATION: (1270)..(1524)
<223> OTHER INFORMATION:

<400> SEQUENCE: 9

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacctgcag gcatgccaat tttaggcccc ccactgaccg aggtctgtcg     480
ataatccact tttccattga ttttccaggt ttcgttaact catgccactg agcaaaactt     540
cggtctttcc taacaaaagc tctcctcaca agcatggcgc ggcaacgga cgtgtcctca     600 tactccactg ccacacaagg tcgataaact aagctcctca caaatagagg agaattccac     660
tgacaactga aaacaatgta tgagagacga tcaccactgg agcggcgcgg cggttgggcg     720
cggaggtcgg cagcaaaaac aagcgactcg ccgagcaaac ccgaatcagc cttcagacgg     780
tcgtgcctaa caacacgccg ttctaccccg ccttcttcgc gccccttcgc gtccaagcat     840
ccttcaagtt tatctctcta gttcaacttc aagaagaaca acaccaccaa cacc atg      897
                                                                     Met
                                                                       1 gcc aag ttg acc agt gcc gtt ccg gtg ctc acc gcg cgc gac gtc gcc      945
Ala Lys Leu Thr Ser Ala Val Pro Val Leu Thr Ala Arg Asp Val Ala
            5                  10                  15 gga gcg gtc gag ttc tgg acc gac cgg ctc ggg ttc tcc cgg gac ttc      993
Gly Ala Val Glu Phe Trp Thr Asp Arg Leu Gly Phe Ser Arg Asp Phe
        20                  25                  30 gtg gag gac gac ttc gcc ggt gtg gtc cgg gac gac gtg acc ctg ttc     1041
```

```
Val Glu Asp Asp Phe Ala Gly Val Val Arg Asp Asp Val Thr Leu Phe
         35                  40                  45 atc agc gcg gtc cag gac cag gtg gtg ccg gac aac acc ctg gcc tgg    1089
Ile Ser Ala Val Gln Asp Gln Val Val Pro Asp Asn Thr Leu Ala Trp
 50                  55                  60                  65 gtg tgg gtg cgc ggc ctg gac gag ctg tac gcc gag tgg tcg gag gtc    1137
Val Trp Val Arg Gly Leu Asp Glu Leu Tyr Ala Glu Trp Ser Glu Val
                 70                  75                  80 gtg tcc acg aac ttc cgg gac gcc tcc ggg ccg gcc atg acc gag atc    1185
Val Ser Thr Asn Phe Arg Asp Ala Ser Gly Pro Ala Met Thr Glu Ile
             85                  90                  95 ggc gag cag ccg tgg ggg cgg gag ttc gcc ctg cgc gac ccg gcc ggc    1233
Gly Glu Gln Pro Trp Gly Arg Glu Phe Ala Leu Arg Asp Pro Ala Gly
         100                 105                 110 aac tgc gtg cac ttc gtg gcc gag gag cag gac tga cacgtgctac         1279
Asn Cys Val His Phe Val Ala Glu Glu Gln Asp
         115                 120 gagatttcga ttccaccgcc gccttctatg aaaggttggg cttcggaatc gttttccggg  1339
acgccggctg gatgatcctc cagcgcgggg atctcatgct ggagttcttc gcccacccca  1399
acttgtttat tgcagcttat aatggttaca aataaagcaa tagcatcaca aatttcacaa  1459
ataaagcatt ttttcactg cattctagtt gtggtttgtc caaactcatc aatgtatctt   1519
atcatgtctg aattcccggg gatcctctag agtcgacctg caggcatgca agcttggcgt  1579
aatcatggtc atagctgttt cctgtgtgaa attgttatcc gctcacaatt ccacacaaca  1639
tacgagccgg aagcataaag tgtaaagcct ggggtgccta atgagtgagc taactcacat  1699
taattgcgtt gcgctcactg cccgctttcc agtcgggaaa cctgtcgtgc cagctgcatt  1759
aatgaatcgg ccaacgcgcg gggagaggcg gtttgcgtat tgggcgctct tccgcttcct  1819
cgctcactga ctcgctgcgc tcggtcgttc ggctgcggcg agcggtatca gctcactcaa  1879
aggcggtaat acggttatcc acagaatcag gggataacgc aggaaagaac atgtgagcaa  1939
aaggccagca aaaggccagg aaccgtaaaa aggccgcgtt gctggcgttt ttccataggc  1999 tccgccccc tgacgagcat cacaaaaatc gacgctcaag tcagaggtgg cgaaacccga   2059
caggactata aagataccag gcgtttcccc ctggaagctc cctcgtgcgc tctcctgttc   2119 cgacccctgcc gcttaccgga tacctgtccg ccttctctcc ttcgggaagc gtggcgcttt  2179
ctcaatgctc acgctgtagg tatctcagtt cggtgtaggt cgttcgctcc aagctgggct  2239
gtgtgcacga acccccccgtt cagcccgacc gctgcgcctt atccggtaac tatcgtcttg  2299
agtccaaccc ggtaagacac gacttatcgc cactggcagc agccactggt aacaggatta  2359
gcagagcgag gtatgtaggc ggtgctacag agttcttgaa gtggtggcct aactacggct   2419
acactagaag gacagtattt ggtatctgcg ctctgctgaa gccagttacc ttcggaaaaa   2479
gagttggtag ctcttgatcc ggcaaacaaa ccaccgctgg tagcggtggt ttttttgttt   2539
gcaagcagca gattacgcgc agaaaaaaag gatctcaaga agatcctttg atcttttcta   2599
cggggtctga cgctcagtgg aacgaaaact cacgttaagg gattttggtc atgagattat   2659
caaaaaggat cttcacctag atcctttta attaaaaatg aagttttaaa tcaatctaaa   2719
gtatatatga gtaaacttgg tctgacagtt accaatgctt aatcagtgag gcacctatct   2779
cagcgatctg tctatttcgt tcatccatag ttgcctgact ccccgtcgtg tagataacta   2839
cgatacggga gggcttacca tctggccccca gtgctgcaat gataccgcga gacccacgct   2899
caccggctcc agatttatca gcaataaacc agccagccgg aagggccgag cgcagaagtg   2959
```

| | |
|---|---|
| gtcctgcaac tttatccgcc tccatccagt ctattaattg ttgccgggaa gctagagtaa | 3019 |
| gtagttcgcc agttaatagt ttgcgcaacg ttgttgccat tgctacaggc atcgtggtgt | 3079 |
| cacgctcgtc gtttggtatg gcttcattca gctccggttc ccaacgatca aggcgagtta | 3139 |
| catgatcccc catgttgtgc aaaaaagcgg ttagctcctt cggtcctccg atcgttgtca | 3199 |
| gaagtaagtt ggccgcagtg ttatcactca tggttatggc agcactgcat aattctctta | 3259 |
| ctgtcatgcc atccgtaaga tgcttttctg tgactggtga gtactcaacc aagtcattct | 3319 |
| gagaatagtg tatgcggcga ccgagttgct cttgcccggc gtcaatacgg gataataccg | 3379 |
| cgccacatag cagaacttta aaagtgctca tcattggaaa acgttcttcg gggcgaaaac | 3439 |
| tctcaaggat cttaccgctg ttgagatcca gttcgatgta acccactcgt gcacccaact | 3499 |
| gatcttcagc atcttttact ttcaccagcg tttctgggtg agcaaaaaca ggaaggcaaa | 3559 |
| atgccgcaaa aaagggaata agggcgacac ggaaatgttg aatactcata ctcttccttt | 3619 |
| ttcaatatta ttgaagcatt tatcagggtt attgtctcat gagcggatac atatttgaat | 3679 |
| gtatttagaa aaataaacaa ataggggttc cgcgcacatt tccccgaaaa gtgccacctg | 3739 |
| acgtctaaga aaccattatt atcatgacat taacctataa aaataggcgt atcacgaggc | 3799 |
| cctttcgtc | 3808 |

<210> SEQ ID NO 10
<211> LENGTH: 124
<212> TYPE: PRT
<213> ORGANISM: Artificial Sequence
<220> FEATURE:
<223> OTHER INFORMATION: Schizochytrium sp. and Streptoalloteichus
      hindustanus

<400> SEQUENCE: 10

Met Ala Lys Leu Thr Ser Ala Val Pro Val Leu Thr Ala Arg Asp Val
1               5                   10                  15

Ala Gly Ala Val Glu Phe Trp Thr Asp Arg Leu Gly Phe Ser Arg Asp
            20                  25                  30

Phe Val Glu Asp Asp Phe Ala Gly Val Val Arg Asp Asp Val Thr Leu
        35                  40                  45

Phe Ile Ser Ala Val Gln Asp Gln Val Val Pro Asp Asn Thr Leu Ala
    50                  55                  60

Trp Val Trp Val Arg Gly Leu Asp Glu Leu Tyr Ala Glu Trp Ser Glu
65                  70                  75                  80

Val Val Ser Thr Asn Phe Arg Asp Ala Ser Gly Pro Ala Met Thr Glu
                85                  90                  95

Ile Gly Glu Gln Pro Trp Gly Arg Glu Phe Ala Leu Arg Asp Pro Ala
            100                 105                 110

Gly Asn Cys Val His Phe Val Ala Glu Glu Gln Asp
        115                 120

<210> SEQ ID NO 11
<211> LENGTH: 1416
<212> TYPE: DNA
<213> ORGANISM: Schizochytrium sp.

<400> SEQUENCE: 11

| | |
|---|---|
| gcaaaaggtc gagcttttcc acaaggagcg cattggcgct cctggcacgg ccgacttcaa | 60 |
| gctcattgcc gagatgatca accgtgcgga gcgacccgtc atctatgctg gcagggtgt | 120 |
| catgcagagc ccgttgaatg gcccggctgt gctcaaggag ttcgcggaga aggccaacat | 180 |

```
tcccgtgacc accaccatgc agggtctcgg cggctttgac gagcgtagtc ccctctccct      240
caagatgctc ggcatgcacg gctctgccta cgccaactac tcgatgcaga acgccgatct      300
tatcctggcg ctcggtgccc gctttgatga tcgtgtgacg ggccgcgttg acgcctttgc      360
tccggaggct cgccgtgccg agcgcgaggg ccgcggtggc atcgttcact ttgagatttc      420
ccccaagaac ctccacaagg tcgtccagcc caccgtcgcg gtcctcggcg acgtggtcga      480
gaacctcgcc aacgtcacgc cccacgtgca gcgccaggag cgcgagccgt ggtttgcgca      540
gatcgccgat tggaaggaga agcacccttt tctgctcgag tctgttgatt cggacgacaa      600
ggttctcaag ccgcagcagg tcctcacgga gcttaacaag cagattctcg agattcagga      660
gaaggacgcc gaccaggagg tctacatcac cacgggcgtc ggaagccacc agatgcaggc      720
agcgcagttc cttacctgga ccaagccgcg ccagtggatc tcctcgggtg gcgccggcac      780
tatgggctac ggccttccct cggccattgg cgccaagatt gccaagcccg atgctattgt      840
tattgacatc gatggtgatg cttcttattc gatgaccggt atggaattga tcacagcagc      900
cgaattcaag gttggcgtga agattcttct tttgcagaac aactttcagg gcatggtcaa      960
gaactggcag gatctctttt acgacaagcg ctactcgggc accgccatgt tcaacccgcg     1020
cttcgacaag gtcgccgatg cgatgcgtgc caagggtctc tactgcgcga aacagtcgga     1080
gctcaaggac aagatcaagg agtttctcga gtacgatgag ggtcccgtcc tcctcgaggt     1140
tttcgtggac aaggacacgc tcgtcttgcc catggtcccc gctggctttc cgctccacga     1200
gatggtcctc gagcctccta agcccaagga cgcctaagtt ctttttttcca tggcgggcga     1260 gcgagcgagc gcgcgagcgc gcaagtgcgc aagcgccttg ccttgctttg cttcgcttcg     1320
ctttgctttg cttcacacaa cctaagtatg aattcaagtt ttcttgcttg tcggcgaaaa     1380
aaaaaaaaaa aaaaaaaaaa aaaaaaaaaa aaaaaa                               1416

<210> SEQ ID NO 12
<211> LENGTH: 20
<212> TYPE: DNA
<213> ORGANISM: Schizochytrium sp.

<400> SEQUENCE: 12 ggatctctttt tacgacaagc                                                20

<210> SEQ ID NO 13
<211> LENGTH: 18
<212> TYPE: DNA
<213> ORGANISM: Schizochytrium sp.

<400> SEQUENCE: 13
ggttgtgtga agcaaagc                                                   18

<210> SEQ ID NO 14
<211> LENGTH: 7847
<212> TYPE: DNA
<213> ORGANISM: Schizochytrium sp.
<220> FEATURE:
<221> NAME/KEY: prim_transcript
<222> LOCATION: (1)..(1259)
<223> OTHER INFORMATION:
<220> FEATURE:
<221> NAME/KEY: CDS
<222> LOCATION: (1260)..(3314)
<223> OTHER INFORMATION:
<220> FEATURE:
<221> NAME/KEY: prim_transcript
<222> LOCATION: (3315)..(4887)
<223> OTHER INFORMATION:
```

<400> SEQUENCE: 14

```
ttgtcgacag caacttgcaa gttatacgcg accaccaggc aatctcagca cgcccagcga    60
gcacggagct tgcgaagagg gtttacaagt cgtcgttcat tcgctctcaa gctttgcctc   120
aacgcaacta ggcccaggcc tactttcact gtgtcttgtc ttgcctttca caccgaccga   180
gtgtgcacaa ccgtgttttg cacaaagcgc aagatgctca ctcgactgtg aagaaaggtt   240
gcgcgcaagc gactgcgact gcgaggatga ggatgactgg cagcctgttc aaaaactgaa   300
aatccgcgat gggtcagtgc cattcgcgca tgacgcctgc gagagacaag ttaactcgtg   360
tcactggcat gtcctagcat ctttacgcga gcaaaattca atcgctttat tttttcagtt   420
tcgtaacctt ctcgcaaccg cgaatcgccg tttcagcctg actaatctgc agctgcgtgg   480
cactgtcagt cagtcagtca gtcgtgcgcg ctgttccagc accgaggtcg cgcgtcgccg   540
cgcctggacc gctgctgcta ctgctagtgg cacggcaggt aggagcttgt tgccggaaca   600
ccagcagccg ccagtcgacg ccagccaggg gaaagtccgg cgtcgaaggg agaggaaggc   660
ggcgtgtgca aactaacgtt gaccactggc gcccgccgac acgagcagga agcaggcagc   720
tgcagagcgc agcgcgcaag tgcagaatgc gcgaaagatc cacttgcgcg cggcgggcgc   780
gcacttgcgg gcgcggcgcg aacagtgcgc gaaggagcg gtgcagacgg cgcgcagtga   840
cagtgggcgc aaagccgcgc agtaagcagc ggcggggaac ggtatacgca gtccgcgggg   900
ccgccgcaca cagaagtata cgcgggccga agtgggcgt cgcgcgcggg aagtgcggaa   960
tggcgggcaa ggaaaggagg agacggaaag agggcgggaa agagagagag agagagtgaa  1020
aaaagaaaga aagaaagaaa gaaagaaaga aagctcggag ccacgccgcg gggagagaga  1080
gaaatgaaag cacggcacgg caaagcaaag caaagcagac ccagccagac ccagccgagg  1140
gaggagcgcg cgcaggaccc gcgcggcgag cgagcgagca cggcgcgcga gcgagcgagc  1200
gagcgagcgc gcgagcgagc aaggcttgct gcgagcgatc gagcgagcga gcgggaaggc  1259
```

| | | | | | | | | | | | | | | | | |
|---|---|---|---|---|---|---|---|---|---|---|---|---|---|---|---|---|
| atg | agc | gcg | acc | cgc | gcg | gcg | acg | agg | aca | gcg | gcg | gcg | ctg | tcc | tcg | 1307 |
| Met | Ser | Ala | Thr | Arg | Ala | Ala | Thr | Arg | Thr | Ala | Ala | Ala | Leu | Ser | Ser | |
| 1 | | | | 5 | | | | | 10 | | | | | 15 | | |

| | | | | | | | | | | | | | | | |
|---|---|---|---|---|---|---|---|---|---|---|---|---|---|---|---|
| gcg ctg acg acg cct gta aag cag cag cag cag cag cag ctg cgc gta | | | | | | | | | | | | | | | 1355 |
| Ala Leu Thr Thr Pro Val Lys Gln Gln Gln Gln Gln Gln Leu Arg Val | | | | | | | | | | | | | | | |
| 20 25 30 | | | | | | | | | | | | | | | |

```
ggc gcg gcg tcg gca cgg ctg gcg gcc gcg gcg ttc tcg tcc ggc acg   1403
Gly Ala Ala Ser Ala Arg Leu Ala Ala Ala Ala Phe Ser Ser Gly Thr
             35                  40                  45 ggc gga gac gcg gcc aag aag gcg gcc gcg gcg agg gcg ttc tcc acg   1451
Gly Gly Asp Ala Ala Lys Lys Ala Ala Ala Ala Arg Ala Phe Ser Thr
 50                  55                  60 gga cgc ggc ccc aac gcg aca cgc gag aag agc tcg ctg gcc acg gtc   1499
Gly Arg Gly Pro Asn Ala Thr Arg Glu Lys Ser Ser Leu Ala Thr Val
 65                  70                  75                  80 cag gcg gcg acg gac gat gcg cgc ttc gtc ggc ctg acc ggc gcc caa   1547
Gln Ala Ala Thr Asp Asp Ala Arg Phe Val Gly Leu Thr Gly Ala Gln
                 85                  90                  95 atc ttt cat gag ctc atg cgc gag cac cag gtg gac acc atc ttt ggc   1595
Ile Phe His Glu Leu Met Arg Glu His Gln Val Asp Thr Ile Phe Gly
            100                 105                 110 tac cct ggc ggc gcc att ctg ccc gtt ttt gat gcc att ttt gag agt   1643
Tyr Pro Gly Gly Ala Ile Leu Pro Val Phe Asp Ala Ile Phe Glu Ser
        115                 120                 125 gac gcc ttc aag ttc att ctc gct cgc cac gag cag ggc gcc ggc cac   1691
Asp Ala Phe Lys Phe Ile Leu Ala Arg His Glu Gln Gly Ala Gly His
```

-continued

```
          130                 135                 140
atg gcc gag ggc tac gcg cgc gcc acg ggc aag ccc ggc gtt gtc ctc      1739
Met Ala Glu Gly Tyr Ala Arg Ala Thr Gly Lys Pro Gly Val Val Leu
145                 150                 155                 160 gtc acc tcg ggc cct gga gcc acc aac acc atc acc ccg atc atg gat      1787
Val Thr Ser Gly Pro Gly Ala Thr Asn Thr Ile Thr Pro Ile Met Asp
                165                 170                 175 gct tac atg gac ggt acg ccg ctg ctc gtg ttc acc ggc cag gtg ccc      1835
Ala Tyr Met Asp Gly Thr Pro Leu Leu Val Phe Thr Gly Gln Val Pro
            180                 185                 190 acc tct gct gtc ggc acg gac gct ttc cag gag tgt gac att gtt ggc      1883
Thr Ser Ala Val Gly Thr Asp Ala Phe Gln Glu Cys Asp Ile Val Gly
        195                 200                 205 atc agc cgc gcg tgc acc aag tgg aac gtc atg gtc aag gac gtg aag      1931
Ile Ser Arg Ala Cys Thr Lys Trp Asn Val Met Val Lys Asp Val Lys
    210                 215                 220 gag ctc ccg cgc cgc atc aat gag gcc ttt gag att gcc atg agc ggc      1979
Glu Leu Pro Arg Arg Ile Asn Glu Ala Phe Glu Ile Ala Met Ser Gly
225                 230                 235                 240 cgc ccg ggt ccc gtg ctc gtc gat ctt cct aag gat gtg acc gcc gtt      2027
Arg Pro Gly Pro Val Leu Val Asp Leu Pro Lys Asp Val Thr Ala Val
                245                 250                 255 gag ctc aag gaa atg ccc gac agc tcc ccc cag gtt gct gtg cgc cag      2075
Glu Leu Lys Glu Met Pro Asp Ser Ser Pro Gln Val Ala Val Arg Gln
            260                 265                 270 aag caa aag gtc gag ctt ttc cac aag gag cgc att ggc gct cct ggc      2123
Lys Gln Lys Val Glu Leu Phe His Lys Glu Arg Ile Gly Ala Pro Gly
        275                 280                 285 acg gcc gac ttc aag ctc att gcc gag atg atc aac cgt gcg gag cga      2171
Thr Ala Asp Phe Lys Leu Ile Ala Glu Met Ile Asn Arg Ala Glu Arg
    290                 295                 300 ccc gtc atc tat gct ggc cag ggt gtc atg cag agc ccg ttg aat ggc      2219
Pro Val Ile Tyr Ala Gly Gln Gly Val Met Gln Ser Pro Leu Asn Gly
305                 310                 315                 320 ccg gct gtg ctc aag gag ttc gcg gag aag gcc aac att ccc gtg acc      2267
Pro Ala Val Leu Lys Glu Phe Ala Glu Lys Ala Asn Ile Pro Val Thr
                325                 330                 335 acc acc atg cag ggt ctc ggc ggc ttt gac gag cgt agt ccc ctc tcc      2315
Thr Thr Met Gln Gly Leu Gly Gly Phe Asp Glu Arg Ser Pro Leu Ser
            340                 345                 350 ctc aag atg ctc ggc atg cac ggc tct gcc tac gcc aac tac tcg atg      2363
Leu Lys Met Leu Gly Met His Gly Ser Ala Tyr Ala Asn Tyr Ser Met
        355                 360                 365 cag aac gcc gat ctt atc ctg gcg ctc ggt gcc cgc ttt gat gat cgt      2411
Gln Asn Ala Asp Leu Ile Leu Ala Leu Gly Ala Arg Phe Asp Asp Arg
    370                 375                 380 gtg acg ggc cgc gtt gac gcc ttt gct ccg gag gct cgc cgt gcc gag      2459
Val Thr Gly Arg Val Asp Ala Phe Ala Pro Glu Ala Arg Arg Ala Glu
385                 390                 395                 400 cgc gag ggc cgc ggt ggc atc gtt cac ttt gag att tcc ccc aag aac      2507
Arg Glu Gly Arg Gly Gly Ile Val His Phe Glu Ile Ser Pro Lys Asn
                405                 410                 415 ctc cac aag gtc gtc cag ccc acc gtc gcg gtc ctc ggc gac gtg gtc      2555
Leu His Lys Val Val Gln Pro Thr Val Ala Val Leu Gly Asp Val Val
            420                 425                 430 gag aac ctc gcc aac gtc acg ccc cac gtg cag cgc cag gag cgc gag      2603
Glu Asn Leu Ala Asn Val Thr Pro His Val Gln Arg Gln Glu Arg Glu
        435                 440                 445 ccg tgg ttt gcg cag atc gcc gat tgg aag gag aag cac cct ttt ctg      2651
```

```
                               -continued

Pro Trp Phe Ala Gln Ile Ala Asp Trp Lys Glu Lys His Pro Phe Leu
    450                 455                 460 ctc gag tct gtt gat tcg gac gac aag gtt ctc aag ccg cag cag gtc    2699
Leu Glu Ser Val Asp Ser Asp Asp Lys Val Leu Lys Pro Gln Gln Val
465                 470                 475                 480 ctc acg gag ctt aac aag cag att ctc gag att cag gag aag gac gcc    2747
Leu Thr Glu Leu Asn Lys Gln Ile Leu Glu Ile Gln Glu Lys Asp Ala
                485                 490                 495 gac cag gag gtc tac atc acc acg ggc gtc gga agc cac cag atg cag    2795
Asp Gln Glu Val Tyr Ile Thr Thr Gly Val Gly Ser His Gln Met Gln
            500                 505                 510 gca gcg cag ttc ctt acc tgg acc aag ccg cgc cag tgg atc tcc tcg    2843
Ala Ala Gln Phe Leu Thr Trp Thr Lys Pro Arg Gln Trp Ile Ser Ser
        515                 520                 525 ggt ggc gcc ggc act atg ggc tac ggc ctt ccc tcg gcc att ggc gcc    2891
Gly Gly Ala Gly Thr Met Gly Tyr Gly Leu Pro Ser Ala Ile Gly Ala
    530                 535                 540 aag att gcc aag ccc gat gct att gtt att gac atc gat ggt gat gct    2939
Lys Ile Ala Lys Pro Asp Ala Ile Val Ile Asp Ile Asp Gly Asp Ala
545                 550                 555                 560 tct tat tcg atg acc ggt atg gaa ttg atc aca gca gcc gaa ttc aag    2987
Ser Tyr Ser Met Thr Gly Met Glu Leu Ile Thr Ala Ala Glu Phe Lys
                565                 570                 575 gtt ggc gtg aag att ctt ctt ttg cag aac aac ttt cag ggc atg gtc    3035
Val Gly Val Lys Ile Leu Leu Leu Gln Asn Asn Phe Gln Gly Met Val
            580                 585                 590 aag aac tgg cag gat ctc ttt tac gac aag cgc tac tcg ggc acc gcc    3083
Lys Asn Trp Gln Asp Leu Phe Tyr Asp Lys Arg Tyr Ser Gly Thr Ala
        595                 600                 605 atg ttc aac ccg cgc ttc gac aag gtc gcc gat gcg atg cgt gcc aag    3131
Met Phe Asn Pro Arg Phe Asp Lys Val Ala Asp Ala Met Arg Ala Lys
    610                 615                 620 ggt ctc tac tgc gcg aaa cag tcg gag ctc aag gac aag atc aag gag    3179
Gly Leu Tyr Cys Ala Lys Gln Ser Glu Leu Lys Asp Lys Ile Lys Glu
625                 630                 635                 640 ttt ctc gag tac gat gag ggt ccc gtc ctc ctc gag gtt ttc gtg gac    3227
Phe Leu Glu Tyr Asp Glu Gly Pro Val Leu Leu Glu Val Phe Val Asp
                645                 650                 655 aag gac acg ctc gtc ttg ccc atg gtc ccc gct ggc ttt ccg ctc cac    3275
Lys Asp Thr Leu Val Leu Pro Met Val Pro Ala Gly Phe Pro Leu His
            660                 665                 670 gag atg gtc ctc gag cct cct aag ccc aag gac gcc taa gttcttttt     3324
Glu Met Val Leu Glu Pro Pro Lys Pro Lys Asp Ala
        675                 680 ccatggcggg cgagcgagcg agcgcgcgag cgcgcaagtg cgcaagcgcc ttgccttgct  3384
ttgcttcgct tcgctttgct ttgcttcaca caacctaagt atgaattcaa gttttcttgc  3444
ttgtcggcga tgcctgcctg ccaaccagcc agccatccgg ccggccgtcc ttgacgcctt  3504
cgcttccggc gcggccatcg attcaattca cccatccgat acgttccgcc ccctcacgtc  3564
cgtctgcgca cgacccctgc acgaccacgc caaggccaac gcgccgctca gctcagcttg  3624
tcgacgagtc gcacgtcaca tatctcagat gcatttggac tgtgagtgtt attatgccac  3684
tagcacgcaa cgatcttcgg ggtcctcgct cattgcatcc gttcgggccc tgcaggcgtg  3744
gacgcgagtc gccgccgaga cgctgcagca ggccgctccg acgcgagggc tcgagctcgc  3804
cgcgcccgcg cgatgtctgc ctggcgccga ctgatctctg gagcgcaagg aagcacggc   3864 gacgcgagga ggaccgaaga gagacgctgg ggtatgcagg atataccogg ggcgggacat  3924
```

```
tcgttccgca tacactcccc cattcgagct tgctcgtcct tggcagagcc gagcgcgaac  3984
ggttccgaac gcggcaagga ttttggctct ggtgggtgga ctccgatcga ggcgcaggtt  4044
ctccgcaggt tctcgcaggc cggcagtggt cgttagaaat agggagtgcc ggagtcttga  4104
cgcgccttag ctcactctcc gcccacgcgc gcatcgccgc catgccgccg tcccgtctgt  4164
cgctgcgctg gccgcgaccg gctgcgccag agtacgacag tgggacagag ctcgaggcga  4224
cgcgaatcgc tcgggttgta agggtttcaa ggtcgggcg tcgtcgcgtg ccaaagtgaa  4284
aatagtaggg ggggggggg gtacccaccc cgggcaggtt ctcctcgcca gctaagtgc  4344
ctaagggagc gtagggttt cgttgaccag agaagcggag aacctgccgc ggcgcggaga  4404
acctatcggc ggagaacttg ccaggcgcga ggcagttctc caatttgcgg acagcggcgc  4464
gcccacgcga ggcggccgcg tggcgataca gcgaggcgac cgcgcgggc cgcgtggcga  4524
cacagctgcg cgcggagtcg gctgcgagaa ggcttctcgc tggcttggtt ggggtcgcgg  4584
gtggcagggg atggatgccc aggtacgtcg gcgtgcgcgc gcccagggag aaaaggacag  4644
acgcgcgggc ctgcgatgcg agcacgcgat gcgagcacgc gatgcgagca cgcgatgcga  4704
gcacgcgagc gagcgcccga gcaaatgcca cggaacacgc gttttttgtt tggtgatttc  4764
tatgtatgcg gggagacttc gatggccgaa aggggtgcaa ggccaaaaga tgctgacagc  4824
ttcgatcggt ctacgcgcg agcaggaaag ggagcaaggg gcggaattct tctgccttga  4884
cccgggggat ccactagttc tagagcggcc gccaccgcgg tggagctcca attcgcccta  4944
tagtgagtcg tattacgcgc gctcactggc cgtcgtttta caacgtcgtg actgggaaaa  5004
ccctggcgtt acccaactta atcgccttgc agcacatccc cctttcgcca gctggcgtaa  5064
tagcgaagag gcccgcaccg atcgcccttc ccaacagttg cgcagcctga atggcgaatg  5124
ggacgcgccc tgtagcggcg cattaagcgc ggcgggtgtg gtggttacgc gcagcgtgac  5184
cgctacactt gccagcgccc tagcgcccgc tcctttcgct ttcttccctt ctttctcgc  5244
cacgttcgcc ggctttcccc gtcaagctct aaatcggggg ctccctttag ggttccgatt  5304
tagtgcttta cggcacctcg accccaaaaa acttgattag ggtgatggtt cacgtagtgg  5364
gccatcgccc tgatagacgg ttttcgccc tttgacgttg gagtccacgt tctttaatag  5424
tggactcttg ttccaaactg gaacaacact caacccctatc tcggtctatt cttttgattt  5484
ataagggatt ttgccgattt cggcctattg gttaaaaaat gagctgattt aacaaaaatt  5544
taacgcgaat tttaacaaaa tattaacgct tacaatttag gtggcacttt tcggggaaat  5604
gtgcgcggaa cccctatttg tttatttttc taaatacatt caaatatgta tccgctcatg  5664
agacaataac cctgataaat gcttcaataa tattgaaaaa ggaagagtat gagtattcaa  5724
catttccgtg tcgcccttat cccttttttt gcggcatttt gccttcctgt ttttgctcac  5784
ccagaaacgc tggtgaaagt aaaagatgct gaagatcagt tgggtgcacg agtgggttac  5844
atcgaactgg atctcaacag cggtaagatc cttgagagtt ttcgccccga agaacgtttt  5904
ccaatgatga gcacttttaa agttctgcta tgtggcgcgg tattatcccg tattgacgcc  5964
gggcaagagc aactcggtcg ccgcatacac tattctcaga atgacttggt tgagtactca  6024
ccagtcacag aaaagcatct tacggatggc atgacagtaa gagaattatg cagtgctgcc  6084
ataaccatga gtgataacac tgcggccaac ttacttctga caacgatcgg aggaccgaag  6144
gagctaaccg cttttttgca acatggggg atcatgtaa ctcgccttga tcgttgggaa  6204
ccggagctga atgaagccat accaaacgac gagcgtgaca ccacgatgcc tgtagcaatg  6264
gcaacaacgt tgcgcaaact attaactggc gaactactta ctctagcttc ccggcaacaa  6324
```

-continued

```
ttaatagact ggatggaggc ggataaagtt gcaggaccac ttctgcgctc ggcccttccg    6384
gctggctggt ttattgctga taaatctgga gccggtgagc gtgggtctcg cggtatcatt    6444
gcagcactgg ggccagatgg taagccctcc cgtatcgtag ttatctacac gacggggagt    6504
caggcaacta tggatgaacg aaatagacag atcgctgaga taggtgcctc actgattaag    6564
cattggtaac tgtcagacca agtttactca tatatacttt agattgattt aaaacttcat    6624
ttttaattta aaaggatcta ggtgaagatc cttttgata atctcatgac caaaatccct    6684
taacgtgagt tttcgttcca ctgagcgtca gaccccgtag aaaagatcaa aggatcttct    6744
tgagatcctt tttttctgcg cgtaatctgc tgcttgcaaa caaaaaaacc accgctacca    6804
gcggtggttt gtttgccgga tcaagagcta ccaactcttt ttccgaaggt aactggcttc    6864
agcagagcgc agataccaaa tactgtcctt ctagtgtagc cgtagttagg ccaccacttc    6924
aagaactctg tagcaccgcc tacatacctc gctctgctaa tcctgttacc agtggctgct    6984
gccagtggcg ataagtcgtg tcttaccggg ttggactcaa gacgatagtt accggataag    7044
gcgcagcggt cgggctgaac ggggggttcg tgcacacagc ccagcttgga gcgaacgacc    7104
tacaccgaac tgagatacct acagcgtgag ctatgagaaa gcgccacgct tcccgaaggg    7164
agaaaggcgg acaggtatcc ggtaagcggc agggtcggaa caggagagcg cacgagggag    7224
cttccagggg gaaacgcctg gtatctttat agtcctgtcg ggtttcgcca cctctgactt    7284
gagcgtcgat ttttgtgatg ctcgtcaggg gggcggagcc tatggaaaaa cgccagcaac    7344
gcggcctttt tacggttcct ggccttttgc tggccttttg ctcacatgtt ctttcctgcg    7404 ttatccctg attctgtgga taaccgtatt accgcctttg agtgagctga taccgctcgc    7464
cgcagccgaa cgaccgagcg cagcgagtca gtgagcgagg aagcggaaga gcgcccaata    7524
cgcaaaccgc ctctccccgc gcgttggccg attcattaat gcagctggca cgacaggttt    7584
cccgactgga aagcgggcag tgagcgcaac gcaattaatg tgagttagct cactcattag    7644
gcaccccagg ctttacactt tatgcttccg gctcgtatgt tgtgtggaat tgtgagcgga    7704
taacaatttc acacaggaaa cagctatgac catgattacg ccaagcgcgc aattaaccct    7764
cactaaaggg aacaaaagct gggtaccggg ccccccctcg aggtcgacgg tatcgataag    7824
cttgatatcg aattcctgca gcc                                            7847
```

<210> SEQ ID NO 15
<211> LENGTH: 684
<212> TYPE: PRT
<213> ORGANISM: Schizochytrium sp.

<400> SEQUENCE: 15

```
Met Ser Ala Thr Arg Ala Ala Thr Arg Thr Ala Ala Ala Leu Ser Ser
1               5                   10                  15

Ala Leu Thr Thr Pro Val Lys Gln Gln Gln Gln Gln Gln Leu Arg Val
                20                  25                  30

Gly Ala Ala Ser Ala Arg Leu Ala Ala Ala Ala Phe Ser Ser Gly Thr
            35                  40                  45

Gly Gly Asp Ala Ala Lys Lys Ala Ala Ala Arg Ala Phe Ser Thr
        50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95
```

-continued

```
Ile Phe His Glu Leu Met Arg Glu His Gln Val Asp Thr Ile Phe Gly
                100                 105                 110
Tyr Pro Gly Ala Ile Leu Pro Val Phe Asp Ala Ile Phe Glu Ser
        115                 120                 125
Asp Ala Phe Lys Phe Ile Leu Ala Arg His Glu Gln Gly Ala Gly His
        130                 135                 140
Met Ala Glu Gly Tyr Ala Arg Ala Thr Gly Lys Pro Gly Val Val Leu
145                 150                 155                 160
Val Thr Ser Gly Pro Gly Ala Thr Asn Thr Ile Thr Pro Ile Met Asp
                165                 170                 175
Ala Tyr Met Asp Gly Thr Pro Leu Leu Val Phe Thr Gly Gln Val Pro
                180                 185                 190
Thr Ser Ala Val Gly Thr Asp Ala Phe Gln Glu Cys Asp Ile Val Gly
            195                 200                 205
Ile Ser Arg Ala Cys Thr Lys Trp Asn Val Met Val Lys Asp Val Lys
            210                 215                 220
Glu Leu Pro Arg Arg Ile Asn Glu Ala Phe Glu Ile Ala Met Ser Gly
225                 230                 235                 240
Arg Pro Gly Pro Val Leu Val Asp Leu Pro Lys Asp Val Thr Ala Val
                245                 250                 255
Glu Leu Lys Glu Met Pro Asp Ser Ser Pro Gln Val Ala Val Arg Gln
                260                 265                 270
Lys Gln Lys Val Glu Leu Phe His Lys Glu Arg Ile Gly Ala Pro Gly
            275                 280                 285
Thr Ala Asp Phe Lys Leu Ile Ala Glu Met Ile Asn Arg Ala Glu Arg
            290                 295                 300
Pro Val Ile Tyr Ala Gly Gln Gly Val Met Gln Ser Pro Leu Asn Gly
305                 310                 315                 320
Pro Ala Val Leu Lys Glu Phe Ala Glu Lys Ala Asn Ile Pro Val Thr
                325                 330                 335
Thr Thr Met Gln Gly Leu Gly Gly Phe Asp Glu Arg Ser Pro Leu Ser
                340                 345                 350
Leu Lys Met Leu Gly Met His Gly Ser Ala Tyr Ala Asn Tyr Ser Met
            355                 360                 365
Gln Asn Ala Asp Leu Ile Leu Ala Leu Gly Ala Arg Phe Asp Asp Arg
            370                 375                 380
Val Thr Gly Arg Val Asp Ala Phe Ala Pro Glu Ala Arg Arg Ala Glu
385                 390                 395                 400
Arg Glu Gly Arg Gly Gly Ile Val His Phe Glu Ile Ser Pro Lys Asn
                405                 410                 415
Leu His Lys Val Val Gln Pro Thr Val Ala Val Leu Gly Asp Val Val
            420                 425                 430
Glu Asn Leu Ala Asn Val Thr Pro His Val Gln Arg Gln Glu Arg Glu
            435                 440                 445
Pro Trp Phe Ala Gln Ile Ala Asp Trp Lys Glu Lys His Pro Phe Leu
        450                 455                 460
Leu Glu Ser Val Asp Ser Asp Lys Val Leu Lys Pro Gln Gln Val
465                 470                 475                 480
Leu Thr Glu Leu Asn Lys Gln Ile Leu Glu Ile Gln Glu Lys Asp Ala
                485                 490                 495
Asp Gln Glu Val Tyr Ile Thr Thr Gly Val Gly Ser His Gln Met Gln
                500                 505                 510
Ala Ala Gln Phe Leu Thr Trp Thr Lys Pro Arg Gln Trp Ile Ser Ser
```

-continued

```
                515                 520                 525
Gly Gly Ala Gly Thr Met Gly Tyr Gly Leu Pro Ser Ala Ile Gly Ala
        530                 535                 540
Lys Ile Ala Lys Pro Asp Ala Ile Val Ile Asp Ile Asp Gly Asp Ala
545                 550                 555                 560
Ser Tyr Ser Met Thr Gly Met Glu Leu Ile Thr Ala Ala Glu Phe Lys
                565                 570                 575
Val Gly Val Lys Ile Leu Leu Leu Gln Asn Asn Phe Gln Gly Met Val
            580                 585                 590
Lys Asn Trp Gln Asp Leu Phe Tyr Asp Lys Arg Tyr Ser Gly Thr Ala
                595                 600                 605
Met Phe Asn Pro Arg Phe Asp Lys Val Ala Asp Ala Met Arg Ala Lys
        610                 615                 620
Gly Leu Tyr Cys Ala Lys Gln Ser Glu Leu Lys Asp Lys Ile Lys Glu
625                 630                 635                 640
Phe Leu Glu Tyr Asp Glu Gly Pro Val Leu Glu Val Phe Val Asp
                645                 650                 655
Lys Asp Thr Leu Val Leu Pro Met Val Pro Ala Gly Phe Pro Leu His
            660                 665                 670
Glu Met Val Leu Glu Pro Pro Lys Pro Lys Asp Ala
        675                 680

<210> SEQ ID NO 16
<211> LENGTH: 30
<212> TYPE: DNA
<213> ORGANISM: Schizochytrium sp.

<400> SEQUENCE: 16
tatcgataag cttgacgtcg aattcctgca                                      30

<210> SEQ ID NO 17
<211> LENGTH: 32
<212> TYPE: DNA
<213> ORGANISM: Schizochytrium sp.

<400> SEQUENCE: 17
catggtcaag aacgttcagg atctctttta cg                                   32

<210> SEQ ID NO 18
<211> LENGTH: 7847
<212> TYPE: DNA
<213> ORGANISM: Schizochytrium sp.
<220> FEATURE:
<221> NAME/KEY: prim_transcript
<222> LOCATION: (1)..(1259)
<223> OTHER INFORMATION:
<220> FEATURE:
<221> NAME/KEY: CDS
<222> LOCATION: (1260)..(3314)
<223> OTHER INFORMATION:
<220> FEATURE:
<221> NAME/KEY: prim_transcript
<222> LOCATION: (3315)..(4887)
<223> OTHER INFORMATION:
<220> FEATURE:
<221> NAME/KEY: mutation
<222> LOCATION: (3042)..(3044)
<223> OTHER INFORMATION:

<400> SEQUENCE: 18
ttgtcgacag caacttgcaa gttatacgcg accaccaggc aatctcagca cgcccagcga    60
gcacggagct tgcgaagagg gtttacaagt cgtcgttcat tcgctctcaa gctttgcctc   120
```

-continued

```
aacgcaacta ggcccaggcc tactttcact gtgtcttgtc ttgcctttca caccgaccga    180
gtgtgcacaa ccgtgttttg cacaaagcgc aagatgctca ctcgactgtg aagaaaggtt    240
gcgcgcaagc gactgcgact gcgaggatga ggatgactgg cagcctgttc aaaaactgaa    300
aatccgcgat gggtcagtgc cattcgcgca tgacgcctgc gagagacaag ttaactcgtg    360
tcactggcat gtcctagcat ctttacgcga gcaaaattca atcgctttat tttttcagtt    420
tcgtaacctt ctcgcaaccg cgaatcgccg tttcagcctg actaatctgc agctgcgtgg    480
cactgtcagt cagtcagtca gtcgtgcgcg ctgttccagc accgaggtcg cgcgtcgccg    540
cgcctggacc gctgctgcta ctgctagtgg cacggcaggt aggagcttgt tgccggaaca    600
ccagcagccg ccagtcgacg ccagccaggg gaaagtccgg cgtcgaaggg agaggaaggc    660
ggcgtgtgca aactaacgtt gaccactggc gcccgccgac acgagcagga agcaggcagc    720
tgcagagcgc agcgcgcaag tgcagaatgc gcgaaagatc cacttgcgcg cggcgggcgc    780
gcacttgcgg gcgcggcgcg aacagtgcg gaaaggagcg gtgcagacgg cgcgcagtga    840
cagtgggcgc aaagccgcgc agtaagcagc ggcggggaac ggtatacgca gtgccgcggg    900
ccgccgcaca cagaagtata cgcgggccga agtggggcgt cgcgcgcggg aagtgcggaa    960
tggcgggcaa ggaaaggagg agacggaaag agggcgggaa agagagagag agagagtgaa   1020
aaaagaaaga aagaaagaaa gaaagaaaga aagctcggag ccacgccgcg gggagagaga   1080
gaaatgaaag cacggcacgg caaagcaaag caaagcagac ccagccagac ccagccgagg   1140
gaggagcgcg cgcaggaccc gcgcggcgag cgagcgagca cggcgcgcga gcgagcgagc   1200
gagcgagcgc gcgagcgagc aaggcttgct gcgagcgatc gagcgagcga gcgggaagg    1259
```

| | | | | | | | | | | | | | | | | |
|---|---|---|---|---|---|---|---|---|---|---|---|---|---|---|---|---|
| atg | agc | gcg | acc | cgc | gcg | gcg | acg | agg | aca | gcg | gcg | gcg | ctg | tcc | tcg | 1307 |
| Met | Ser | Ala | Thr | Arg | Ala | Ala | Thr | Arg | Thr | Ala | Ala | Ala | Leu | Ser | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcg | ctg | acg | acg | cct | gta | aag | cag | cag | cag | cag | cag | cag | ctg | cgc | gta | 1355 |
| Ala | Leu | Thr | Thr | Pro | Val | Lys | Gln | Gln | Gln | Gln | Gln | Gln | Leu | Arg | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ggc | gcg | gcg | tcg | gca | cgg | ctg | gcg | gcc | gcg | gcg | ttc | tcg | tcc | ggc | acg | 1403 |
| Gly | Ala | Ala | Ser | Ala | Arg | Leu | Ala | Ala | Ala | Ala | Phe | Ser | Ser | Gly | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| ggc | gga | gac | gcg | gcc | aag | aag | gcg | gcc | gcg | gcg | agg | gcg | ttc | tcc | acg | 1451 |
| Gly | Gly | Asp | Ala | Ala | Lys | Lys | Ala | Ala | Ala | Ala | Arg | Ala | Phe | Ser | Thr | |
| | 50 | | | | | 55 | | | | | 60 | | | | | |

| | | | | | | | | | | | | | | | | |
|---|---|---|---|---|---|---|---|---|---|---|---|---|---|---|---|---|
| gga | cgc | ggc | ccc | aac | gcg | aca | cgc | gag | aag | agc | tcg | ctg | gcc | acg | gtc | 1499 |
| Gly | Arg | Gly | Pro | Asn | Ala | Thr | Arg | Glu | Lys | Ser | Ser | Leu | Ala | Thr | Val | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| cag | gcg | gcg | acg | gac | gat | gcg | cgc | ttc | gtc | ggc | ctg | acc | ggc | gcc | caa | 1547 |
| Gln | Ala | Ala | Thr | Asp | Asp | Ala | Arg | Phe | Val | Gly | Leu | Thr | Gly | Ala | Gln | |
| | | | 85 | | | | | 90 | | | | | 95 | | | |

| | | | | | | | | | | | | | | | | |
|---|---|---|---|---|---|---|---|---|---|---|---|---|---|---|---|---|
| atc | ttt | cat | gag | ctc | atg | cgc | gag | cac | cag | gtg | gac | acc | atc | ttt | ggc | 1595 |
| Ile | Phe | His | Glu | Leu | Met | Arg | Glu | His | Gln | Val | Asp | Thr | Ile | Phe | Gly | |
| | | 100 | | | | | 105 | | | | | 110 | | | | |

| | | | | | | | | | | | | | | | | |
|---|---|---|---|---|---|---|---|---|---|---|---|---|---|---|---|---|
| tac | cct | ggc | ggc | gcc | att | ctg | ccc | gtt | ttt | gat | gcc | att | ttt | gag | agt | 1643 |
| Tyr | Pro | Gly | Gly | Ala | Ile | Leu | Pro | Val | Phe | Asp | Ala | Ile | Phe | Glu | Ser | |
| | 115 | | | | | 120 | | | | | 125 | | | | | |

| | | | | | | | | | | | | | | | | |
|---|---|---|---|---|---|---|---|---|---|---|---|---|---|---|---|---|
| gac | gcc | ttc | aag | ttc | att | ctc | gct | cgc | cac | gag | cag | ggc | gcc | ggc | cac | 1691 |
| Asp | Ala | Phe | Lys | Phe | Ile | Leu | Ala | Arg | His | Glu | Gln | Gly | Ala | Gly | His | |
| 130 | | | | | 135 | | | | | 140 | | | | | | |

| | | | | | | | | | | | | | | | | |
|---|---|---|---|---|---|---|---|---|---|---|---|---|---|---|---|---|
| atg | gcc | gag | ggc | tac | gcg | cgc | gcc | acg | ggc | aag | ccc | ggc | gtt | gtc | ctc | 1739 |
| Met | Ala | Glu | Gly | Tyr | Ala | Arg | Ala | Thr | Gly | Lys | Pro | Gly | Val | Val | Leu | |
| 145 | | | | 150 | | | | | 155 | | | | | 160 | | |

-continued

| | | |
|---|---|---|
| gtc acc tcg ggc cct gga gcc acc aac acc atc acc ccg atc atg gat<br>Val Thr Ser Gly Pro Gly Ala Thr Asn Thr Ile Thr Pro Ile Met Asp<br>                165                        170                    175 | 1787 |
| gct tac atg gac ggt acg ccg ctg ctc gtg ttc acc ggc cag gtg ccc<br>Ala Tyr Met Asp Gly Thr Pro Leu Leu Val Phe Thr Gly Gln Val Pro<br>          180                        185                      190 | 1835 |
| acc tct gct gtc ggc acg gac gct ttc cag gag tgt gac att gtt ggc<br>Thr Ser Ala Val Gly Thr Asp Ala Phe Gln Glu Cys Asp Ile Val Gly<br>                195                        200                    205 | 1883 |
| atc agc cgc gcg tgc acc aag tgg aac gtc atg gtc aag gac gtg aag<br>Ile Ser Arg Ala Cys Thr Lys Trp Asn Val Met Val Lys Asp Val Lys<br>210                        215                        220 | 1931 |
| gag ctc ccg cgc cgc atc aat gag gcc ttt gag att gcc atg agc ggc<br>Glu Leu Pro Arg Arg Ile Asn Glu Ala Phe Glu Ile Ala Met Ser Gly<br>225                        230                        235                    240 | 1979 |
| cgc ccg ggt ccc gtg ctc gtc gat ctt cct aag gat gtg acc gcc gtt<br>Arg Pro Gly Pro Val Leu Val Asp Leu Pro Lys Asp Val Thr Ala Val<br>                        245                        250                    255 | 2027 |
| gag ctc aag gaa atg ccc gac agc tcc ccc cag gtt gct gtg cgc cag<br>Glu Leu Lys Glu Met Pro Asp Ser Ser Pro Gln Val Ala Val Arg Gln<br>          260                        265                      270 | 2075 |
| aag caa aag gtc gag ctt ttc cac aag gag cgc att ggc gct cct ggc<br>Lys Gln Lys Val Glu Leu Phe His Lys Glu Arg Ile Gly Ala Pro Gly<br>                275                        280                    285 | 2123 |
| acg gcc gac ttc aag ctc att gcc gag atg atc aac cgt gcg gag cga<br>Thr Ala Asp Phe Lys Leu Ile Ala Glu Met Ile Asn Arg Ala Glu Arg<br>          290                        295                    300 | 2171 |
| ccc gtc atc tat gct ggc cag ggt gtc atg cag agc ccg ttg aat ggc<br>Pro Val Ile Tyr Ala Gly Gln Gly Val Met Gln Ser Pro Leu Asn Gly<br>305                        310                        315                    320 | 2219 |
| ccg gct gtg ctc aag gag ttc gcg gag aag gcc aac att ccc gtg acc<br>Pro Ala Val Leu Lys Glu Phe Ala Glu Lys Ala Asn Ile Pro Val Thr<br>                        325                        330                    335 | 2267 |
| acc acc atg cag ggt ctc ggc ggc ttt gac gag cgt agt ccc ctc tcc<br>Thr Thr Met Gln Gly Leu Gly Gly Phe Asp Glu Arg Ser Pro Leu Ser<br>                340                        345                    350 | 2315 |
| ctc aag atg ctc ggc atg cac ggc tct gcc tac gcc aac tac tcg atg<br>Leu Lys Met Leu Gly Met His Gly Ser Ala Tyr Ala Asn Tyr Ser Met<br>                355                        360                    365 | 2363 |
| cag aac gcc gat ctt atc ctg gcg ctc ggt gcc cgc ttt gat gat cgt<br>Gln Asn Ala Asp Leu Ile Leu Ala Leu Gly Ala Arg Phe Asp Asp Arg<br>          370                        375                    380 | 2411 |
| gtg acg ggc cgc gtt gac gcc ttt gct ccg gag gct cgc cgt gcc gag<br>Val Thr Gly Arg Val Asp Ala Phe Ala Pro Glu Ala Arg Arg Ala Glu<br>385                        390                        395                    400 | 2459 |
| cgc gag ggc cgc ggt ggc atc gtt cac ttt gag att tcc ccc aag aac<br>Arg Glu Gly Arg Gly Gly Ile Val His Phe Glu Ile Ser Pro Lys Asn<br>                        405                        410                    415 | 2507 |
| ctc cac aag gtc gtc cag ccc acc gtc gcg gtc ctc ggc gac gtg gtc<br>Leu His Lys Val Val Gln Pro Thr Val Ala Val Leu Gly Asp Val Val<br>                420                        425                    430 | 2555 |
| gag aac ctc gcc aac gtc acg ccc cac gtg cag cgc cag gag cgc gag<br>Glu Asn Leu Ala Asn Val Thr Pro His Val Gln Arg Gln Glu Arg Glu<br>          435                        440                    445 | 2603 |
| ccg tgg ttt gcg cag atc gcc gat tgg aag gag aag cac cct ttt ctg<br>Pro Trp Phe Ala Gln Ile Ala Asp Trp Lys Glu Lys His Pro Phe Leu<br>          450                        455                    460 | 2651 |
| ctc gag tct gtt gat tcg gac gac aag gtt ctc aag ccg cag cag gtc<br>Leu Glu Ser Val Asp Ser Asp Asp Lys Val Leu Lys Pro Gln Gln Val<br>465                        470                        475                    480 | 2699 |

| | |
|---|---|
| ctc acg gag ctt aac aag cag att ctc gag att cag gag aag gac gcc<br>Leu Thr Glu Leu Asn Lys Gln Ile Leu Glu Ile Gln Glu Lys Asp Ala<br>                485                  490                495 | 2747 |
| gac cag gag gtc tac atc acc acg ggc gtc gga agc cac cag atg cag<br>Asp Gln Glu Val Tyr Ile Thr Thr Gly Val Gly Ser His Gln Met Gln<br>        500                  505                  510 | 2795 |
| gca gcg cag ttc ctt acc tgg acc aag ccg cgc cag tgg atc tcc tcg<br>Ala Ala Gln Phe Leu Thr Trp Thr Lys Pro Arg Gln Trp Ile Ser Ser<br>                515                  520                525 | 2843 |
| ggt ggc gcc ggc act atg ggc tac ggc ctt ccc tcg gcc att ggc gcc<br>Gly Gly Ala Gly Thr Met Gly Tyr Gly Leu Pro Ser Ala Ile Gly Ala<br>530                  535                  540 | 2891 |
| aag att gcc aag ccc gat gct att gtt att gac atc gat ggt gat gct<br>Lys Ile Ala Lys Pro Asp Ala Ile Val Ile Asp Ile Asp Gly Asp Ala<br>545                  550                555              560 | 2939 |
| tct tat tcg atg acc ggt atg gaa ttg atc aca gca gcc gaa ttc aag<br>Ser Tyr Ser Met Thr Gly Met Glu Leu Ile Thr Ala Ala Glu Phe Lys<br>                  565                570              575 | 2987 |
| gtt ggc gtg aag att ctt ctt ttg cag aac aac ttt cag ggc atg gtc<br>Val Gly Val Lys Ile Leu Leu Leu Gln Asn Asn Phe Gln Gly Met Val<br>                580                  585                590 | 3035 |
| aag aac gtt cag gat ctc ttt tac gac aag cgc tac tcg ggc acc gcc<br>Lys Asn Val Gln Asp Leu Phe Tyr Asp Lys Arg Tyr Ser Gly Thr Ala<br>        595                  600                  605 | 3083 |
| atg ttc aac ccg cgc ttc gac aag gtc gcc gat gcg atg cgt gcc aag<br>Met Phe Asn Pro Arg Phe Asp Lys Val Ala Asp Ala Met Arg Ala Lys<br>610                  615                  620 | 3131 |
| ggt ctc tac tgc gcg aaa cag tcg gag ctc aag gac aag atc aag gag<br>Gly Leu Tyr Cys Ala Lys Gln Ser Glu Leu Lys Asp Lys Ile Lys Glu<br>625                  630                635              640 | 3179 |
| ttt ctc gag tac gat gag ggt ccc gtc ctc ctc gag gtt ttc gtg gac<br>Phe Leu Glu Tyr Asp Glu Gly Pro Val Leu Leu Glu Val Phe Val Asp<br>                  645                650              655 | 3227 |
| aag gac acg ctc gtc ttg ccc atg gtc ccc gct ggc ttt ccg ctc cac<br>Lys Asp Thr Leu Val Leu Pro Met Val Pro Ala Gly Phe Pro Leu His<br>        660                  665                  670 | 3275 |
| gag atg gtc ctc gag cct cct aag ccc aag gac gcc taa gttctttttt<br>Glu Met Val Leu Glu Pro Pro Lys Pro Lys Asp Ala<br>                675                  680 | 3324 |
| ccatggcggg cgagcgagcg agcgcgcgag cgcgcaagtg cgcaagcgcc ttgccttgct | 3384 |
| ttgcttcgct tcgctttgct ttgcttcaca caacctaagt atgaattcaa gttttcttgc | 3444 |
| ttgtcggcga tgcctgcctg ccaaccagcc agccatccgg ccggccgtcc ttgacgcctt | 3504 |
| cgcttccggc gcggccatcg attcaattca cccatccgat acgttccgcc ccctcacgtc | 3564 |
| cgtctgcgca cgacccctgc acgaccacgc caaggccaac gcgccgctca gctcagcttg | 3624 |
| tcgacgagtc gcacgtcaca tatctcagat gcatttggac tgtgagtgtt attatgccac | 3684 |
| tagcacgcaa cgatcttcgg ggtcctcgct cattgcatcc gttcgggccc tgcaggcgtg | 3744 |
| gacgcgagtc gccgccgaga cgctgcagca ggccgctccg acgcgagggc tcgagctcgc | 3804 |
| cgcgccgcg cgatgtctgc ctggcgccga ctgatctctg gagcgcaagg aagacacggc | 3864 |
| gacgcgagga ggaccgaaga gagacgctgg ggtatgcagg atataccggg gcgggacat | 3924 |
| tcgttccgca tacactcccc cattcgagct tgctcgtcct tggcagagcc gagcgcgaac | 3984 |
| ggttccgaac gcggcaagga ttttggctct ggtgggtgga ctccgatcga ggcgcaggtt | 4044 |
| ctccgcaggt tctcgcaggc cggcagtggt cgttagaaat agggagtgcc ggagtcttga | 4104 |

```
cgcgccttag ctcactctcc gcccacgcgc gcatcgccgc catgccgccg tcccgtctgt   4164
cgctgcgctg gccgcgaccg gctgcgccag agtacgacag tgggacagag ctcgaggcga   4224
cgcgaatcgc tcgggttgta agggtttcaa gggtcgggcg tcgtcgcgtg ccaaagtgaa   4284
aatagtaggg gggggggggg gtacccaccc cgggcaggtt ctcctcgcca gcctaagtgc   4344
ctaagggagc gtaggggttt cgttgaccag agaagcggag aacctgccgc ggcgcggaga   4404
acctatcggc ggagaacttg ccaggcgcga ggcagttctc caatttgcgg acagcggcgc   4464
gcccacgcga ggcggccgcg tggcgataca gcgaggcgac cgcgcgggc cgcgtggcga    4524
cacagctgcg cgcggagtcg gctgcgagaa ggcttctcgc tggcttggtt ggggtcgcgg   4584
gtggcagggg atggatgccc aggtacgtcg gcgtgcgcgc gcccagggag aaaaggacag   4644
acgcgcgggc ctgcgatgcg agcacgcgat gcgagcacgc gatgcgagca cgcgatgcga   4704
gcacgcgagc gagcgcccga gcaaatgcca cggaacacgc gttttttgtt tggtgatttc   4764
tatgtatgcg gggagacttc gatggccgaa agggtgcaa ggccaaaaga tgctgacagc     4824
ttcgatcggt ctacggcgcg agcaggaaag ggagcaaggg gcggaattct tctgccttga   4884
cccgggggat ccactagttc tagagcggcc gccaccgcgg tggagctcca attcgcccta   4944
tagtgagtcg tattacgcgc gctcactggc cgtcgtttta caacgtcgtg actgggaaaa   5004
ccctggcgtt acccaactta atcgccttgc agcacatccc cctttcgcca gctggcgtaa   5064
tagcgaagag gcccgcaccg atcgcccttc ccaacagttg cgcagcctga atggcgaatg   5124
ggacgcgccc tgtagcggcg cattaagcgc ggcgggtgtg gtggttacgc gcagcgtgac   5184
cgctacactt gccagcgccc tagcgcccgc tcctttcgct ttcttccctt cctttctcgc   5244
cacgttcgcc ggctttcccc gtcaagctct aaatcggggg ctcccttag ggttccgatt     5304
tagtgcttta cggcacctcg accccaaaaa acttgattag ggtgatggtt cacgtagtgg   5364
gccatcgccc tgatagacgg ttttcgccc tttgacgttg gagtccacgt tctttaatag     5424
tggactcttg ttccaaactg gaacaacact caaccctatc tcggtctatt cttttgattt   5484
ataagggatt ttgccgattt cggcctattg gttaaaaaat gagctgattt aacaaaaatt   5544
taacgcgaat tttaacaaaa tattaacgct tacaatttag gtggcacttt tcggggaaat   5604
gtgcgcggaa cccctatttg tttatttttc taaatacatt caaatatgta tccgctcatg   5664
agacaataac cctgataaat gcttcaataa tattgaaaaa ggaagagtat gagtattcaa   5724
catttccgtg tcgcccttat tcctttttt gcggcatttt gccttcctgt ttttgctcac     5784
ccagaaacgc tggtgaaagt aaaagatgct gaagatcagt tgggtgcacg agtgggttac   5844
atcgaactgg atctcaacag cggtaagatc cttgagagtt ttcgccccga agaacgtttt   5904
ccaatgatga gcacttttaa agttctgcta tgtggcgcgg tattatcccg tattgacgcc   5964
gggcaagagc aactcggtcg ccgcatacac tattctcaga atgacttggt tgagtactca   6024
ccagtcacag aaaagcatct tacgatggc atgcagtaa gagaattatg cagtgctgcc      6084
ataaccatga gtgataacac tgcggccaac ttacttctga caacgatcgg aggaccgaag   6144
gagctaaccg ctttttttgca caacatgggg gatcatgtaa ctcgccttga tcgttgggaa   6204
ccggagctga atgaagccat accaaacgac gagcgtgaca ccacgatgcc tgtagcaatg   6264
gcaacaacgt tgcgcaaact attaactggc gaactactta ctctagcttc ccggcaacaa   6324
ttaatagact ggatggaggc ggataaagtt gcaggaccac ttctgcgctc ggcccttccg   6384
gctggctggt ttattgctga taaatctgga gccggtgagc gtgggtctcg cggtatcatt   6444
gcagcactgg ggccagatgg taagccctcc cgtatcgtag ttatctacac gacggggagt   6504
```

```
caggcaacta tggatgaacg aaatagacag atcgctgaga taggtgcctc actgattaag    6564
cattggtaac tgtcagacca agtttactca tatatacttt agattgattt aaaacttcat    6624
ttttaattta aaaggatcta ggtgaagatc cttttttgata atctcatgac caaaatccct    6684
taacgtgagt tttcgttcca ctgagcgtca gaccccgtag aaaagatcaa aggatcttct    6744
tgagatcctt tttttctgcg cgtaatctgc tgcttgcaaa caaaaaaacc accgctacca    6804
gcggtggttt gtttgccgga tcaagagcta ccaactcttt ttccgaaggt aactggcttc    6864
agcagagcgc agataccaaa tactgtcctt ctagtgtagc cgtagttagg ccaccacttc    6924
aagaactctg tagcaccgcc tacatacctc gctctgctaa tcctgttacc agtggctgct    6984
gccagtggcg ataagtcgtg tcttaccggg ttggactcaa gacgatagtt accggataag    7044
gcgcagcggt cgggctgaac ggggggttcg tgcacacagc ccagcttgga gcgaacgacc    7104
tacaccgaac tgagatacct acagcgtgag ctatgagaaa gcgccacgct tcccgaaggg    7164
agaaaggcgg acaggtatcc ggtaagcggc agggtcggaa caggagagcg cacgagggag    7224
cttccagggg gaaacgcctg gtatctttat agtcctgtcg ggtttcgcca cctctgactt    7284
gagcgtcgat ttttgtgatg ctcgtcaggg gggcggagcc tatggaaaaa cgccagcaac    7344
gcggcctttt tacggttcct ggccttttgc tggccttttg ctcacatgtt ctttcctgcg    7404
ttatcccctg attctgtgga taaccgtatt accgcctttg agtgagctga taccgctcgc    7464
cgcagccgaa cgaccgagcg cagcgagtca gtgagcgagg aagcggaaga gcgcccaata    7524
cgcaaaccgc ctctccccgc gcgttggccg attcattaat gcagctggca cgacaggttt    7584
cccgactgga aagcgggcag tgagcgcaac gcaattaatg tgagttagct cactcattag    7644
gcaccccagg ctttacactt tatgcttccg gctcgtatgt tgtgtggaat tgtgagcgga    7704
taacaatttc acacaggaaa cagctatgac catgattacg ccaagcgcgc aattaaccct    7764
cactaaaggg aacaaaagct gggtaccggg ccccccctcg aggtcgacgg tatcgataag    7824
cttgacgtcg aattcctgca gcc                                            7847
```

<210> SEQ ID NO 19
<211> LENGTH: 684
<212> TYPE: PRT
<213> ORGANISM: Schizochytrium sp.

<400> SEQUENCE: 19

```
Met Ser Ala Thr Arg Ala Ala Thr Arg Thr Ala Ala Ala Leu Ser Ser
1               5                   10                  15

Ala Leu Thr Thr Pro Val Lys Gln Gln Gln Gln Gln Leu Arg Val
            20                  25                  30

Gly Ala Ala Ser Ala Arg Leu Ala Ala Ala Ala Phe Ser Ser Gly Thr
        35                  40                  45

Gly Gly Asp Ala Ala Lys Lys Ala Ala Ala Arg Ala Phe Ser Thr
    50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
            100                 105                 110

Tyr Pro Gly Gly Ala Ile Leu Pro Val Phe Asp Ala Ile Phe Glu Ser
        115                 120                 125
```

```
Asp Ala Phe Lys Phe Ile Leu Ala Arg His Glu Gln Gly Ala Gly His
        130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Pro
            180                 185                 190

Thr Ser Ala Val Gly Thr Asp Ala Phe Gln Glu Cys Asp Ile Val Gly
        195                 200                 205

Ile Ser Arg Ala Cys Thr Lys Trp Asn Val Met Val Lys Asp Val Lys
    210                 215                 220

Glu Leu Pro Arg Arg Ile Asn Glu Ala Phe Glu Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
        275                 280                 285

Thr Ala Asp Phe Lys Leu Ile Ala Glu Met Ile Asn Arg Ala Glu Arg
    290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335

Thr Thr Met Gln Gly Leu Gly Gly Phe Asp Glu Arg Ser Pro Leu Ser
            340                 345                 350

Leu Lys Met Leu Gly Met His Gly Ser Ala Tyr Ala Asn Tyr Ser Met
        355                 360                 365

Gln Asn Ala Asp Leu Ile Leu Ala Leu Gly Ala Arg Phe Asp Asp Arg
    370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
            420                 425                 430

Glu Asn Leu Ala Asn Val Thr Pro His Val Gln Arg Gln Glu Arg Glu
        435                 440                 445

Pro Trp Phe Ala Gln Ile Ala Asp Trp Lys Glu Lys His Pro Phe Leu
    450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
            485                 490                 495

Asp Gln Glu Val Tyr Ile Thr Thr Gly Val Gly Ser His Gln Met Gln
        500                 505                 510

Ala Ala Gln Phe Leu Thr Trp Thr Lys Pro Arg Gln Trp Ile Ser Ser
    515                 520                 525

Gly Gly Ala Gly Thr Met Gly Tyr Gly Leu Pro Ser Ala Ile Gly Ala
530                 535                 540

Lys Ile Ala Lys Pro Asp Ala Ile Val Ile Asp Ile Asp Gly Asp Ala
```

```
545                 550                 555                 560
Ser Tyr Ser Met Thr Gly Met Glu Leu Ile Thr Ala Ala Glu Phe Lys
                565                 570                 575
Val Gly Val Lys Ile Leu Leu Leu Gln Asn Asn Phe Gln Gly Met Val
                580                 585                 590
Lys Asn Val Gln Asp Leu Phe Tyr Asp Lys Arg Tyr Ser Gly Thr Ala
                595                 600                 605
Met Phe Asn Pro Arg Phe Asp Lys Val Ala Asp Ala Met Arg Ala Lys
                610                 615                 620
Gly Leu Tyr Cys Ala Lys Gln Ser Glu Leu Lys Asp Lys Ile Lys Glu
625                 630                 635                 640
Phe Leu Glu Tyr Asp Glu Gly Pro Val Leu Leu Glu Val Phe Val Asp
                645                 650                 655
Lys Asp Thr Leu Val Leu Pro Met Val Pro Ala Gly Phe Pro Leu His
                660                 665                 670
Glu Met Val Leu Glu Pro Pro Lys Pro Lys Asp Ala
                675                 680
```

```
<210> SEQ ID NO 20
<211> LENGTH: 26
<212> TYPE: DNA
<213> ORGANISM: Schizochytrium sp.

<400> SEQUENCE: 20
ccggccaggt gcagacctct gctgtc                                         26

<210> SEQ ID NO 21
<211> LENGTH: 7847
<212> TYPE: DNA
<213> ORGANISM: Schizochytrium sp.
<220> FEATURE:
<221> NAME/KEY: prim_transcript
<222> LOCATION: (1)..(1259)
<223> OTHER INFORMATION:
<220> FEATURE:
<221> NAME/KEY: mutation
<222> LOCATION: (1834)..(1835)
<223> OTHER INFORMATION:
<220> FEATURE:
<221> NAME/KEY: CDS
<222> LOCATION: (1260)..(3314)
<223> OTHER INFORMATION:
<220> FEATURE:
<221> NAME/KEY: prim_transcript
<222> LOCATION: (3315)..(4887)
<223> OTHER INFORMATION:

<400> SEQUENCE: 21
ttgtcgacag caacttgcaa gttatacgcg accaccaggc aatctcagca cgcccagcga      60
gcacggagct tgcgaagagg gtttacaagt cgtcgttcat tcgctctcaa gctttgcctc     120
aacgcaacta ggcccaggcc tactttcact gtgtcttgtc ttgcctttca caccgaccga     180
gtgtgcacaa ccgtgttttg cacaaagcgc aagatgctca ctcgactgtg aagaaaggtt     240
gcgcgcaagc gactgcgact gcgaggatga ggatgactgg cagcctgttc aaaaactgaa     300
aatccgcgat gggtcagtgc cattcgcgca tgacgcctgc gagagacaag ttaactcgtg     360
tcactggcat gtcctagcat ctttacgcga gcaaaattca atcgctttat tttttcagtt     420
tcgtaacctt ctcgcaaccg cgaatcgccg tttcagcctg actaatctgc agctgcgtgg     480
cactgtcagt cagtcagtca gtcgtgcgcg ctgttccagc accgaggtcg cgcgtcgccg     540
cgcctggacc gctgctgcta ctgctagtgg cacggcaggt aggagcttgt tgccggaaca     600
```

-continued

```
ccagcagccg ccagtcgacg ccagccaggg gaaagtccgg cgtcgaaggg agaggaaggc      660
ggcgtgtgca aactaacgtt gaccactggc gcccgccgac acgagcagga agcaggcagc      720
tgcagagcgc agcgcgcaag tgcagaatgc gcgaaagatc cacttgcgcg cggcgggcgc      780
gcacttgcgg gcgcggcgcg aacagtgcg gaaaggagcg gtgcagacgg cgcgcagtga       840
cagtgggcgc aaagccgcgc agtaagcagc ggcggggaac ggtatacgca gtgccgcggg      900
ccgccgcaca cagaagtata cgcgggccga agtgggcgt cgcgcgcggg aagtgcggaa       960
tggcgggcaa ggaaaggagg agacggaaag agggcgggaa agagagagag agagagtgaa     1020
aaaagaaaga aagaaagaaa gaaagaaaga aagctcggag ccacgccgcg gggagagaga     1080
gaaatgaaag cacggcacgg caaagcaaag caaagcagac ccagccagac ccagccgagg     1140
gaggagcgcg cgcaggaccc gcgcggcgag cgagcgagca cggcgcgcga gcgagcgagc     1200
gagcgagcgc gcgagcgagc aaggcttgct gcgagcgatc gagcgagcga gcgggaagg     1259
atg agc gcg acc cgc gcg gcg acg agg aca gcg gcg gcg ctg tcc tcg       1307
Met Ser Ala Thr Arg Ala Ala Thr Arg Thr Ala Ala Ala Leu Ser Ser
1               5                  10                  15 gcg ctg acg acg cct gta aag cag cag cag cag cag cag ctg cgc gta       1355
Ala Leu Thr Thr Pro Val Lys Gln Gln Gln Gln Gln Gln Leu Arg Val
            20                  25                  30 ggc gcg gcg tcg gca cgg ctg gcg gcc gcg gcg ttc tcg tcc ggc acg       1403
Gly Ala Ala Ser Ala Arg Leu Ala Ala Ala Ala Phe Ser Ser Gly Thr
        35                  40                  45 ggc gga gac gcg gcc aag aag gcg gcc gcg gcg agg gcg ttc tcc acg       1451
Gly Gly Asp Ala Ala Lys Lys Ala Ala Ala Ala Arg Ala Phe Ser Thr
    50                  55                  60 gga cgc ggc ccc aac gcg aca cgc gag aag agc tcg ctg gcc acg gtc       1499
Gly Arg Gly Pro Asn Ala Thr Arg Glu Lys Ser Ser Leu Ala Thr Val
65                  70                  75                  80 cag gcg gcg acg gac gat gcg cgc ttc gtc ggc ctg acc ggc gcc caa       1547
Gln Ala Ala Thr Asp Asp Ala Arg Phe Val Gly Leu Thr Gly Ala Gln
                85                  90                  95 atc ttt cat gag ctc atg cgc gag cac cag gtg gac acc atc ttt ggc       1595
Ile Phe His Glu Leu Met Arg Glu His Gln Val Asp Thr Ile Phe Gly
            100                 105                 110 tac cct ggc ggc gcc att ctg ccc gtt ttt gat gcc att ttt gag agt       1643
Tyr Pro Gly Gly Ala Ile Leu Pro Val Phe Asp Ala Ile Phe Glu Ser
        115                 120                 125 gac gcc ttc aag ttc att ctc gct cgc cac gag cag ggc gcc ggc cac       1691
Asp Ala Phe Lys Phe Ile Leu Ala Arg His Glu Gln Gly Ala Gly His
    130                 135                 140 atg gcc gag ggc tac gcg cgc gcc acg ggc aag ccc ggc gtt gtc ctc       1739
Met Ala Glu Gly Tyr Ala Arg Ala Thr Gly Lys Pro Gly Val Val Leu
145                 150                 155                 160 gtc acc tcg ggc cct gga gcc acc aac acc atc acc ccg atc atg gat       1787
Val Thr Ser Gly Pro Gly Ala Thr Asn Thr Ile Thr Pro Ile Met Asp
                165                 170                 175 gct tac atg gac ggt acg ccg ctg ctc gtg ttc acc ggc cag gtg cag       1835
Ala Tyr Met Asp Gly Thr Pro Leu Leu Val Phe Thr Gly Gln Val Gln
            180                 185                 190 acc tct gct gtc ggc acg gac gct ttc cag gag tgt gac att gtt ggc       1883
Thr Ser Ala Val Gly Thr Asp Ala Phe Gln Glu Cys Asp Ile Val Gly
        195                 200                 205 atc agc cgc gcg tgc acc aag tgg aac gtc atg gtc aag gac gtg aag       1931
Ile Ser Arg Ala Cys Thr Lys Trp Asn Val Met Val Lys Asp Val Lys
    210                 215                 220
```

```
gag ctc ccg cgc cgc atc aat gag gcc ttt gag att gcc atg agc ggc    1979
Glu Leu Pro Arg Arg Ile Asn Glu Ala Phe Glu Ile Ala Met Ser Gly
225                 230                 235                 240 cgc ccg ggt ccc gtg ctc gtc gat ctt cct aag gat gtg acc gcc gtt    2027
Arg Pro Gly Pro Val Leu Val Asp Leu Pro Lys Asp Val Thr Ala Val
                245                 250                 255 gag ctc aag gaa atg ccc gac agc tcc ccc cag gtt gct gtg cgc cag    2075
Glu Leu Lys Glu Met Pro Asp Ser Ser Pro Gln Val Ala Val Arg Gln
            260                 265                 270 aag caa aag gtc gag ctt ttc cac aag gag cgc att ggc gct cct ggc    2123
Lys Gln Lys Val Glu Leu Phe His Lys Glu Arg Ile Gly Ala Pro Gly
        275                 280                 285 acg gcc gac ttc aag ctc att gcc gag atg atc aac cgt gcg gag cga    2171
Thr Ala Asp Phe Lys Leu Ile Ala Glu Met Ile Asn Arg Ala Glu Arg
    290                 295                 300 ccc gtc atc tat gct ggc cag ggt gtc atg cag agc ccg ttg aat ggc    2219
Pro Val Ile Tyr Ala Gly Gln Gly Val Met Gln Ser Pro Leu Asn Gly
305                 310                 315                 320 ccg gct gtg ctc aag gag ttc gcg gag aag gcc aac att ccc gtg acc    2267
Pro Ala Val Leu Lys Glu Phe Ala Glu Lys Ala Asn Ile Pro Val Thr
                325                 330                 335 acc acc atg cag ggt ctc ggc ggc ttt gac gag cgt agt ccc ctc tcc    2315
Thr Thr Met Gln Gly Leu Gly Gly Phe Asp Glu Arg Ser Pro Leu Ser
            340                 345                 350 ctc aag atg ctc ggc atg cac ggc tct gcc tac gcc aac tac tcg atg    2363
Leu Lys Met Leu Gly Met His Gly Ser Ala Tyr Ala Asn Tyr Ser Met
        355                 360                 365 cag aac gcc gat ctt atc ctg gcg ctc ggt gcc cgc ttt gat gat cgt    2411
Gln Asn Ala Asp Leu Ile Leu Ala Leu Gly Ala Arg Phe Asp Asp Arg
    370                 375                 380 gtg acg ggc cgc gtt gac gcc ttt gct ccg gag gct cgc cgt gcc gag    2459
Val Thr Gly Arg Val Asp Ala Phe Ala Pro Glu Ala Arg Arg Ala Glu
385                 390                 395                 400 cgc gag ggc cgc ggt ggc atc gtt cac ttt gag att tcc ccc aag aac    2507
Arg Glu Gly Arg Gly Gly Ile Val His Phe Glu Ile Ser Pro Lys Asn
                405                 410                 415 ctc cac aag gtc gtc cag ccc acc gtc gcg gtc ctc ggc gac gtg gtc    2555
Leu His Lys Val Val Gln Pro Thr Val Ala Val Leu Gly Asp Val Val
            420                 425                 430 gag aac ctc gcc aac gtc acg ccc cac gtg cag cgc cag gag cgc gag    2603
Glu Asn Leu Ala Asn Val Thr Pro His Val Gln Arg Gln Glu Arg Glu
        435                 440                 445 ccg tgg ttt gcg cag atc gcc gat tgg aag gag aag cac cct ttt ctg    2651
Pro Trp Phe Ala Gln Ile Ala Asp Trp Lys Glu Lys His Pro Phe Leu
    450                 455                 460 ctc gag tct gtt gat tcg gac gac aag gtt ctc aag ccg cag cag gtc    2699
Leu Glu Ser Val Asp Ser Asp Asp Lys Val Leu Lys Pro Gln Gln Val
465                 470                 475                 480 ctc acg gag ctt aac aag cag att ctc gag att cag gag aag gac gcc    2747
Leu Thr Glu Leu Asn Lys Gln Ile Leu Glu Ile Gln Glu Lys Asp Ala
                485                 490                 495 gac cag gag gtc tac atc acc acg ggc gtc gga agc cac cag atg cag    2795
Asp Gln Glu Val Tyr Ile Thr Thr Gly Val Gly Ser His Gln Met Gln
            500                 505                 510 gca gcg cag ttc ctt acc tgg acc aag ccg cgc cag tgg atc tcc tcg    2843
Ala Ala Gln Phe Leu Thr Trp Thr Lys Pro Arg Gln Trp Ile Ser Ser
        515                 520                 525 ggt ggc gcc ggc act atg ggc tac ggc ctt ccc tcg gcc att ggc gcc    2891
Gly Gly Ala Gly Thr Met Gly Tyr Gly Leu Pro Ser Ala Ile Gly Ala
    530                 535                 540
```

```
aag att gcc aag ccc gat gct att gtt att gac atc gat ggt gat gct    2939
Lys Ile Ala Lys Pro Asp Ala Ile Val Ile Asp Ile Asp Gly Asp Ala
545                 550                 555                 560 tct tat tcg atg acc ggt atg gaa ttg atc aca gca gcc gaa ttc aag    2987
Ser Tyr Ser Met Thr Gly Met Glu Leu Ile Thr Ala Ala Glu Phe Lys
                565                 570                 575 gtt ggc gtg aag att ctt ctt ttg cag aac aac ttt cag ggc atg gtc    3035
Val Gly Val Lys Ile Leu Leu Leu Gln Asn Asn Phe Gln Gly Met Val
            580                 585                 590 aag aac tgg cag gat ctc ttt tac gac aag cgc tac tcg ggc acc gcc    3083
Lys Asn Trp Gln Asp Leu Phe Tyr Asp Lys Arg Tyr Ser Gly Thr Ala
        595                 600                 605 atg ttc aac ccg cgc ttc gac aag gtc gcc gat gcg atg cgt gcc aag    3131
Met Phe Asn Pro Arg Phe Asp Lys Val Ala Asp Ala Met Arg Ala Lys
    610                 615                 620 ggt ctc tac tgc gcg aaa cag tcg gag ctc aag gac aag atc aag gag    3179
Gly Leu Tyr Cys Ala Lys Gln Ser Glu Leu Lys Asp Lys Ile Lys Glu
625                 630                 635                 640 ttt ctc gag tac gat gag ggt ccc gtc ctc ctc gag gtt ttc gtg gac    3227
Phe Leu Glu Tyr Asp Glu Gly Pro Val Leu Leu Glu Val Phe Val Asp
                645                 650                 655 aag gac acg ctc gtc ttg ccc atg gtc ccc gct ggc ttt ccg ctc cac    3275
Lys Asp Thr Leu Val Leu Pro Met Val Pro Ala Gly Phe Pro Leu His
            660                 665                 670 gag atg gtc ctc gag cct cct aag ccc aag gac gcc taa gttctttttt    3324
Glu Met Val Leu Glu Pro Pro Lys Pro Lys Asp Ala
        675                 680 ccatggcggg cgagcgagcg agcgcgcgag cgcgcaagtg cgcaagcgcc ttgccttgct    3384
ttgcttcgct tcgctttgct ttgcttcaca caacctaagt atgaattcaa gttttcttgc    3444
ttgtcggcga tgcctgcctg ccaaccagcc agccatccgg ccggccgtcc ttgacgcctt    3504
cgcttccggc gcggccatcg attcaattca cccatccgat acgttccgcc ccctcacgtc    3564
cgtctgcgca cgacccctgc acgaccacgc caaggccaac gcgccgctca gctcagcttg    3624
tcgacgagtc gcacgtcaca tatctcagat gcatttggac tgtgagtgtt attatgccac    3684
tagcacgcaa cgatcttcgg ggtcctcgct cattgcatcc gttcgggccc tgcaggcgtg    3744
gacgcgagtc gccgccgaga cgctgcagca ggccgctccg acgcgagggc tcgagctcgc    3804
cgcgcccgcg cgatgtctgc ctggcgccga ctgatctctg gagcgcaagg aagacacggc    3864
gacgcgagga ggaccgaaga gagacgctgg ggtatgcagg atatacccgg ggcgggacat    3924
tcgttccgca tacactcccc cattcgagct tgctcgtcct tggcagagcc gagcgcgaac    3984
ggttccgaac gcggcaagga ttttggctct ggtgggtgga ctccgatcga ggcgcaggtt    4044
ctccgcaggt tctcgcaggc cggcagtggt cgttagaaat agggagtgcc ggagtcttga    4104
cgcgccttag ctcactctcc gcccacgcgc gcatcgccgc catgccgccg tcccgtctgt    4164
cgctgcgctg gccgcgaccg gctgcgccag agtacgacag tgggacagag ctcgaggcga    4224
cgcgaatcgc tcgggttgta agggtttcaa gggtcgggcg tcgtcgcgtg ccaaagtgaa    4284
aatagtaggg ggggggggg gtacccaccc cgggcaggtt ctcctcgcca gcctaagtgc    4344
ctaagggagc gtaggggttt cgttgaccag agaagcggag aacctgccgc ggcgcggaga    4404
acctatcggg ggagaacttg ccaggcgcga ggcagttctc caatttgcgg acagcggcgc    4464
gcccacgcga ggcggccgcg tggcgataca gcgaggcgac cgcgcggggc cgcgtggcga    4524
cacagctgcg cgcggagtcg gctgcgagaa ggcttctcgc tggcttggtt ggggtcgcgg    4584
```

```
gtggcagggg atggatgccc aggtacgtcg gcgtgcgcgc gcccagggag aaaaggacag    4644
acgcgcgggc ctgcgatgcg agcacgcgat gcgagcacgc gatgcgagca cgcgatgcga    4704
gcacgcgagc gagcgcccga gcaaatgcca cggaacacgc gttttttgtt tggtgatttc    4764
tatgtatgcg gggagacttc gatggccgaa agggtgcaa ggccaaaaga tgctgacagc     4824
ttcgatcggt ctacgcgcg agcaggaaag ggagcaaggg gcggaattct tctgccttga     4884
cccgggggat ccactagttc tagagcggcc gccaccgcgg tggagctcca attcgcccta    4944
tagtgagtcg tattacgcgc gctcactggc cgtcgtttta caacgtcgtg actgggaaaa    5004
ccctggcgtt acccaactta atcgccttgc agcacatccc cctttcgcca gctggcgtaa    5064
tagcgaagag gcccgcaccg atcgcccttc ccaacagttg cgcagcctga atggcgaatg    5124
ggacgcgccc tgtagcggcg cattaagcgc ggcgggtgtg gtggttacgc gcagcgtgac    5184
cgctacactt gccagcgccc tagcgcccgc tcctttcgct ttcttccctt cctttctcgc    5244
cacgttcgcc ggctttcccc gtcaagctct aaatcggggg ctcccttag ggttccgatt     5304 tagtgcttta cggcacctcg accccaaaaa acttgattag ggtgatggtt cacgtagtgg    5364
gccatcgccc tgatagacgg ttttcgccc tttgacgttg gagtccacgt tctttaatag     5424
tggactcttg ttccaaactg gaacaacact caaccctatc tcggtctatt cttttgattt    5484
ataagggatt ttgccgattt cggcctattg gttaaaaaat gagctgattt aacaaaatt     5544 taacgcgaat tttaacaaaa tattaacgct tacaatttag gtggcacttt tcggggaaat    5604
gtgcgcggaa cccctatttg tttatttttc taaatacatt caaatatgta tccgctcatg    5664
agacaataac cctgataaat gcttcaataa tattgaaaaa ggaagagtat gagtattcaa    5724
catttccgtg tcgcccttat tccctttttt gcggcatttt gccttcctgt ttttgctcac    5784
ccagaaacgc tggtgaaagt aaaagatgct gaagatcagt tgggtgcacg agtgggttac    5844
atcgaactgg atctcaacag cggtaagatc cttgagagtt ttcgccccga gaacgtttt     5904 ccaatgatga gcacttttaa agttctgcta tgtggcgcgg tattatcccg tattgacgcc    5964
gggcaagagc aactcggtcg ccgcatacac tattctcaga atgacttggt tgagtactca    6024
ccagtcacag aaaagcatct tacggatggc atgacagtaa gagaattatg cagtgctgcc    6084
ataaccatga gtgataacac tgcggccaac ttacttctga caacgatcgg aggaccgaag    6144
gagctaaccg cttttttgca caacatgggg gatcatgtaa ctcgccttga tcgttgggaa    6204
ccggagctga atgaagccat accaaacgac gagcgtgaca ccacgatgcc tgtagcaatg    6264
gcaacaacgt tgcgcaaact attaactggc gaactactta ctctagcttc ccggcaacaa    6324
ttaatagact ggatggaggc ggataaagtt gcaggaccac ttctgcgctc ggcccttccg    6384
gctggctggt ttattgctga taaatctgga gccggtgagc gtgggtctcg cggtatcatt    6444
gcagcactgg ggccagatgg taagccctcc cgtatcgtag ttatctacac gacggggagt    6504
caggcaacta tggatgaacg aaatagacag atcgctgaga taggtgcctc actgattaag    6564
cattggtaac tgtcagacca agtttactca tatatacttt agattgattt aaaacttcat    6624
ttttaattta aaaggatcta ggtgaagatc cttttgata atctcatgac caaatccct     6684 taacgtgagt tttcgttcca ctgagcgtca gaccccgtag aaaagatcaa aggatcttct    6744
tgagatcctt ttttctgcg cgtaatctgc tgcttgcaaa caaaaaaacc accgctacca     6804
gcggtggttt gtttgccgga tcaagagcta ccaactcttt ttccgaaggt aactggcttc    6864
agcagagcgc agataccaaa tactgtcctt ctagtgtagc cgtagttagg ccaccacttc    6924
aagaactctg tagcaccgcc tacatacctc gctctgctaa tcctgttacc agtggctgct    6984
```

-continued

```
gccagtggcg ataagtcgtg tcttaccggg ttggactcaa gacgatagtt accggataag    7044
gcgcagcggt cgggctgaac ggggggttcg tgcacacagc ccagcttgga gcgaacgacc    7104
tacaccgaac tgagatacct acagcgtgag ctatgagaaa gcgccacgct tcccgaaggg    7164
agaaaggcgg acaggtatcc ggtaagcggc agggtcggaa caggagagcg cacgagggag    7224
cttccagggg gaaacgcctg gtatctttat agtcctgtcg ggtttcgcca cctctgactt    7284
gagcgtcgat ttttgtgatg ctcgtcaggg gggcggagcc tatggaaaaa cgccagcaac    7344
gcggcctttt tacggttcct ggccttttgc tggccttttg ctcacatgtt ctttcctgcg    7404
ttatcccctg attctgtgga taaccgtatt accgcctttg agtgagctga taccgctcgc    7464
cgcagccgaa cgaccgagcg cagcgagtca gtgagcgagg aagcggaaga gcgcccaata    7524
cgcaaaccgc ctctccccgc gcgttggccg attcattaat gcagctggca cgacaggttt    7584
cccgactgga agcgggcag tgagcgcaac gcaattaatg tgagttagct cactcattag    7644
gcaccccagg ctttacactt tatgcttccg gctcgtatgt tgtgtggaat tgtgagcgga    7704
taacaatttc acacaggaaa cagctatgac catgattacg ccaagcgcgc aattaaccct    7764
cactaagggg aacaaaagct gggtaccggg ccccccctcg aggtcgacgg tatcgataag    7824
cttgacgtcg aattcctgca gcc                                           7847
```

<210> SEQ ID NO 22
<211> LENGTH: 684
<212> TYPE: PRT
<213> ORGANISM: Schizochytrium sp.

<400> SEQUENCE: 22

Met Ser Ala Thr Arg Ala Ala Thr Arg Thr Ala Ala Leu Ser Ser
1               5                   10                  15

Ala Leu Thr Thr Pro Val Lys Gln Gln Gln Gln Gln Leu Arg Val
            20                  25                  30

Gly Ala Ala Ser Ala Arg Leu Ala Ala Ala Phe Ser Ser Gly Thr
        35                  40                  45

Gly Gly Asp Ala Ala Lys Lys Ala Ala Ala Arg Ala Phe Ser Thr
    50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
            100                 105                 110

Tyr Pro Gly Gly Ala Ile Leu Pro Val Phe Asp Ala Ile Phe Glu Ser
        115                 120                 125

Asp Ala Phe Lys Phe Ile Leu Ala Arg His Glu Gln Gly Ala Gly His
    130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Gln
            180                 185                 190

Thr Ser Ala Val Gly Thr Asp Ala Phe Gln Glu Cys Asp Ile Val Gly
        195                 200                 205

Ile Ser Arg Ala Cys Thr Lys Trp Asn Val Met Val Lys Asp Val Lys

-continued

```
            210                 215                 220
Glu Leu Pro Arg Arg Ile Asn Glu Ala Phe Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
                260                 265                 270

Lys Gln Lys Val Glu Leu Phe His Lys Glu Arg Ile Gly Ala Pro Gly
                275                 280                 285

Thr Ala Asp Phe Lys Leu Ile Ala Glu Met Ile Asn Arg Ala Glu Arg
290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335

Thr Thr Met Gln Gly Leu Gly Gly Phe Asp Glu Arg Ser Pro Leu Ser
                340                 345                 350

Leu Lys Met Leu Gly Met His Gly Ser Ala Tyr Ala Asn Tyr Ser Met
                355                 360                 365

Gln Asn Ala Asp Leu Ile Leu Ala Leu Gly Ala Arg Phe Asp Asp Arg
370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
                420                 425                 430

Glu Asn Leu Ala Asn Val Thr Pro His Val Gln Arg Gln Glu Arg Glu
                435                 440                 445

Pro Trp Phe Ala Gln Ile Ala Asp Trp Lys Glu Lys His Pro Phe Leu
                450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
                485                 490                 495

Asp Gln Glu Val Tyr Ile Thr Thr Gly Val Gly Ser His Gln Met Gln
                500                 505                 510

Ala Ala Gln Phe Leu Thr Trp Thr Lys Pro Arg Gln Trp Ile Ser Ser
                515                 520                 525

Gly Gly Ala Gly Thr Met Gly Tyr Gly Leu Pro Ser Ala Ile Gly Ala
                530                 535                 540

Lys Ile Ala Lys Pro Asp Ala Ile Val Ile Asp Ile Asp Gly Asp Ala
545                 550                 555                 560

Ser Tyr Ser Met Thr Gly Met Glu Leu Ile Thr Ala Ala Glu Phe Lys
                565                 570                 575

Val Gly Val Lys Ile Leu Leu Leu Gln Asn Asn Phe Gln Gly Met Val
                580                 585                 590

Lys Asn Trp Gln Asp Leu Phe Tyr Asp Lys Arg Tyr Ser Gly Thr Ala
                595                 600                 605

Met Phe Asn Pro Arg Phe Asp Lys Val Ala Asp Ala Met Arg Ala Lys
                610                 615                 620

Gly Leu Tyr Cys Ala Lys Gln Ser Glu Leu Lys Asp Lys Ile Lys Glu
625                 630                 635                 640
```

```
Phe Leu Glu Tyr Asp Glu Gly Pro Val Leu Glu Val Phe Val Asp
                645                 650                 655

Lys Asp Thr Leu Val Leu Pro Met Val Pro Ala Gly Phe Pro Leu His
            660                 665                 670

Glu Met Val Leu Glu Pro Pro Lys Pro Lys Asp Ala
        675                 680

<210> SEQ ID NO 23
<211> LENGTH: 7847
<212> TYPE: DNA
<213> ORGANISM: Schizochytrium sp.
<220> FEATURE:
<221> NAME/KEY: prim_transcript
<222> LOCATION: (1)..(1259)
<223> OTHER INFORMATION:
<220> FEATURE:
<221> NAME/KEY: CDS
<222> LOCATION: (1260)..(3314)
<223> OTHER INFORMATION:
<220> FEATURE:
<221> NAME/KEY: prim_transcript
<222> LOCATION: (3315)..(4887)
<223> OTHER INFORMATION:
<220> FEATURE:
<221> NAME/KEY: mutation
<222> LOCATION: (1834)..(1835)
<223> OTHER INFORMATION:
<220> FEATURE:
<221> NAME/KEY: mutation
<222> LOCATION: (3042)..(3044)
<223> OTHER INFORMATION:

<400> SEQUENCE: 23
ttgtcgacag caacttgcaa gttatacgcg accaccaggc aatctcagca cgcccagcga      60
gcacggagct tgcgaagagg gtttacaagt cgtcgttcat tcgctctcaa gctttgcctc     120
aacgcaacta ggcccaggcc tactttcact gtgtcttgtc ttgcctttca caccgaccga     180
gtgtgcacaa ccgtgttttg cacaaagcgc aagatgctca ctcgactgtg aagaaaggtt     240
gcgcgcaagc gactgcgact gcgaggatga ggatgactgg cagcctgttc aaaaactgaa     300
aatccgcgat gggtcagtgc cattcgcgca tgacgcctgc gagagacaag ttaactcgtg     360
tcactggcat gtcctagcat cttttacgcga gcaaaattca atcgctttat tttttcagtt     420
tcgtaacctt ctcgcaaccg cgaatcgccg tttcagcctg actaatctgc agctgcgtgg     480
cactgtcagt cagtcagtca gtcgtgcgcg ctgttccagc accgaggtcg cgcgtcgccg     540
cgcctggacc gctgctgcta ctgctagtgg cacggcaggt aggagcttgt tgccggaaca     600
ccagcagccg ccagtcgacg ccagccaggg gaaagtccgg cgtcgaaggg agaggaaggc     660
ggcgtgtgca aactaacgtt gaccactggc gcccgccgac acgagcagga agcaggcagc     720
tgcagagcgc agcgcgcaag tgcagaatgc gcgaaagatc cacttgcgcg cggcgggcgc     780
gcacttgcgg gcgcggcgcg aacagtgcg gaaggagcg gtgcagacgg cgcgcagtga     840
cagtgggcgc aaagccgcgc agtaagcagc ggcggggaac ggtatacgca gtgccgcggg     900
ccgccgcaca cagaagtata cgcgggccga agtgggcgt cgcgcgcggg aagtgcggaa     960
tggcgggcaa ggaaaggagg agacggaaag agggcgggaa agagagagag agagagtgaa    1020
aaaagaaaga aagaaagaaa gaaagaaaga agctcggag ccacgccgcg gggagagaga    1080
gaaatgaaag cacggcacgg caaagcaaag caaagcagac ccagccagac ccagccgagg    1140
gaggagcgcg cgcaggaccc gcgcggcgag cgagcgagca cggcgcgcga gcagcgagc    1200 gagcgagcgc gcgagcgagc aaggcttgct gcgagcgatc gagcgagcga gcgggaagg    1259
```

-continued

| | | | | | | | | | | | | | | | | |
|---|---|---|---|---|---|---|---|---|---|---|---|---|---|---|---|---|
| atg | agc | gcg | acc | cgc | gcg | gcg | acg | agg | aca | gcg | gcg | gcg | ctg | tcc | tcg | 1307 |
| Met | Ser | Ala | Thr | Arg | Ala | Ala | Thr | Arg | Thr | Ala | Ala | Ala | Leu | Ser | Ser | |
| 1 | | | | 5 | | | | | 10 | | | | | 15 | | |
| gcg | ctg | acg | acg | cct | gta | aag | cag | cag | cag | cag | cag | ctg | cgc | gta | | 1355 |
| Ala | Leu | Thr | Thr | Pro | Val | Lys | Gln | Gln | Gln | Gln | Gln | Leu | Arg | Val | | |
| | | | 20 | | | | | 25 | | | | | 30 | | | |
| ggc | gcg | gcg | tcg | gca | cgg | ctg | gcg | gcc | gcg | gcg | ttc | tcg | tcc | ggc | acg | 1403 |
| Gly | Ala | Ala | Ser | Ala | Arg | Leu | Ala | Ala | Ala | Ala | Phe | Ser | Ser | Gly | Thr | |
| | 35 | | | | 40 | | | | | 45 | | | | | | |
| ggc | gga | gac | gcg | gcc | aag | aag | gcg | gcc | gcg | gcg | agg | gcg | ttc | tcc | acg | 1451 |
| Gly | Gly | Asp | Ala | Ala | Lys | Lys | Ala | Ala | Ala | Ala | Arg | Ala | Phe | Ser | Thr | |
| 50 | | | | 55 | | | | | 60 | | | | | | | |
| gga | cgc | ggc | ccc | aac | gcg | aca | cgc | gag | aag | agc | tcg | ctg | gcc | acg | gtc | 1499 |
| Gly | Arg | Gly | Pro | Asn | Ala | Thr | Arg | Glu | Lys | Ser | Ser | Leu | Ala | Thr | Val | |
| 65 | | | | 70 | | | | | 75 | | | | | 80 | | |
| cag | gcg | gcg | acg | gac | gat | gcg | cgc | ttc | gtc | ggc | ctg | acc | ggc | gcc | caa | 1547 |
| Gln | Ala | Ala | Thr | Asp | Asp | Ala | Arg | Phe | Val | Gly | Leu | Thr | Gly | Ala | Gln | |
| | | | | 85 | | | | | 90 | | | | | 95 | | |
| atc | ttt | cat | gag | ctc | atg | cgc | gag | cac | cag | gtg | gac | acc | atc | ttt | ggc | 1595 |
| Ile | Phe | His | Glu | Leu | Met | Arg | Glu | His | Gln | Val | Asp | Thr | Ile | Phe | Gly | |
| | | | 100 | | | | | 105 | | | | | 110 | | | |
| tac | cct | ggc | ggc | gcc | att | ctg | ccc | gtt | ttt | gat | gcc | att | ttt | gag | agt | 1643 |
| Tyr | Pro | Gly | Gly | Ala | Ile | Leu | Pro | Val | Phe | Asp | Ala | Ile | Phe | Glu | Ser | |
| | | 115 | | | | | 120 | | | | | 125 | | | | |
| gac | gcc | ttc | aag | ttc | att | ctc | gct | cgc | cac | gag | cag | ggc | gcc | ggc | cac | 1691 |
| Asp | Ala | Phe | Lys | Phe | Ile | Leu | Ala | Arg | His | Glu | Gln | Gly | Ala | Gly | His | |
| | 130 | | | | | 135 | | | | | 140 | | | | | |
| atg | gcc | gag | ggc | tac | gcg | cgc | gcc | acg | ggc | aag | ccc | ggc | gtt | gtc | ctc | 1739 |
| Met | Ala | Glu | Gly | Tyr | Ala | Arg | Ala | Thr | Gly | Lys | Pro | Gly | Val | Val | Leu | |
| 145 | | | | | 150 | | | | | 155 | | | | | 160 | |
| gtc | acc | tcg | ggc | cct | gga | gcc | acc | aac | acc | atc | acc | ccg | atc | atg | gat | 1787 |
| Val | Thr | Ser | Gly | Pro | Gly | Ala | Thr | Asn | Thr | Ile | Thr | Pro | Ile | Met | Asp | |
| | | | | 165 | | | | | 170 | | | | | 175 | | |
| gct | tac | atg | gac | ggt | acg | ccg | ctg | ctc | gtg | ttc | acc | ggc | cag | gtg | cag | 1835 |
| Ala | Tyr | Met | Asp | Gly | Thr | Pro | Leu | Leu | Val | Phe | Thr | Gly | Gln | Val | Gln | |
| | | | 180 | | | | | 185 | | | | | 190 | | | |
| acc | tct | gct | gtc | ggc | acg | gac | gct | ttc | cag | gag | tgt | gac | att | gtt | ggc | 1883 |
| Thr | Ser | Ala | Val | Gly | Thr | Asp | Ala | Phe | Gln | Glu | Cys | Asp | Ile | Val | Gly | |
| | | 195 | | | | | 200 | | | | | 205 | | | | |
| atc | agc | cgc | gcg | tgc | acc | aag | tgg | aac | gtc | atg | gtc | aag | gac | gtg | aag | 1931 |
| Ile | Ser | Arg | Ala | Cys | Thr | Lys | Trp | Asn | Val | Met | Val | Lys | Asp | Val | Lys | |
| | 210 | | | | | 215 | | | | | 220 | | | | | |
| gag | ctc | ccg | cgc | cgc | atc | aat | gag | gcc | ttt | gag | att | gcc | atg | agc | ggc | 1979 |
| Glu | Leu | Pro | Arg | Arg | Ile | Asn | Glu | Ala | Phe | Glu | Ile | Ala | Met | Ser | Gly | |
| 225 | | | | | 230 | | | | | 235 | | | | | 240 | |
| cgc | ccg | ggt | ccc | gtg | ctc | gtc | gat | ctt | cct | aag | gat | gtg | acc | gcc | gtt | 2027 |
| Arg | Pro | Gly | Pro | Val | Leu | Val | Asp | Leu | Pro | Lys | Asp | Val | Thr | Ala | Val | |
| | | | | 245 | | | | | 250 | | | | | 255 | | |
| gag | ctc | aag | gaa | atg | ccc | gac | agc | tcc | ccc | cag | gtt | gct | gtg | cgc | cag | 2075 |
| Glu | Leu | Lys | Glu | Met | Pro | Asp | Ser | Ser | Pro | Gln | Val | Ala | Val | Arg | Gln | |
| | | | | 260 | | | | | 265 | | | | | 270 | | |
| aag | caa | aag | gtc | gag | ctt | ttc | cac | aag | gag | cgc | att | ggc | gct | cct | ggc | 2123 |
| Lys | Gln | Lys | Val | Glu | Leu | Phe | His | Lys | Glu | Arg | Ile | Gly | Ala | Pro | Gly | |
| | | 275 | | | | | 280 | | | | | 285 | | | | |
| acg | gcc | gac | ttc | aag | ctc | att | gcc | gag | atg | atc | aac | cgt | gcg | gag | cga | 2171 |
| Thr | Ala | Asp | Phe | Lys | Leu | Ile | Ala | Glu | Met | Ile | Asn | Arg | Ala | Glu | Arg | |
| | 290 | | | | | 295 | | | | | 300 | | | | | |
| ccc | gtc | atc | tat | gct | ggc | cag | ggt | gtc | atg | cag | agc | ccg | ttg | aat | ggc | 2219 |
| Pro | Val | Ile | Tyr | Ala | Gly | Gln | Gly | Val | Met | Gln | Ser | Pro | Leu | Asn | Gly | |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 305 |     |     |     | 310 |     |     |     | 315 |     |     |     | 320 |     |      |
| ccg | gct | gtg | ctc | aag | gag | ttc | gcg | gag | aag | gcc | aac | att | ccc | gtg | acc | 2267 |
| Pro | Ala | Val | Leu | Lys | Glu | Phe | Ala | Glu | Lys | Ala | Asn | Ile | Pro | Val | Thr |      |
|     |     |     |     | 325 |     |     |     | 330 |     |     |     | 335 |     |     |     |      |
| acc | acc | atg | cag | ggt | ctc | ggc | ggc | ttt | gac | gag | cgt | agt | ccc | ctc | tcc | 2315 |
| Thr | Thr | Met | Gln | Gly | Leu | Gly | Gly | Phe | Asp | Glu | Arg | Ser | Pro | Leu | Ser |      |
|     |     |     | 340 |     |     |     | 345 |     |     |     | 350 |     |     |     |     |      |
| ctc | aag | atg | ctc | ggc | atg | cac | ggc | tct | gcc | tac | gcc | aac | tac | tcg | atg | 2363 |
| Leu | Lys | Met | Leu | Gly | Met | His | Gly | Ser | Ala | Tyr | Ala | Asn | Tyr | Ser | Met |      |
|     |     | 355 |     |     |     | 360 |     |     |     | 365 |     |     |     |     |     |      |
| cag | aac | gcc | gat | ctt | atc | ctg | gcg | ctc | ggt | gcc | cgc | ttt | gat | gat | cgt | 2411 |
| Gln | Asn | Ala | Asp | Leu | Ile | Leu | Ala | Leu | Gly | Ala | Arg | Phe | Asp | Asp | Arg |      |
|     | 370 |     |     |     | 375 |     |     |     | 380 |     |     |     |     |     |     |      |
| gtg | acg | ggc | cgc | gtt | gac | gcc | ttt | gct | ccg | gag | gct | cgc | cgt | gcc | gag | 2459 |
| Val | Thr | Gly | Arg | Val | Asp | Ala | Phe | Ala | Pro | Glu | Ala | Arg | Arg | Ala | Glu |      |
| 385 |     |     |     |     | 390 |     |     |     |     | 395 |     |     |     |     | 400 |      |
| cgc | gag | ggc | cgc | ggt | ggc | atc | gtt | cac | ttt | gag | att | tcc | ccc | aag | aac | 2507 |
| Arg | Glu | Gly | Arg | Gly | Gly | Ile | Val | His | Phe | Glu | Ile | Ser | Pro | Lys | Asn |      |
|     |     |     |     | 405 |     |     |     | 410 |     |     |     | 415 |     |     |     |      |
| ctc | cac | aag | gtc | gtc | cag | ccc | acc | gtc | gcg | gtc | ctc | ggc | gac | gtg | gtc | 2555 |
| Leu | His | Lys | Val | Val | Gln | Pro | Thr | Val | Ala | Val | Leu | Gly | Asp | Val | Val |      |
|     |     |     | 420 |     |     |     | 425 |     |     |     | 430 |     |     |     |     |      |
| gag | aac | ctc | gcc | aac | gtc | acg | ccc | cac | gtg | cag | cgc | cag | gag | cgc | gag | 2603 |
| Glu | Asn | Leu | Ala | Asn | Val | Thr | Pro | His | Val | Gln | Arg | Gln | Glu | Arg | Glu |      |
|     |     | 435 |     |     |     | 440 |     |     |     | 445 |     |     |     |     |     |      |
| ccg | tgg | ttt | gcg | cag | atc | gcc | gat | tgg | aag | gag | aag | cac | cct | ttt | ctg | 2651 |
| Pro | Trp | Phe | Ala | Gln | Ile | Ala | Asp | Trp | Lys | Glu | Lys | His | Pro | Phe | Leu |      |
|     | 450 |     |     |     | 455 |     |     |     | 460 |     |     |     |     |     |     |      |
| ctc | gag | tct | gtt | gat | tcg | gac | gac | aag | gtt | ctc | aag | ccg | cag | cag | gtc | 2699 |
| Leu | Glu | Ser | Val | Asp | Ser | Asp | Asp | Lys | Val | Leu | Lys | Pro | Gln | Gln | Val |      |
| 465 |     |     |     |     | 470 |     |     |     |     | 475 |     |     |     |     | 480 |      |
| ctc | acg | gag | ctt | aac | aag | cag | att | ctc | gag | att | cag | gag | aag | gac | gcc | 2747 |
| Leu | Thr | Glu | Leu | Asn | Lys | Gln | Ile | Leu | Glu | Ile | Gln | Glu | Lys | Asp | Ala |      |
|     |     |     |     | 485 |     |     |     | 490 |     |     |     | 495 |     |     |     |      |
| gac | cag | gag | gtc | tac | atc | acc | acg | ggc | gtc | gga | agc | cac | cag | atg | cag | 2795 |
| Asp | Gln | Glu | Val | Tyr | Ile | Thr | Thr | Gly | Val | Gly | Ser | His | Gln | Met | Gln |      |
|     |     |     | 500 |     |     |     | 505 |     |     |     | 510 |     |     |     |     |      |
| gca | gcg | cag | ttc | ctt | acc | tgg | acc | aag | ccg | cgc | cag | tgg | atc | tcc | tcg | 2843 |
| Ala | Ala | Gln | Phe | Leu | Thr | Trp | Thr | Lys | Pro | Arg | Gln | Trp | Ile | Ser | Ser |      |
|     |     | 515 |     |     |     | 520 |     |     |     | 525 |     |     |     |     |     |      |
| ggt | ggc | gcc | ggc | act | atg | ggc | tac | ggc | ctt | ccc | tcg | gcc | att | ggc | gcc | 2891 |
| Gly | Gly | Ala | Gly | Thr | Met | Gly | Tyr | Gly | Leu | Pro | Ser | Ala | Ile | Gly | Ala |      |
|     | 530 |     |     |     | 535 |     |     |     | 540 |     |     |     |     |     |     |      |
| aag | att | gcc | aag | ccc | gat | gct | att | gtt | att | gac | atc | gat | ggt | gat | gct | 2939 |
| Lys | Ile | Ala | Lys | Pro | Asp | Ala | Ile | Val | Ile | Asp | Ile | Asp | Gly | Asp | Ala |      |
| 545 |     |     |     |     | 550 |     |     |     |     | 555 |     |     |     |     | 560 |      |
| tct | tat | tcg | atg | acc | ggt | atg | gaa | ttg | atc | aca | gca | gcc | gaa | ttc | aag | 2987 |
| Ser | Tyr | Ser | Met | Thr | Gly | Met | Glu | Leu | Ile | Thr | Ala | Ala | Glu | Phe | Lys |      |
|     |     |     |     | 565 |     |     |     | 570 |     |     |     | 575 |     |     |     |      |
| gtt | ggc | gtg | aag | att | ctt | ctt | ttg | cag | aac | aac | ttt | cag | ggc | atg | gtc | 3035 |
| Val | Gly | Val | Lys | Ile | Leu | Leu | Leu | Gln | Asn | Asn | Phe | Gln | Gly | Met | Val |      |
|     |     |     | 580 |     |     |     | 585 |     |     |     | 590 |     |     |     |     |      |
| aag | aac | gtt | cag | gat | ctc | ttt | tac | gac | aag | cgc | tac | tcg | ggc | acc | gcc | 3083 |
| Lys | Asn | Val | Gln | Asp | Leu | Phe | Tyr | Asp | Lys | Arg | Tyr | Ser | Gly | Thr | Ala |      |
|     |     | 595 |     |     |     | 600 |     |     |     | 605 |     |     |     |     |     |      |
| atg | ttc | aac | ccg | cgc | ttc | gac | aag | gtc | gcc | gat | gcg | atg | cgt | gcc | aag | 3131 |
| Met | Phe | Asn | Pro | Arg | Phe | Asp | Lys | Val | Ala | Asp | Ala | Met | Arg | Ala | Lys |      |
|     | 610 |     |     |     | 615 |     |     |     | 620 |     |     |     |     |     |     |      |
| ggt | ctc | tac | tgc | gcg | aaa | cag | tcg | gag | ctc | aag | gac | aag | atc | aag | gag | 3179 |

```
Gly Leu Tyr Cys Ala Lys Gln Ser Glu Leu Lys Asp Lys Ile Lys Glu
625                 630                 635                 640 ttt ctc gag tac gat gag ggt ccc gtc ctc ctc gag gtt ttc gtg gac        3227
Phe Leu Glu Tyr Asp Glu Gly Pro Val Leu Leu Glu Val Phe Val Asp
                645                 650                 655 aag gac acg ctc gtc ttg ccc atg gtc ccc gct ggc ttt ccg ctc cac        3275
Lys Asp Thr Leu Val Leu Pro Met Val Pro Ala Gly Phe Pro Leu His
            660                 665                 670 gag atg gtc ctc gag cct cct aag ccc aag gac gcc taa gttctttttt        3324
Glu Met Val Leu Glu Pro Pro Lys Pro Lys Asp Ala
        675                 680 ccatggcggg cgagcgagcg agcgcgcgag cgcgcaagtg cgcaagcgcc ttgccttgct     3384
ttgcttcgct tcgctttgct ttgcttcaca caacctaagt atgaattcaa gttttcttgc     3444
ttgtcggcga tgcctgcctg ccaaccagcc agccatccgg ccggccgtcc ttgacgcctt     3504
cgcttccggc gcggccatcg attcaattca cccatccgat acgttccgcc ccctcacgtc     3564
cgtctgcgca cgacccctgc acgaccacgc caaggccaac gcgccgctca gctcagcttg     3624
tcgacgagtc gcacgtcaca tatctcagat gcatttggac tgtgagtgtt attatgccac     3684
tagcacgcaa cgatcttcgg ggtcctcgct cattgcatcc gttcgggccc tgcaggcgtg     3744
gacgcgagtc gccgccgaga cgctgcagca ggccgctccg acgcgagggc tcgagctcgc     3804
cgcgcccgcg cgatgtctgc ctggcgccga ctgatctctg gagcgcaagg aagacacggc     3864
gacgcgagga ggaccgaaga gagacgctgg ggtatgcagg atatacccgg ggcgggacat     3924
tcgttccgca tacactcccc cattcgagct tgctcgtcct tggcagagcc gagcgcgaac     3984
ggttccgaac gcggcaagga ttttggctct ggtgggtgga ctccgatcga ggcgcaggtt     4044
ctccgcaggt tctcgcaggc cggcagtggt cgttagaaat agggagtgcc ggagtcttga     4104
cgcgccttag ctcactctcc gcccacgcgc gcatcgccgc catgccgccg tcccgtctgt     4164
cgctgcgctg gccgcgaccg gctgcgccag agtacgacag tgggacagag ctcgaggcga     4224
cgcgaatcgc tcgggttgta agggtttcaa gggtcgggcg tcgtcgcgtg ccaaagtgaa     4284
aatagtaggg gggggggggg gtacccaccc cgggcaggtt ctcctcgcca gcctaagtgc     4344
ctaagggagc gtaggggttt cgttgaccag agaagcggag aacctgccgc ggcgcggaga     4404
acctatcggc ggagaacttg ccaggcgcga ggcagttctc caatttgcgg acagcggcgc     4464
gcccacgcga ggcggccgcg tggcgataca gcgaggcgac cgcgcggggc gcgtggcga     4524
cacagctgcg cgcggagtcg gctgcgagaa ggcttctcgc tggcttggtt ggggtcgcgg     4584
gtggcagggg atggatgccc aggtacgtcg gcgtgcgcgc gcccagggag aaaaggacag     4644
acgcgcgggc ctgcgatgcg agcacgcgat gcgagcacgc gatgcgagca cgcgatgcga     4704
gcacgcgagc gagcgcccga gcaaatgcca cggaacacgc gttttttgtt tggtgatttc     4764
tatgtatgcg gggagacttc gatggccgaa aggggtgcaa ggccaaaaga tgctgacagc     4824
ttcgatcggt ctacggcgcg agcaggaaag ggagcaaggg gcggaattct tctgccttga     4884
cccgggggat ccactagttc tagagcggcc gccaccgcgg tggagctcca attcgcccta     4944
tagtgagtcg tattacgcgc gctcactggc cgtcgtttta caacgtcgtg actgggaaaa     5004
ccctggcgtt acccaactta atcgccttgc agcacatccc ctttcgcca gctggcgtaa     5064
tagcgaagag gcccgcaccg atcgcccttc ccaacagttg cgcagcctga atggcgaatg     5124
ggacgcgccc tgtagcggcg cattaagcgc ggcgggtgtg gtggttacgc gcagcgtgac     5184
cgctacactt gccagcgccc tagcgcccgc tcctttcgct ttcttccctt cctttctcgc     5244
```

```
cacgttcgcc ggctttcccc gtcaagctct aaatcggggg ctcccttTag ggttccgatt    5304
tagtgcttta cggcacctcg accccaaaaa acttgattag ggtgatggtt cacgtagtgg    5364
gccatcgccc tgatagacgg ttTTtcgccc tttgacgttg gagtccacgt tcTTTaatag    5424
tggactcttg TTccaaactg gaacaacact caaccctatc tcggtctatt cTTTTgaTTT    5484
ataagggaTT ttgccgaTTT cggcctattg gTTaaaaaat gagctgaTTT aacaaaaaTT    5544
taacgcgaat TTTaacaaaa taTTaacgct tacaaTTTag gtggcacTTT tcggggaaat    5604
gtgcgcggaa ccctaTTTtg TTtaTTTTtc taaatacaTT caaatatgta tccgctcatg    5664
agacaataac cctgataaat gcTTcaataa taTTgaaaaa ggaagagtat gagtaTTcaa    5724
caTTtccgtg tcgccTTat tcccTTTTTT gcggcaTTTT gccTTcctgt TTTtgctcac    5784
ccagaaacgc tggtgaaagt aaaagatgct gaagatcagt tgggtgcacg agtgggTTac    5844
atcgaactgg atctcaacag cggtaagatc cTTgagagTT ttcgccccga gaacgTTTT    5904 ccaatgatga gcacTTTTaa agTTctgcta tgtggcgcgg taTTatcccg taTTgacgcc    5964
gggcaagagc aactcggtcg ccgcatacac taTTctcaga atgacTTggt tgagtactca    6024
ccagtcacag aaaagcatct tacggatggc atgacagtaa gagaaTTatg cagtgctgcc    6084
ataaccatga gtgataacac tgcggccaac TTacTTctga caacgatcgg aggaccgaag    6144
gagctaaccg cTTTTTTgca acaTgggg atcatgtaa ctcgccTTga tcgttggaa    6204 ccggagctga atgaagccat accaaacgac gagcgtgaca ccacgatgcc tgtagcaatg    6264
gcaacaacgt tgcgcaaact aTTaactggc gaactacTTa ctctagcTTc ccggcaacaa    6324

TTaatagact ggatggaggc ggataaagTT gcaggaccac TTctgcgctc ggccCTTccg    6384
gctggctggt TTaTTgctga taaatctgga gccggtgagc gtgggtctcg cggtatcaTT    6444
gcagcactgg ggccagatgg taagccctcc cgtatcgtag TTatctacac gacggggagt    6504
caggcaacta tggatgaacg aaatagacag atcgctgaga taggtgcctc actgaTTaag    6564
caTTggtaac tgtcagacca agTTtactca tatatacTTT agaTTgaTTT aaaacTTcat    6624

TTTtaaTTTa aaaggatcta ggtgaagatc cTTTTTgata atctcatgac caaaatccct    6684
taacgtgagt TTtcgttcca ctgagcgtca gaccccgtag aaaagatcaa aggatcTTct    6744
tgagatccTT TTTTtctgcg cgtaatctgc tgcTTgcaaa caaaaaaacc accgctacca    6804
gcggtggTTT gTTtgccgga tcaagagcta ccaactcTTT TTccgaaggt aactggcTTc    6864
agcagagcgc agataccaaa tactgtccTT ctagtgtagc cgtagTTagg ccaccacTTc    6924
aagaactctg tagcaccgcc tacatacctc gctctgctaa tcctgTTacc agtggctgct    6984
gccagtggcg ataagtcgtg tcTTaccggg TTggactcaa gacgatagTT accggataag    7044
gcgcagcggt cgggctgaac ggggggTTcg tgcacacagc ccagcTTgga gcgaacgacc    7104
tacaccgaac tgagatacct acagcgtgag ctatgagaaa gcgccacgct tcccgaaggg    7164
agaaaggcgg acaggtatcc ggtaagcggc agggtcggaa caggagagcg cacgagggag    7224
cTTccagggg gaaacgcctg gtatcTTTat agtcctgtcg ggTTtcgcca cctctgacTT    7284
gagcgtcgat TTTtgtgatg ctcgtcaggg ggcggagcc tatggaaaaa cgccagcaac    7344 gcggccTTT tacggTTcct ggccTTTTgc tggccTTTTg ctcacatgTT cTTTcctgcg    7404

TTatccCCTg aTTctgtgga taaccgtaTT accgccTTTg agtgagctga taccgctcgc    7464
cgcagccgaa cgaccgagcg cagcgagtca gtgagcgagg aagcggaaga gcgcccaata    7524
cgcaaaccgc ctctccccgc gcgTTggccg aTTcaTTaat gcagctgca cgacaggTTT    7584 cccgactgga aagcgggcag tgagcgcaac gcaaTTaatg tgagTTagct cactcaTTag    7644
```

```
gcaccccagg ctttacactt tatgcttccg gctcgtatgt tgtgtggaat tgtgagcgga    7704
taacaatttc acacaggaaa cagctatgac catgattacg ccaagcgcgc aattaaccct    7764
cactaaaggg aacaaaagct gggtaccggg ccccccctcg aggtcgacgg tatcgataag    7824
cttgacgtcg aattcctgca gcc                                            7847
```

<210> SEQ ID NO 24
<211> LENGTH: 684
<212> TYPE: PRT
<213> ORGANISM: Schizochytrium sp.

<400> SEQUENCE: 24

```
Met Ser Ala Thr Arg Ala Ala Thr Arg Thr Ala Ala Leu Ser Ser
1               5                   10                  15

Ala Leu Thr Thr Pro Val Lys Gln Gln Gln Gln Gln Leu Arg Val
                20                  25                  30

Gly Ala Ala Ser Ala Arg Leu Ala Ala Ala Phe Ser Ser Gly Thr
            35                  40                  45

Gly Gly Asp Ala Ala Lys Lys Ala Ala Ala Arg Ala Phe Ser Thr
50                  55                  60

Gly Arg Gly Pro Asn Ala Thr Arg Glu Lys Ser Ser Leu Ala Thr Val
65                  70                  75                  80

Gln Ala Ala Thr Asp Asp Ala Arg Phe Val Gly Leu Thr Gly Ala Gln
                85                  90                  95

Ile Phe His Glu Leu Met Arg Glu His Gln Val Asp Thr Ile Phe Gly
            100                 105                 110

Tyr Pro Gly Gly Ala Ile Leu Pro Val Phe Asp Ala Ile Phe Glu Ser
        115                 120                 125

Asp Ala Phe Lys Phe Ile Leu Ala Arg His Glu Gln Gly Ala Gly His
130                 135                 140

Met Ala Glu Gly Tyr Ala Arg Ala Thr Gly Lys Pro Gly Val Val Leu
145                 150                 155                 160

Val Thr Ser Gly Pro Gly Ala Thr Asn Thr Ile Thr Pro Ile Met Asp
                165                 170                 175

Ala Tyr Met Asp Gly Thr Pro Leu Leu Val Phe Thr Gly Gln Val Gln
            180                 185                 190

Thr Ser Ala Val Gly Thr Asp Ala Phe Gln Glu Cys Asp Ile Val Gly
        195                 200                 205

Ile Ser Arg Ala Cys Thr Lys Trp Asn Val Met Val Lys Asp Val Lys
210                 215                 220

Glu Leu Pro Arg Arg Ile Asn Glu Ala Phe Glu Ile Ala Met Ser Gly
225                 230                 235                 240

Arg Pro Gly Pro Val Leu Val Asp Leu Pro Lys Asp Val Thr Ala Val
                245                 250                 255

Glu Leu Lys Glu Met Pro Asp Ser Ser Pro Gln Val Ala Val Arg Gln
            260                 265                 270

Lys Gln Lys Val Glu Leu Phe His Lys Glu Arg Ile Gly Ala Pro Gly
        275                 280                 285

Thr Ala Asp Phe Lys Leu Ile Ala Glu Met Ile Asn Arg Ala Glu Arg
290                 295                 300

Pro Val Ile Tyr Ala Gly Gln Gly Val Met Gln Ser Pro Leu Asn Gly
305                 310                 315                 320

Pro Ala Val Leu Lys Glu Phe Ala Glu Lys Ala Asn Ile Pro Val Thr
                325                 330                 335
```

```
Thr Thr Met Gln Gly Leu Gly Gly Phe Asp Glu Arg Ser Pro Leu Ser
        340                 345                 350

Leu Lys Met Leu Gly Met His Gly Ser Ala Tyr Ala Asn Tyr Ser Met
        355                 360                 365

Gln Asn Ala Asp Leu Ile Leu Ala Leu Gly Ala Arg Phe Asp Asp Arg
        370                 375                 380

Val Thr Gly Arg Val Asp Ala Phe Ala Pro Glu Ala Arg Arg Ala Glu
385                 390                 395                 400

Arg Glu Gly Arg Gly Gly Ile Val His Phe Glu Ile Ser Pro Lys Asn
                405                 410                 415

Leu His Lys Val Val Gln Pro Thr Val Ala Val Leu Gly Asp Val Val
            420                 425                 430

Glu Asn Leu Ala Asn Val Thr Pro His Val Gln Arg Gln Glu Arg Glu
            435                 440                 445

Pro Trp Phe Ala Gln Ile Ala Asp Trp Lys Glu Lys His Pro Phe Leu
        450                 455                 460

Leu Glu Ser Val Asp Ser Asp Lys Val Leu Lys Pro Gln Gln Val
465                 470                 475                 480

Leu Thr Glu Leu Asn Lys Gln Ile Leu Glu Ile Gln Glu Lys Asp Ala
                485                 490                 495

Asp Gln Glu Val Tyr Ile Thr Thr Gly Val Gly Ser His Gln Met Gln
            500                 505                 510

Ala Ala Gln Phe Leu Thr Trp Thr Lys Pro Arg Gln Trp Ile Ser Ser
            515                 520                 525

Gly Gly Ala Gly Thr Met Gly Tyr Gly Leu Pro Ser Ala Ile Gly Ala
        530                 535                 540

Lys Ile Ala Lys Pro Asp Ala Ile Val Ile Asp Ile Asp Gly Asp Ala
545                 550                 555                 560

Ser Tyr Ser Met Thr Gly Met Glu Leu Ile Thr Ala Ala Glu Phe Lys
                565                 570                 575

Val Gly Val Lys Ile Leu Leu Leu Gln Asn Asn Phe Gln Gly Met Val
            580                 585                 590

Lys Asn Val Gln Asp Leu Phe Tyr Asp Lys Arg Tyr Ser Gly Thr Ala
            595                 600                 605

Met Phe Asn Pro Arg Phe Asp Lys Val Ala Asp Ala Met Arg Ala Lys
        610                 615                 620

Gly Leu Tyr Cys Ala Lys Gln Ser Glu Leu Lys Asp Lys Ile Lys Glu
625                 630                 635                 640

Phe Leu Glu Tyr Asp Glu Gly Pro Val Leu Leu Glu Val Phe Val Asp
                645                 650                 655

Lys Asp Thr Leu Val Leu Pro Met Val Pro Ala Gly Phe Pro Leu His
            660                 665                 670

Glu Met Val Leu Glu Pro Pro Lys Pro Lys Asp Ala
            675                 680

<210> SEQ ID NO 25
<211> LENGTH: 18
<212> TYPE: DNA
<213> ORGANISM: Schizochytrium sp.

<400> SEQUENCE: 25
gttgaccagt gccgttcc                                              18

<210> SEQ ID NO 26
```

```
<211> LENGTH: 18
<212> TYPE: DNA
<213> ORGANISM: Schizochytrium sp.

<400> SEQUENCE: 26
cgaagtgcac gcagttgc                                                       18

<210> SEQ ID NO 27
<211> LENGTH: 31
<212> TYPE: DNA
<213> ORGANISM: Schizochytrium sp.

<400> SEQUENCE: 27
gcgcccatgg gacgtcaggt ggcactttc g                                         31

<210> SEQ ID NO 28
<211> LENGTH: 36
<212> TYPE: DNA
<213> ORGANISM: Schizochytrium sp.

<400> SEQUENCE: 28
gcgcccatgg ccgcggcaag cagcagatta cgcgca                                   36

<210> SEQ ID NO 29
<211> LENGTH: 1263
<212> TYPE: DNA
<213> ORGANISM: Caenorhabditis elegans
<220> FEATURE:
<221> NAME/KEY: CDS
<222> LOCATION: (23)..(1228)
<223> OTHER INFORMATION:

<400> SEQUENCE: 29
```

| | | | |
|---|---|---|---|
| gcggccgcga attcagatct cc atg gtc gct cac tcg tcg gag ggt ctc tcg | | | 52 |
| Met Val Ala His Ser Ser Glu Gly Leu Ser | | | |
| 1               5                    10 | | | |
| | | | |
| gcc acc gcc ccg gtc acc ggc ggc gac gtc ctc gtc gac gcc cgc gcc | | | 100 |
| Ala Thr Ala Pro Val Thr Gly Gly Asp Val Leu Val Asp Ala Arg Ala | | | |
|             15                  20                  25 | | | |
| | | | |
| tcg ctc gag gag aag gag gcc ccg cgc gac gtc aac gcc aac acc aag | | | 148 |
| Ser Leu Glu Glu Lys Glu Ala Pro Arg Asp Val Asn Ala Asn Thr Lys | | | |
|         30                  35                  40 | | | |
| | | | |
| cag gcc acc acc gag gag ccc cgc atc cag ctg ccc acc gtc gac gcc | | | 196 |
| Gln Ala Thr Thr Glu Glu Pro Arg Ile Gln Leu Pro Thr Val Asp Ala | | | |
|     45                  50                  55 | | | |
| | | | |
| ttc cgc cgc gcc atc ccc gcc cac tgc ttc gag cgc gac ctc gtc aag | | | 244 |
| Phe Arg Arg Ala Ile Pro Ala His Cys Phe Glu Arg Asp Leu Val Lys | | | |
| 60                  65                  70 | | | |
| | | | |
| tcg atc cgc tac ctc gtc cag gac ttc gcc gcc ctc acc atc ctc tac | | | 292 |
| Ser Ile Arg Tyr Leu Val Gln Asp Phe Ala Ala Leu Thr Ile Leu Tyr | | | |
| 75                  80                  85                  90 | | | |
| | | | |
| ttc gcc ctc ccc gcc ttc gag tac ttc ggc ctc ttc ggc tac ctc gtc | | | 340 |
| Phe Ala Leu Pro Ala Phe Glu Tyr Phe Gly Leu Phe Gly Tyr Leu Val | | | |
|                 95                  100                 105 | | | |
| | | | |
| tgg aac atc ttc atg ggc gtc ttc ggc ttc gcc ctc ttc gtc gtc ggc | | | 388 |
| Trp Asn Ile Phe Met Gly Val Phe Gly Phe Ala Leu Phe Val Val Gly | | | |
|             110                 115                 120 | | | |
| | | | |
| cac gac tgc ctc cac gga agc ttc tcg gac aac cag aac ctc aac gac | | | 436 |
| His Asp Cys Leu His Gly Ser Phe Ser Asp Asn Gln Asn Leu Asn Asp | | | |
|         125                 130                 135 | | | |
| | | | |
| ttc atc ggc cac atc gcc ttc tcg ccc ctc ttc tcg ccc tac ttc ccc | | | 484 |
| Phe Ile Gly His Ile Ala Phe Ser Pro Leu Phe Ser Pro Tyr Phe Pro | | | |
|     140                 145                 150 | | | |

```
tgg cag aag tcg cac aag ctc cac cac gcc ttc acc aac cac atc gac       532
Trp Gln Lys Ser His Lys Leu His His Ala Phe Thr Asn His Ile Asp
155                 160                 165                 170 aag gac cac ggc cac gtc tgg atc cag gac aag gac tgg gag gcc atg       580
Lys Asp His Gly His Val Trp Ile Gln Asp Lys Asp Trp Glu Ala Met
                175                 180                 185 ccc tcg tgg aag cgc tgg ttc aac ccc atc ccc ttc tcg ggc tgg ctc       628
Pro Ser Trp Lys Arg Trp Phe Asn Pro Ile Pro Phe Ser Gly Trp Leu
            190                 195                 200 aag tgg ttc ccc gtc tac acc ctc ttc ggc ttc tgc gac ggc tcg cac       676
Lys Trp Phe Pro Val Tyr Thr Leu Phe Gly Phe Cys Asp Gly Ser His
        205                 210                 215 ttc tgg ccc tac tcg tcg ctc ttc gtc cgc aac tcg gac cgc gtc cag       724
Phe Trp Pro Tyr Ser Ser Leu Phe Val Arg Asn Ser Asp Arg Val Gln
    220                 225                 230 tgc gtg atc agc ggc atc tgc tgc gtc tgc gcc tac atc gcc ctc           772
Cys Val Ile Ser Gly Ile Cys Cys Val Cys Ala Tyr Ile Ala Leu
235                 240                 245                 250 acc atc gcc ggc tcg tac tcg aac tgg ttc tgg tac tac tgg gtc ccg       820
Thr Ile Ala Gly Ser Tyr Ser Asn Trp Phe Trp Tyr Tyr Trp Val Pro
                255                 260                 265 ctc tcg ttc ttc ggc ctc atg ctc gtc atc gtc acc tac ctg cag cac       868
Leu Ser Phe Phe Gly Leu Met Leu Val Ile Val Thr Tyr Leu Gln His
            270                 275                 280 gtc gac gac gtc gcc gag gtc tac gag gcc gac gag tgg tcg ttc gtc       916
Val Asp Asp Val Ala Glu Val Tyr Glu Ala Asp Glu Trp Ser Phe Val
        285                 290                 295 cgc ggc cag acc cag acc atc gac cgc tac tac ggc ctc ggc ctc gac       964
Arg Gly Gln Thr Gln Thr Ile Asp Arg Tyr Tyr Gly Leu Gly Leu Asp
    300                 305                 310 acc acc atg cac cac atc acc gac ggc cac gtg gcc cac cac ttc ttc      1012
Thr Thr Met His His Ile Thr Asp Gly His Val Ala His His Phe Phe
315                 320                 325                 330 aac aag atc ccg cac tac cac ctc atc gag gcc acc gag ggc gtc aag      1060
Asn Lys Ile Pro His Tyr His Leu Ile Glu Ala Thr Glu Gly Val Lys
                335                 340                 345 aag gtc ctc gag ccc ctc tcg gac acc cag tac ggc tac aag tcg cag      1108
Lys Val Leu Glu Pro Leu Ser Asp Thr Gln Tyr Gly Tyr Lys Ser Gln
            350                 355                 360 gtc aac tac gac ttc ttc gcc cgc ttc ctc tgg ttc aac tac aag ctc      1156
Val Asn Tyr Asp Phe Phe Ala Arg Phe Leu Trp Phe Asn Tyr Lys Leu
        365                 370                 375 gac tac ctc gtg cac aag acc gcc ggc atc atg cag ttc cgc acc acc      1204
Asp Tyr Leu Val His Lys Thr Ala Gly Ile Met Gln Phe Arg Thr Thr
    380                 385                 390 ctc gag gag aag gcc aag gcc aag taacccgggg gtacccttaa ggcatgcgcg     1258
Leu Glu Glu Lys Ala Lys Ala Lys
395                 400 gccgc                                                                1263

<210> SEQ ID NO 30
<211> LENGTH: 402
<212> TYPE: PRT
<213> ORGANISM: Caenorhabditis elegans

<400> SEQUENCE: 30

Met Val Ala His Ser Ser Glu Gly Leu Ser Ala Thr Ala Pro Val Thr
1               5                   10                  15

Gly Gly Asp Val Leu Val Asp Ala Arg Ala Ser Leu Glu Glu Lys Glu
```

```
                20                  25                  30
Ala Pro Arg Asp Val Asn Ala Asn Thr Lys Gln Ala Thr Glu Glu
            35                  40                  45

Pro Arg Ile Gln Leu Pro Thr Val Asp Ala Phe Arg Arg Ala Ile Pro
50                  55                  60

Ala His Cys Phe Glu Arg Asp Leu Val Lys Ser Ile Arg Tyr Leu Val
65                  70                  75                  80

Gln Asp Phe Ala Ala Leu Thr Ile Leu Tyr Phe Ala Leu Pro Ala Phe
                85                  90                  95

Glu Tyr Phe Gly Leu Phe Gly Tyr Leu Val Trp Asn Ile Phe Met Gly
            100                 105                 110

Val Phe Gly Phe Ala Leu Phe Val Val Gly His Asp Cys Leu His Gly
        115                 120                 125

Ser Phe Ser Asp Asn Gln Asn Leu Asn Asp Phe Ile Gly His Ile Ala
    130                 135                 140

Phe Ser Pro Leu Phe Ser Pro Tyr Phe Pro Trp Gln Lys Ser His Lys
145                 150                 155                 160

Leu His His Ala Phe Thr Asn His Ile Asp Lys Asp His Gly His Val
                165                 170                 175

Trp Ile Gln Asp Lys Asp Trp Glu Ala Met Pro Ser Trp Lys Arg Trp
            180                 185                 190

Phe Asn Pro Ile Pro Phe Ser Gly Trp Leu Lys Trp Phe Pro Val Tyr
        195                 200                 205

Thr Leu Phe Gly Phe Cys Asp Gly Ser His Phe Trp Pro Tyr Ser Ser
    210                 215                 220

Leu Phe Val Arg Asn Ser Asp Arg Val Gln Cys Val Ile Ser Gly Ile
225                 230                 235                 240

Cys Cys Cys Val Cys Ala Tyr Ile Ala Leu Thr Ile Ala Gly Ser Tyr
                245                 250                 255

Ser Asn Trp Phe Trp Tyr Tyr Trp Val Pro Leu Ser Phe Gly Leu
            260                 265                 270

Met Leu Val Ile Val Thr Tyr Leu Gln His Val Asp Asp Val Ala Glu
        275                 280                 285

Val Tyr Glu Ala Asp Glu Trp Ser Phe Val Arg Gly Gln Thr Gln Thr
    290                 295                 300

Ile Asp Arg Tyr Tyr Gly Leu Gly Leu Asp Thr Thr Met His His Ile
305                 310                 315                 320

Thr Asp Gly His Val Ala His His Phe Phe Asn Lys Ile Pro His Tyr
                325                 330                 335

His Leu Ile Glu Ala Thr Glu Gly Val Lys Lys Val Leu Glu Pro Leu
            340                 345                 350

Ser Asp Thr Gln Tyr Gly Tyr Lys Ser Gln Val Asn Tyr Asp Phe Phe
        355                 360                 365

Ala Arg Phe Leu Trp Phe Asn Tyr Lys Leu Asp Tyr Leu Val His Lys
    370                 375                 380

Thr Ala Gly Ile Met Gln Phe Arg Thr Thr Leu Glu Glu Lys Ala Lys
385                 390                 395                 400

Ala Lys

<210> SEQ ID NO 31
<211> LENGTH: 570
<212> TYPE: DNA
<213> ORGANISM: Caenorhabditis elegans
```

```
<400> SEQUENCE: 31
agcagcagat tgcccgaggc cggcggaagg gacgaggccc aggcggctcg tgaaagcgca      60
tttccgaagg cgggctcggc gacgacgccg gcgcggcgac gacggccctg ccggaccggg     120
cctggggtgg acggcgaggc taactaggac ttggggaagc cgagctgagc gacttgagcg     180
ggttgagggg acgaactgtt taggcgcggc cgagtcgtca gagccagcct gtggagaaag     240
aggcgccgcc gagtgcgacg gggaacgctg cgccgacctc gcattgcacc gcatcgcawt     300
cgcaccgcaw tcgcaccgca ccgcatcgca ccgcatcgca tcgagacccg acgcagcgag     360
acgcgacgct gggccttccc ggcgaaaaaa agtgatctgg cttacaaatc ccgagacgag     420
acagacgtcg gcagcagaaa cgaatcagtc gagcagcagc tgcagcagca gcagcagcag     480
cagcagccca tcgcgagcaa gggctcagcc agcagaacac caatcaggcc aagaatcgca     540
cggaagcaag ccttgacatc ctttgccaac                                      570

<210> SEQ ID NO 32
<211> LENGTH: 18
<212> TYPE: DNA
<213> ORGANISM: Schizochytrium sp.

<400> SEQUENCE: 32
gacccgtcat ctatgctg                                                    18

<210> SEQ ID NO 33
<211> LENGTH: 18
<212> TYPE: DNA
<213> ORGANISM: Schizochytrium sp.

<400> SEQUENCE: 33
ctcaaagtga acgatgcc                                                    18

<210> SEQ ID NO 34
<211> LENGTH: 4244
<212> TYPE: DNA
<213> ORGANISM: Schizochytrium sp.

<400> SEQUENCE: 34
tttctctctc tcgagctgtt gctgctgctg ctgctgctgc tgcttccttg ctggttctca      60
cgtccgttcg atcaagcgct cgctcgctcg accgatcggt gcgtgcgtgc gtgcgtgagt     120
cttgttgcca ggcagccgca ggctgtctgt ctgtttgtgt agttttaccc tcggggttcg     180
gggtctgcct gcctcccgct cccgcccgcc gccgccgta tccacccgc tcgcctccgc     240 ccatcgggcc tcgcctcctc gcgccgcacg catcgcgcgc atcgcatgca tcatgctgcc     300
acgcacgggg ggacgcgcgc cccgcgtccc cgccgccgcg cgtcgtcgtc tggcgatgcc     360
gtcgccgccc tccttccttc cctcgcctcc tcttcctccc gagccccct gtcttccttc     420 gcccccgcag cggcgcgcag gaagcgagga gagcggggag gagagaagaa aagaaaagaa     480
aagaaaagaa aataacagcg ccgtctcgcg cagacgcgcg cggccgcgtg cgaggcggcg     540
tgatggggct tctcgtggcg cggctgcggc ctggcccggc ctcgcctttg aggtgcaggc     600
tttgggagag aagagtggga cgcggagaag ataagatggt gccatggcgc aggacggaga     660
ggttgctgaa acttcttcga gcggcacagg cgatggcgag agaccgacag ctgccggcgc     720
ggaggggatg gataccctcc gaggctggca tggacgagct ggccgcgcgg atctggctgg     780
ccgcgcggcg gtgggtccgg aggcgcgagg ttggtttct tcatacctga taccatacgg     840
tattcattct tcctctccag gaaggaagca agtcacatag agtatcacta gcctaatgat     900
```

-continued

```
ggactctatg ttttagggca cgtcggagca gaaggcgcga gcgattcgaa tgcgagcgat      960
agatacagca cagagacctt gccggcgacg cggatgcagg cgagcacgca cgcaccgcac     1020
gcacggcagc ggtgcacgcg ctcctcggca gatgcacggt tctgcgccgc gcctttacat     1080
tttttgattt taggtggtgt gcctgccact ttgaacatca tccacaagtc aacgcagcat     1140
caagaggcaa gcaagtacat acatccattc gaattcaagt tcaagagacg cagcaacagc     1200
cgccgctccg ctcaagctgc agctagctgg ctgacagggc tcgctggctg tagtggaaaa     1260
ttccattcac ttttctgcat ccgcggccag caggcccgta cgcacgttct ctcgtttgtt     1320
tgttcgttcg tgcgtgcgtg cgtgcgtccc agctgcctgt ctaatctgcc gcgcgatcca     1380
acgaccctcg gtcgtcgccg caagcgaaac ccgacgccga cctggccaat gccgcaagaa     1440
tgctaagcgc gcagcaatgc tgagagtaat cttcagccca ccaagtcatt atcgctgccc     1500
aagtctccat cgcagccaca ttcaggcttt ctctctctct ccctccctct ctttctgccg     1560
ggagagaagg aaagacccgc cgccgccgcc tctgcgcctg tgacgggctg tccgttgtaa     1620
gccctcttag acagttccta ggtgccgggc gccgccgcgc ctccgtcgca ggcacacgta     1680
ggcggccacg ggttcccccc gcaccttcca caccttcttc ccccgcagcc ggaccgcgcg     1740
ccgtctgctt acgcacttcg cgcggccgcc gcccgcgaac ccgagcgcgt gctgtgggcg     1800
ccgtcttccg gccgcgtcgg aggtcgtccc cgcgccgcgc tactccgggt cctgtgcggt     1860
acgtacttaa tattaacagt gggacctcgc acaggacctg acggcagcac agacgtcgcc     1920
gcctcgcatc gctggggacg caggcgaggc atcccgcgcg ggccccgcac cggggaggct     1980
gcggggcggc ctcttccggc cggcggccgc atcaggcgga tgacgcaaga gccctcgcag     2040
tcgctcgctc gcgggagcgc agcgcggcgc cagcgtggcc aagctcccgc cccttctggc     2100
tggctgcatg cctgcctgcc tgcctgcctg cgtgcgtgcg tgcgtgcgtg ccttcgtgcg     2160
tgcctgcctt cgtgcgtgcg tgcgtgagtg cggcggaaga gggatcatgc gaggatcaat     2220
cacccgccgc acctcgactt ttgaagaagc gcgatgcga tgcgatgcga tgcgatgcga     2280
cgcgataccg tgcgaggcta cgaagcgagt ctggccggcc gtcatacaac gcacgttttc     2340
gagaaggagg gctggcggag gcgtgcatgc cggcgaccat tgcgaacgcg cgtctcgtg     2400
gctggcgaag gtgcctggag gatctaacga tcgctgctat gatgctatag ctgtgctgat     2460
ccccggtcca ttccaccacg tctgtgcctg ccgcctgacc tgcgcttggc tttccttcaa     2520
gttctcctcc gccgggcctt caggaccgag acgagacctg cagctgcagc tagactcgcg     2580
ctcgctcgcg gaggattcgc cggccgccgg gccggacggg actcgcgagg tcacacggcc     2640
gccggcgatc gcgatggctg tgctgacgta tcgtgcgtg gcagccgtac gtcagcgacg     2700
ccgcctccgt attgtggatt cgttagttgg ttgttggttg atttgttgat taattttttt     2760
gttcgtaggc ttggttatag ctaatagttt agtttatact ggtgctcttc ggtgctgatt     2820
tagctcgact tgggtccaca ccactgcccc tctactgtga atggatcaat ggacgcacga     2880
cgggccgacg aaagtgcgcg agtgaggtaa cctaagcaac ggcggtcttc agaggggacg     2940
cacgccctcc gtcgcagtca gtccagacag gcagaaaagc gtcttaggga ccacgcacgc     3000
acgcacgcac gcacgcacgc ccgcacgcac gctccctccc tcgcgtgcct attttttag     3060
gcttccttcc gcacgggcct acctctcgct ccctcgcctc gccgcaccag gcggcagcag     3120
cgataccctgc cggtgccgcc tccgtcacgc gctcagccgc agctcagccc agccgcgagc     3180
tagggtttgt tcgtcctgaa ttgtttgatt tgatttgatt tgatttgatc cgatccgatc     3240
```

-continued

```
cgatctgatc tgatttgctt tgctttgctt tgtctccctc ccggcgcgga ccaagcgtcc    3300
gtctgcgcgc cgcagcttcc cttcttctcc cagccctcct tctgctcccg cctctcgcgc    3360
aagcacgcag cttcgccgcc gcatccggtc ggtcggtcgg tcgatcgacc cgcctgccgc    3420
tgctgctgtg gccgggcttt tctccatcgg cgactctttc ttctccatac gtcctactac    3480
gtacatacat actgccggct tcctcctctt ccagcgcggc gacggcggca ggctgcgacg    3540
tcgtcgccgc cgcgggcgcc gcgcgcgccg ccgccgccgc ccgcgtcgca gggcctcgtc    3600
gccgccgccg ctccgctccg ctccgaggcc gcgagagggc cgcggcggcg cgatggatgg    3660
atggatggat ggatggatgg atggattttg ttgatcgatg gcggcgcatg gcggagatgg    3720
agcgaggacg agcgcgcgag cgcggcagcc ggattcgcag gcctcgctc gcctcgcgcc    3780 cgctgccgcg cccgccttgc gagcctgcgc gcgagcgag cgagcgagcg agcggggctt    3840
tctttgtctc gcgcgccgct tggcctcgtg tgtcttgtgc ttgcgtagcg ggcgccgcgg    3900
tggaagatgg ctcattcaat cgacccattc acgcacgcac tccggcgcgc agaaaggcc    3960 gaggaggagc agcaagcaaa ccaaaagctc tcgcgctcgc ggtctcgggc tcgagcggtc    4020
tcggagagag agtcttgcgg cgaccaccgg cagcagcagc agcagcagca cgctgtcga    4080 gcacgagcac gagcacgagc acgagcacga gcattcgagc aagaggacag acacggttgt    4140
cagcgcctag ctcgctcgat acagaaagag gcgggttggg cgtaaaaaaa aaggagcacg    4200
caagccgcca gccagccagc tagctagcca gcctgcctgc caaa                     4244
```

<210> SEQ ID NO 35
<211> LENGTH: 4244
<212> TYPE: DNA
<213> ORGANISM: Schizochytrium sp.

<400> SEQUENCE: 35

```
tttctctctc tcgagctgtt gctgctgctg ctgctgctgc tgcttccttg ctggttctca      60
cgtccgttcg atcaagcgct cgctcgctcg accgatcggt gcgtgcgtgc gtgcgtgagt     120
cttgttgcca ggcagccgca ggctgtctgt ctgtttgtgt agtttttaccc tcggggttcg    180 gggtctgcct gcctcccgct cccgcccgcc gccgccgcgta tccacccccgc tcgcctccgc    240 ccatcgggcc tcgcctcctc gcgccgcacg catcgcgcgc atcgcatgca tcatgctgcc    300
acgcacgggg ggacgcgcgc cccgcgtccc cgccgccgcg cgtcgtcgtc tggcgatgcc    360
gtcgccgccc tccttccttc cctgcctcc tcttcctccc gagccccccct gtcttccttc    420 gcccccgcag cggcgcgcag gaagcgagga gagcggggag gagagaagaa aagaaaagaa    480
aagaaaagaa aataacagcg ccgtctcgcg cagacgcgcg cggccgcgtg cgaggcggcg    540 tgatgggggct tctcgtggcg cggctgcggc ctggcccggc ctcgcctttg aggtgcaggc    600
tttgggagag aagagtggga cgcggagaag ataagatggt gccatggcgc aggacggaga    660
ggttgctgaa acttcttcga gcggcacagg cgatggcgag agaccgacag ctgccggcgc    720 ggagggggatg gataccctccc gaggctggca tggacgagct ggccgcgcgg atctggctgg    780
ccgcgcggcg gtgggtccgg aggcgcgagg ttggttttct tcatacctga taccatacgg    840
tattcattct tcctctccag gaaggaagca agtcacatag agtatcacta gcctaatgat    900
ggactctatg ttttagggca cgtcggagca gaaggcgcga gcgattcgaa tgcgagcgat    960
agatacagca cagagacctt gccggcgacg cggatgcagg cgagcacgca cgcaccgcac   1020
gcacggcagc ggtgcacgcg ctcctcggca gatgcacggt tctgcgccgc gcctttacat   1080
tttttgattt taggtggtgt gcctgccact ttgaacatca tccacaagtc aacgcagcat   1140
```

```
caagaggcaa gcaagtacat acatccattc gaattcaagt tcaagagacg cagcaacagc   1200
cgccgctccg ctcaagctgc agctagctgg ctgacagggc tcgctggctg tagtggaaaa   1260
ttccattcac ttttctgcat ccgcggccag caggcccgta cgcacgttct ctcgtttgtt   1320
tgttcgttcg tgcgtgcgtg cgtgcgtccc agctgcctgt ctaatctgcc gcgcgatcca   1380
acgaccctcg gtcgtcgccg caagcgaaac ccgacgccga cctggccaat gccgcaagaa   1440
tgctaagcgc gcagcaatgc tgagagtaat cttcagccca ccaagtcatt atcgctgccc   1500
aagtctccat cgcagccaca ttcaggcttt ctctctctct ccctccctct ctttctgccg   1560
ggagagaagg aaagacccgc cgccgccgcc tctgcgcctg tgacgggctg tccgttgtaa   1620
gccctcttag acagttccta ggtgccgggc gccgccgcgc ctccgtcgca ggcacacgta   1680
ggcggccacg ggttcccccc gcaccttcca caccttcttc ccccgcagcc ggaccgcgcg   1740
ccgtctgctt acgcacttcg cgcggccgcc gcccgcgaac ccgagcgcgt gctgtgggcg   1800
ccgtcttccg gccgcgtcgg aggtcgtccc cgcgccgcgc tactccgggt cctgtgcggt   1860
acgtacttaa tattaacagt gggacctcgc acaggacctg acggcagcac agacgtcgcc   1920
gcctcgcatc gctggggacg caggcgaggc atcccggcgc ggccccgcac cggggaggct   1980
gcggggcggc ctcttccggc cggcggccgc atcaggcgga tgacgcaaga gccctcgcag   2040
tcgctcgctc gcgggagcgc agcgcggcgc cagcgtggcc aagctcccgc cccttctggc   2100
tggctgcatg cctgcctgcc tgcctgcctg cgtgcgtgcg tgcgtgcgtg ccttcgtgcg   2160
tgcctgcctt cgtgcgtgcg tgcgtgagtg cggcggaaga gggatcatgc gaggatcaat   2220
cacccgccgc acctcgactt ttgaagaagc cgcgatgcga tgcgatgcga tgcgatgcga   2280
cgcgataccg tgcgaggcta cgaagcgagt ctggccggcc gtcatacaac gcacgttttc   2340
gagaaggagg gctggcggag gcgtgcatgc cggcgaccat tgcgaacgcg gcgtctcgtg   2400
gctggcgaag gtgcctggag gatctaacga tcgctgctat gatgctatag ctgtgctgat   2460
ccccggtcca ttccaccacg tctgtgcctg ccgcctgacc tgcgcttggc tttccttcaa   2520
gttctcctcc gccgggcctt caggaccgag acgagacctg cagctgcagc tagactcgcg   2580
ctcgctcgcg gaggattcgc cggccgccgg gccggacggg actcgcgagg tcacacggcc   2640
gccggcgatc gcgatggctg tgctgacgta tcgtgcgtg gcagccgtac gtcagcgacg   2700
ccgcctccgt attgtggatt cgttagttgg ttgttggttg atttgttgat taatttttt   2760 gttcgtaggc ttggttatag ctaatagttt agtttatact ggtgctcttc ggtgctgatt   2820
tagctcgact tgggtccaca ccactgcccc tctactgtga atggatcaat ggacgcacga   2880
cgggccgacg aaagtgcgcg agtgaggtaa cctaagcaac ggcggtcttc agaggggacg   2940
cacgccctcc gtcgcagtca gtccagacag gcagaaaagc gtcttaggga ccacgcacgc   3000
acgcacgcac gcacgcacgc ccgcacgcac gctccctccc tcgcgtgcct attttttag   3060 gcttccttcc gcacgggcct acctctcgct ccctcgcctc gccgcaccag gcggcagcag   3120
cgatacctgc cggtgccgcc tccgtcacgc gctcagccgc agctcagccc agccgcgagc   3180
tagggtttgt tcgtcctgaa ttgtttgatt tgatttgatt tgatttgatc cgatccgatc   3240
cgatctgatc tgatttgctt tgctttgctt tgtctccctc ccggcgcgga ccaagcgtcc   3300
gtctgcgcgc cgcagcttcc cttcttctcc cagccctcct tctgctcccg cctctcgcgc   3360
aagcacgcag cttcgccgcc gcatccggtc ggtcggtcgg tcgatcgacc cgcctgccgc   3420
tgctgctgtg gccgggcttt tctccatcgg cgactctttc ttctccatac gtcctactac   3480
```

-continued

```
gtacatacat actgccggct tcctcctctt ccagcgcggc gacggcggca ggctgcgacg      3540
tcgtcgccgc cgcgggcgcc gcgcgcgccg ccgccgccgc ccgcgtcgca gggcctcgtc      3600
gccgccgccg ctccgctccg ctccgaggcc gcgagagggc cgcggcggcg cgatggatgg      3660
atggatggat ggatggatgg atggattttg ttgatcgatg gcggcgcatg ggcggagatg      3720
agcgaggacg agcgcgcgag cgcggcagcc ggattcgcag ggcctcgctc gcctcgcgcc      3780
cgctgccgcg cccgccttgc gagcctgcgc cgcgagcgag cgagcgagcg agcggggctt      3840
tctttgtctc gcgcgccgct tggcctcgtg tgtcttgtgc ttgcgtagcg ggcgccgcgg      3900
tggaagatgg ctcattcaat cgacccattc acgcacgcac tccggcgcgc agagaaggcc      3960
gaggaggagc agcaagcaaa ccaaaagctc tcgcgctcgc ggtctcgggc tcgagcggtc      4020
tcggagagag agtcttgcgg cgaccaccgg cagcagcagc agcagcagca gcgctgtcga      4080
gcacgagcac gagcacgagc acgagcacga gcattcgagc aagaggacag acacggttgt      4140
cagcgcctag ctcgctcgat acagaaagag gcgggttggg cgtaaaaaaa aaggagcacg      4200
caagccgcca gccagccagc tagctagcca gcctgcctgc caaa                      4244
```